(12) United States Patent
LeCursi et al.

(10) Patent No.: US 11,850,176 B2
(45) Date of Patent: *Dec. 26, 2023

(54) ORTHOTIC JOINT DEVICES, JOINT DEVICE COMPONENTS, AND METHODS

(71) Applicant: Becker Orthopedic Appliance Company, Troy, MI (US)

(72) Inventors: Nicholas LeCursi, Saline, MI (US); Nicholas Zalinski, Macomb Township, MI (US); James Campbell, Clarkston, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,053

(22) Filed: Jul. 8, 2022

(65) Prior Publication Data

US 2022/0339018 A1 Oct. 27, 2022

Related U.S. Application Data

(63) Continuation of application No. 15/586,685, filed on May 4, 2017, now Pat. No. 11,395,753, which is a continuation-in-part of application No. PCT/US2016/037010, filed on Jun. 10, 2016, and a (Continued)

(51) Int. Cl.
*A61F 5/01* (2006.01)
*E05D 11/08* (2006.01)

(52) U.S. Cl.
CPC .......... *A61F 5/0127* (2013.01); *A61F 5/0125* (2013.01); *A61F 2005/0137* (2013.01); *A61F 2005/0158* (2013.01); *A61F 2005/0167* (2013.01); *A61F 2005/0169* (2013.01); *A61F 2005/0179* (2013.01)

(58) Field of Classification Search
CPC ......... E05D 2011/082; E05D 2011/085; E05D 11/081; E05D 11/082; E05D 11/084; E05D 11/10; E05D 11/1007; Y10T 16/54033; Y10T 16/54035; Y10T 16/54038; Y10T 16/547; B60R 16/0215; B60R 16/0222; F16B 5/0258; F16L 15/10; H01B 17/58; H02G 3/083; A61F 5/0123; A61F 5/0125
See application file for complete search history.

(56) References Cited

U.S. PATENT DOCUMENTS 10,500,081 B2 * 12/2019 Campbell ............. A61F 5/0127
11,395,753 B2 * 7/2022 LeCursi ................ A61F 5/0127
(Continued)

*Primary Examiner* — Camtu T Nguyen
(74) *Attorney, Agent, or Firm* — Hinshaw & Culbertson LLP; Roger M. Masson, Esq.

(57) ABSTRACT

Various orthotic joint devices, components, and methods are provided. These include orthotic joint alignment devices for adjusting a neutral or fixed angle of an orthotic joint device independently of other parameters, orthotic joint devices providing staged resistance through staged recruitment of separate springs or initiation of staged spring-rate behavior of a single spring retained in a joint body, adapters for converting non-staged resistance orthotic joint devices into orthotic joint devices, and low-noise orthotic joint devices with intermittent normal force-transmitting contact associated with resistive or assistive forces provided by the devices, and methods of using the devices and components.

18 Claims, 37 Drawing Sheets

Related U.S. Application Data continuation-in-part of application No. 14/738,212, filed on Jun. 12, 2015, now Pat. No. 10,500,081.

(56) References Cited

U.S. PATENT DOCUMENTS

2010/0256543 A1* 10/2010 McCune ............... A61F 5/0125 602/16
2016/0151190 A1* 6/2016 Lurssen ............... A61F 5/0125 601/16

* cited by examiner

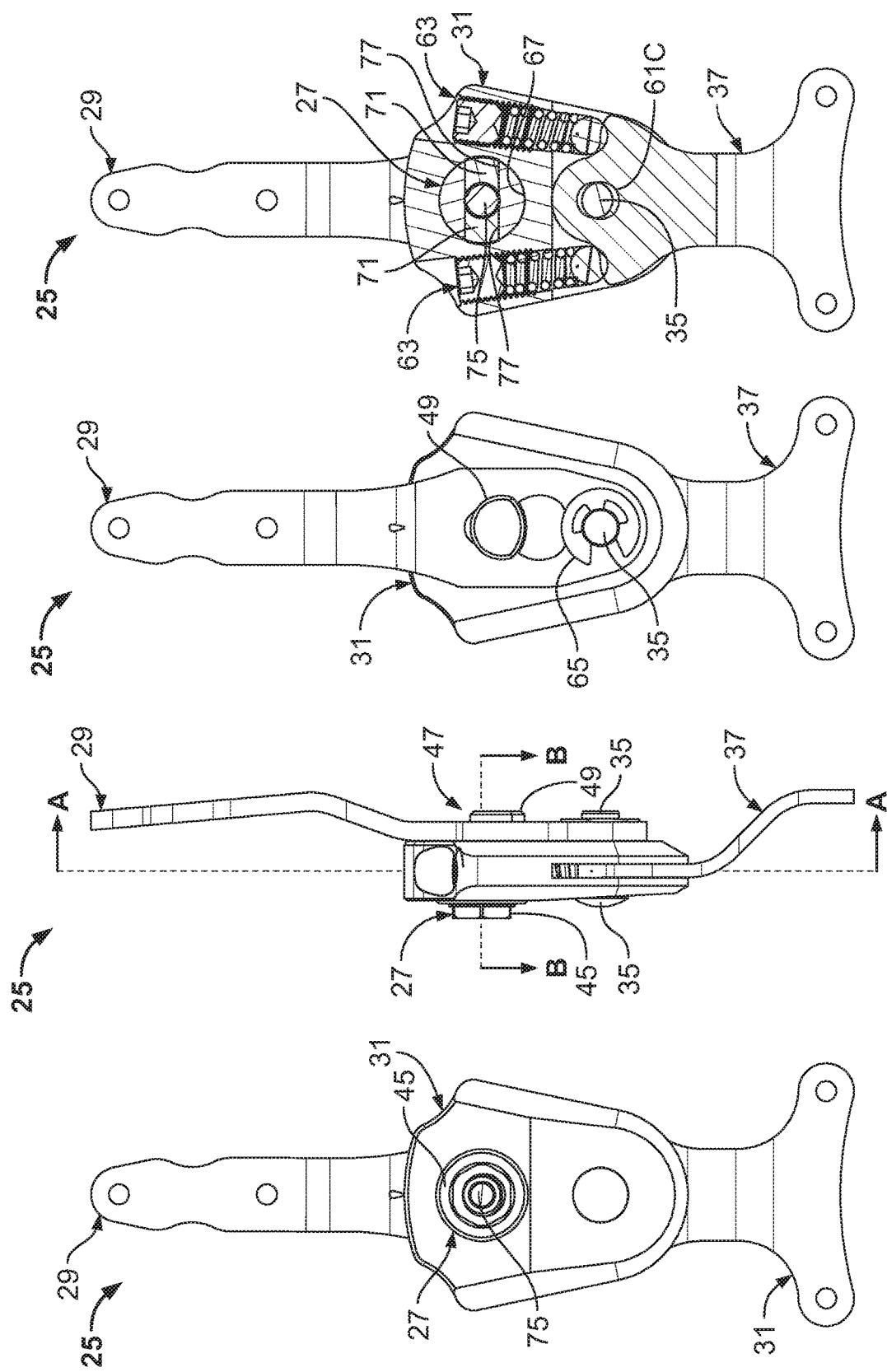

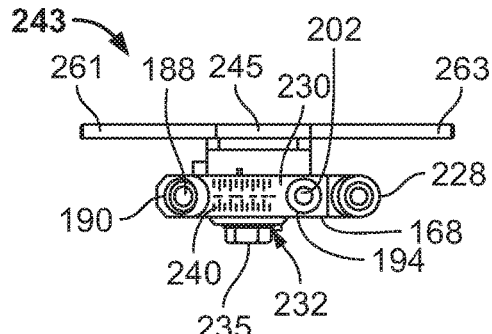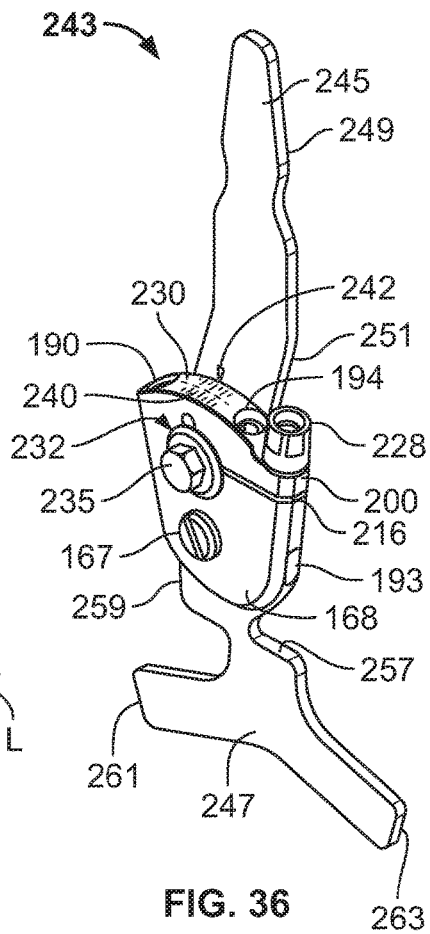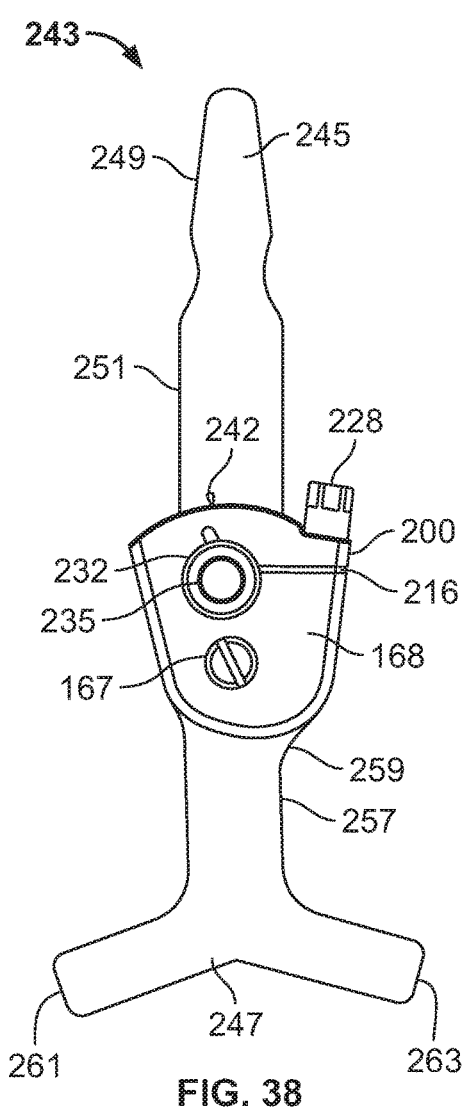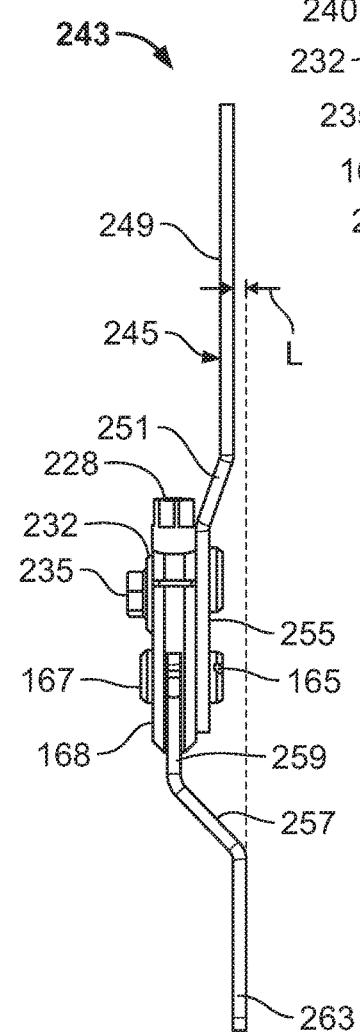
FIG. 37
FIG. 36
FIG. 38
FIG. 39

ORTHOTIC JOINT DEVICES, JOINT DEVICE COMPONENTS, AND METHODS

CROSS REFERENCE TO RELATED APPLICATION

This application is a continuation of U.S. patent application Ser. No. 15/586,685, filed May 4, 2017 which is a continuation-in-part of International Application No. PCT/US2016/037010, filed Jun. 10, 2016 and is a continuation-in-part of U.S. patent application Ser. No. 14/738,212, filed Jun. 12, 2015, now U.S. Pat. No. 10,500,081, issued Dec. 10, 2019, the entire disclosures of which are hereby incorporated by reference.

FIELD OF THE INVENTION

The present invention relates to orthotic joint devices, components, and methods and more particularly to an orthotic joint alignment device, orthotic joint devices with angle dependent torque-angle response, reversible orthotic joint devices, orthotic joint device resistive component adapters, orthotic joint device acoustic noise dampers, and methods of using the same.

BACKGROUND

Orthotic joint devices typically include at least one joint member for attachment to one part of a wearer's body and may also include, for example, another joint member for attachment to another part of the wearer's body, where the two parts of the wearer's body are (or would be in a healthy person) connected by a biological joint of the wearer. For a given type of device, the value of a fixed or neutral angle between the first and second joint members desired for a particular wearer may depend on a variety of factors, including, for example, the wearer's physiology and the nature and severity of the wearer's injury or other therapeutic need for the device. In addition, the same wearer may require different fixed or neutral angles to accommodate different situations and/or a fixed or neutral angle that changes as a therapy or treatment progresses. However, orthotic joint devices are generally expensive to manufacture and customize, and it would thus be impractical to provide as many orthopedic joint devices as there are desired fixed or neutral angles.

A need therefore exists for an orthotic joint device providing an adjustable fixed or neutral angle, without compromising the stability, strength, or therapeutic or supportive effectiveness of the device.

Various types of devices exist for orthotic management of lower limb biomechanical deficits. For example, one type of orthotic ankle joint device includes a joint component with a splint mounting and a stirrup component that pivots relative to the joint component, providing resistance to dorsiflexion and plantarflexion pivotal movements away from a relatively central equilibrium (also termed "neutral" herein) ankle alignment angle of the wearer's lower leg with respect to the ankle, at which angle there is no net biasing force on the device.

To adapt an orthotic ankle joint device to the physiology and condition of the individual wearer, it is advantageous to adjust or tune the equilibrium ankle alignment angle as noted above, and also the plantarflexion resist torque and dorsiflexion resist torque. In addition, it may be advantageous to alter the angle versus torque behavior of the component through the gait cycle to provide support for specific musculoskeletal deficits. Certain existing devices permit adjusting such parameters. However, the ability to adjust each parameter independently of the others is desirable for ease of use and avoidance of inadvertent miscalibration.

A need therefore exists for an orthotic ankle joint device providing independently adjustable resistances to plantarflexion and dorsiflexion, equilibrium ankle alignment angle, and maximum limits on dorsiflexion and plantarflexion movements from the equilibrium ankle alignment angle. In addition, in existing orthotic ankle joint devices, it can be difficult if not impossible to set dorsiflexion resistances that are stiff enough to stabilize the wearer's ankle and knee against hyperflexion while at the same time soft enough to permit natural movement of the joint in a wearer's walking gait. An orthotic ankle joint device to address this challenge is also needed.

In joint devices that provide assistive/resistive torques, it is convenient to use a normal contact cam mechanism to transmit the assistive/resistive torques to the wearer's limb segments supported by the joint device and/or the wearer's supported biological joint, in which a cam follower makes and breaks contact with a contoured surface of a head portion of a limb segment connecting member of the device. Making and breaking force transmitting contact on a cam follower facilitates control of the active range of motion of a resistive component associated with the cam follower, as well as avoiding its interference with another resistive component associated with another cam follower. However, when a cam follower makes initial contact with the stirrup head, acoustic noise is generated and an audible "click" is heard. The sound of the click may be amplified by the structure of the orthosis and may be audible to the user. Like a squeaky shoe, acoustic noise during walking is highly undesirable in orthotic applications.

A need therefore exists for a joint device that permits independent adjustment of resistive torque mechanisms having separate active ranges of motion while limiting acoustic noise to an acceptable level.

In addition, orthotic joint devices tend to be costly to manufacture. Therefore, a need exists to meet each of the foregoing needs by retrofitting or modifying an existing joint device, without replacing the entire device.

SUMMARY OF THE INVENTION

Aspects of the present invention include orthotic joint alignment devices and particular locking mechanisms and linkages thereof, orthotic joint devices including orthotic joint alignment devices, orthotic joint devices producing varied resistance to flexion of a wearer's supported joint in one or more directions, and methods of using the devices.

According to an aspect of the invention, an orthotic joint alignment device (or "alignment device") comprising a locking jaw mechanism is provided. The alignment device comprises first joint member; a second joint member connected to the first joint member for pivotal movement relative to the first joint member about a pivot joint; a cam bushing rotatably retained relative to the first joint member to permit rotation of the cam bushing about a cam bushing axis, the cam bushing axis having a fixed position relative to the first joint member. The cam bushing is also connected to the second joint member so that rotation of the second joint member relative to the first joint member produces rotation of the cam bushing relative to the first joint member. A selectively engageable alignment locking mechanism is configured, when engaged, to restrain the cam bushing from rotating relative to the first joint member.

In an embodiment, the cam bushing is retained by a cam bushing retention surface, the cam bushing retention surface disposed proximate to and facing a retained surface of the cam bushing to restrain movement of the cam bushing relative to the first joint member in a radial direction relative to the cam axis. Thus, the selectively engageable alignment locking mechanism may comprise a first locking member (such as a "cam locking jaw pin" described and illustrated herein) movably retained in the cam bushing for movement of the first locking member generally in said radial direction to selectively engage the cam bushing retention surface to lock rotation of the cam bushing relative to the cam bushing retention surface. Locking engagement of the cam bushing retention surface by the first locking member may be frictional, or may comprise interdigitation of fine, generally axially oriented splines of the first locking member with complementary fine channels of the retention surface. If the engagement is frictional, it may be facilitated by a high-friction, radially outwardly facing surface of the locking members, such as a rough or serrated surface, or a coated or bonded surface layer of a different material than that of other portions of the locking member. On the other hand, in the case of interdigital locking, by "generally axially oriented" splines and channels of the locking member and cam bushing retention surface, it will be understood that the splines and channels are oriented in a direction with a sufficient axial component to essentially lock rotation of the cam bushing about the axis when engaged. For example, the splines and channels may be straight and parallel to the cam bushing axis, or they may be helical, with a relatively large pitch angle.

In conjunction with embodiments in which the locking mechanism comprises a locking member engaging a cam bushing retention surface as just described, the locking member may operate in conjunction with a locking member actuator. For example, the locking member actuator may be movably retained in the cam bushing for generally axial movement of the locking member actuator to selectively impart generally radially outward movement to the locking member to produce said locking engagement of the cam bushing retention surface. The locking member actuator may comprise a threaded rod portion threadably retained in a tapped hole in the cam bushing aligned with the cam bushing axis and a convex conical driving surface (i.e., a driving surface having a shape comprising at least a portion of a geometric cone; the terms "conical" and "frustoconical", referring to a portion of a cone with its tip removed, may be used interchangeably for purposes of the alignment locking mechanisms described herein) axially aligned with the threaded rod portion, the convex conical driving surface being configured to impart said generally radially outward movement to the first locking member when the locking member actuator is threadably advanced into the tapped hole in the cam bushing. In turn, the locking member itself may comprise a concave conical driven surface at a generally radially inner end of the first locking member, said driven surface having being aligned coaxially with said driving surface, having an angle of inclination approximately equal to that of said driving surface, and having a major radius and a minor radius at least as large as respective major and minor radii of a portion of the driving surface that abuts the driven surface when the first locking member contacts the cam bushing retention surface. In this manner, the locking member actuator driving surface will be able to rotate smoothly in the locking member driven surface while maintaining normal contact.

In an embodiment, a second locking member is similarly disposed generally opposite the first locking member, so that the two locking members brace against generally diametrically opposite portions of the cam bushing retention when engaged, like opening "jaws," as in the cam locking "jaw" pins described and illustrated herein. Similarly, more than two locking members may be employed, preferably disposed at evenly spaced angular positions around the cam bushing axis.

Although the first locking member just described and cam locking jaw pins, described and illustrated hereinbelow, are retained in the cam bushing, the alignment locking mechanism may alternatively comprise, for example, a locking member movably retained in a cam bushing retention member that includes the cam bushing retention surface. Thus, generally radial movement of the locking member may selectively engage the retained surface of the cam bushing to lock rotation of the cam bushing relative to the cam bushing retention surface. Also, while the cam bushing retention surface is described and illustrated hereinbelow as a radially inwardly facing, generally cylindrical surface, it may alternatively be a generally radially outwardly facing spindle affixed to the first joint member, the cam bushing having a generally hollow cylindrical interior retained surface configured to receive and rotate about the spindle, thus allowing for a locking mechanism similar to the described and illustrated cam locking jaw pin mechanism, but in which the jaw pins are retained in the non-rotating spindle.

According to another aspect of the invention, an orthotic joint alignment device (or "alignment device") comprising an eccentric cam pin and slot linkage is provided. Used in conjunction with an orthotic joint device, the alignment device easily permits a user/wearer of an orthotic joint device and/or a therapist to unlock, adjust, and relock an alignment angle of the orthotic joint device without disassembling its components. The alignment device includes a first joint member, a second joint member connected to the first joint member for pivotal movement relative to the first joint member about a pivot joint. The first and second joint members are also connected together by a cam linkage that includes a cam bushing rotatably retained relative to the first joint member to permit rotation of the cam bushing about a cam bushing axis, the cam bushing including an eccentric cam pin retained in an elongate slot of (i.e., disposed in fixed relation to, whether as part of a common unitary body or as part of another unitary body disposed in fixed relation to) the second joint member. The eccentric cam pin is displaced at a fixed distance from the cam bushing axis in a radial direction perpendicular to the cam bushing axis to permit revolution of the eccentric cam pin around the cam bushing axis when the cam bushing rotates about the cam bushing axis. The cam slot, which may, for example, be an elongate cam slot, is configured to guide translational movement of the eccentric cam pin along a length of the cam slot, and the second joint member is configured to impel said translational movement of the eccentric cam pin along the length of the cam slot and to impel revolution of the eccentric cam pin about the cam bushing axis when the second joint member is pivoted relative to the first joint member. In addition, the orthotic alignment device includes a selectively engageable alignment locking mechanism, engagement of the alignment locking mechanism being configured to restrain the cam bushing from rotating relative to the first joint member. Thus, when the alignment locking mechanism is engaged, contact between the eccentric cam pin and cam slot restrains the second joint member from pivoting relative to the first joint member.

Embodiments of the alignment device may include a locking mechanism with a locking member movably retained by the cam bushing, or by a cam bushing retention member comprising a generally axisymmetric cam bushing retention surface, substantially as in an aspect of the invention described above. More particularly, the cam bushing retention surface may be a generally concave frustoconical surface centered on the cam bushing axis, tapering inwardly toward a narrow opening in the first joint member generally facing a proximal open side of the cam slot, while the locking member may comprise a frustoconical segment engagement surface that is complementary to the surface it engages (i.e., the cam bushing retention surface if the locking member is carried by the cam bushing, or the retained surface of the cam bushing if the locking member is carried in the first joint member adjacent the retention surface), providing broad normal contact therewith. The eccentric cam pin may comprise a retention flange portion disposed adjacent a distal open side of the cam slot, the retention flange portion having a transverse dimension larger than a width of the cam slot. In this manner, movement of the locking member or members generally in said radial direction tends to wedge the cam bushing in an axial direction to clamp a portion of the second joint member between the retention flange and a portion of the first joint member adjacent the narrow opening in the first joint member, to produce an enhanced clamping force.

In another embodiment of an alignment device providing clamping in the axial dimension, in which the locking member is carried by the cam bushing, the taper of the frustoconical locking member engagement surface is reversed, and a corresponding groove having a reversed taper is formed in the wall of the cam bushing retention surface for receiving, retaining, and selectively frictionally engaging a radially outer end portion of the locking member. In the illustrated variations of this embodiment shown in FIGS. 5H and 5I, assembly of the cam bushing to the first joint member (e.g., a joint body connecting two limb segment attachment members, or a first limb segment attachment member) may require withdrawing the cam locking screw to permit the cam locking member (or members) to fully retract radially inwardly, and advancing the cam locking screw only when the cam locking member is aligned with the retention surface groove. In this manner, clamping is achieved by the locking member engaging the cam bushing retention surface groove to wedge the cam bushing in a forward axial direction. In one variation (FIG. 5H), the cam bushing retained surface and retention surface are generally cylindrical, and axial clamping is produced between a rear flange of the cam bushing pressing against or otherwise engaging a portion of the first joint member adjacent the cam bushing retention surface, optionally with a friction enhancing washer disposed therebetween, which may, for example, comprise radial locking serrations. In another variation (FIG. 5I), the cam bushing retained and retention surfaces are generally tapered, so that axial clamping is provided by the retained surface itself being wedged axially forwardly against the retention surface.

In other embodiments, alignment locking may be provided the application of frictional clamping in a radially inward direction by flexing of a locking collar. In such embodiments, the alignment device includes a cam bushing retention surface of the first joint member, the cam bushing retention surface disposed proximate to and facing a retained surface of the cam bushing, generally in said radial direction, to restrain movement of the cam bushing relative to the first joint member in said radial direction. For example, the retained surface of the cam bushing may be an annular surface disposed radially inwardly of the cam bushing retention surface. In this manner, the alignment locking mechanism may be configured to apply a radially inward clamping force from the cam bushing retention surface to the retained surface of the cam bushing, to frictionally restrain the cam bushing from rotating relative to the first joint member. The cam bushing retention surface may be comprised in a collar of the first joint member. Thus, for example, a pair of generally parallel collar clamping arms integral to the collar and extending radially outwardly from the cam bushing retention surface may be urged together to produce said radially inward clamping force of the cam bushing retention surface acting on the retained cam bushing surface, by applying a suitable force or moment to flex the cam bushing retention surface generally radially inwardly. The collar is preferably a strong, elastically deformable member, thus requiring a deliberate application of the force or moment to apply clamping, and elastically returning to a non-clamping relaxed state when the force or moment is removed. The force or moment urging the clamping arms together may be effected by a collar clamp configured to apply a transverse force to the clamping arms. One example of a suitable collar clamp comprises a threaded collar clamp bolt and a corresponding collar clamp nut. Such a collar clamp may be configured to be mounted to the collar clamping arms so that tightening the collar clamp nut tends to increase said transverse force applied to the clamping arms, and loosening the collar clamp nut tends to decrease said transverse force. The collar clamp bolt may be of a slotted-shaft or conventional-shaft type. One example of a suitable slotted-shaft collar clamp bolt includes a shaft having a slot with an open end opposite a head of the collar clamp bolt and a closed end relatively proximate to the collar clamp bolt head, the collar clamp bolt slot being configured to receive the collar clamping arms so that the collar clamping arms are retained in the collar clamp bolt slot between the closed end of the collar clamp bolt slot and the collar clamp nut. If the collar clamp bolt has a conventional solid shaft, it may simply be inserted through appropriately sized and positioned bolt holes in the collar clamping arms.

Although not shown in the illustrated embodiments, a suitable alternative alignment locking mechanism for use in accordance with the invention may employ normal contact restraint instead of frictional restraint. Such a locking mechanism may comprise, for example, a retractable pin or latch configured to engage a selected one of a plurality of openings, or a retractable ratchet pawl configured to engage a selected tooth of a ratchet spindle. Each respective mating counterpart of such alternative locking mechanisms may, for example, be associated with a respective one of the cam bushing retention surface and the retained cam bushing surface.

In accordance with another aspect of the invention, a method is provided for adjusting an alignment of an orthotic joint device comprising the above-described orthotic joint alignment device, where the orthotic joint device includes a first limb segment attachment portion connected to the first joint member of the alignment device and a second limb segment attachment portion connected to the second joint member of the alignment device, the first limb segment attachment portion being configured to be worn on a first limb segment of a wearer of the orthotic joint device, and the second limb segment attachment portion being configured to be worn on a second limb segment of the wearer. The method includes disengaging the alignment locking mechanism to permit pivoting the second joint member relative to the first joint member; pivoting the second joint member relative to the first joint member to adjust an angle of the second joint member relative to the first joint member; and engaging the alignment locking mechanism to restrain the second joint member from pivoting relative to the first joint member. In this manner, the orthotic joint device can be realigned to support the wearer's first and second limb segments at an angle desired for therapeutic or assistive purposes.

For example, fixing an angle between the wearer's first and second limb segments may be indicated, such as to immobilize a joint of the wearer that connects the two limb segments, to promote healing of or prevent injury (or further injury) to the joint or to a bone corresponding to one of the limb segments. In such cases, the respective first and second limb segment attachment portions of the orthotic joint device used in the method are fixedly attached to the respective first and second joint members of the alignment device. In other cases, it may be desired for an orthotic joint device to provide limited relative pivotal mobility of a wearer's first and second limb segments, with or without producing assistive biasing torques. In such instances, at least one of the respective first and second limb segment attachment portions of the orthotic joint device used in the method is movably attached to the respective first or second joint member of the alignment device. If desired, a biasing component (which may be a spring or other suitable resistive element) is configured to produce a biasing torque tending to return the movable limb attachment portion from a flexed to a neutral position relative to the corresponding joint member. The biasing torque provided may, for example, be unidirectional, as when the neutral position of the limb attachment portion is at an extreme end of a permitted range of motion with one degree of freedom, bidirectional, as when the neutral position of the limb attachment portion is between two extreme ends of a permitted range of motion with one degree of freedom, or multidirectional or omnidirectional, as when the movable limb attachment portion is connected to the respective joint member by a universal, ball, or other type of joint providing multiple degrees of freedom, such as to support or replace the mobility of a human hip or ankle joint, or those of a portion of a spine.

According to another aspect of the invention, a triple-action ankle joint device is provided. The device comprises a joint body, which may for example be a clevis-style joint body defining a channel for receiving members connected to the joint body by pins or bolts extending across the channel, an attachment member (which may, for example, be a splint member or a socket for receiving a splint member) pivotally connected to the joint body for opposite dorsiflexion and plantarflexion movements (defined as movements produced by dorsiflexion and plantarflexion of a wearer's foot), a plantarflexion resistance spring, an initial dorsiflexion resistance spring, and a terminal stance dorsiflexion resistance spring.

The plantarflexion resistance spring is configured to bias the attachment member in a dorsiflexion direction relative to the joint body when the attachment member is within a plantarflexion resistance spring active angular range. The plantarflexion resistance spring active angular range begins at a plantarflexion resistance spring recruitment angle and increases in plantarflexion angle therefrom.

Likewise, the initial dorsiflexion resistance spring is configured to bias the attachment member in a plantarflexion direction relative to the joint body when the attachment member is within an initial dorsiflexion resistance spring active angular range, the initial dorsiflexion resistance spring active angular range beginning at an initial dorsiflexion resistance spring recruitment angle and increasing in dorsiflexion angle therefrom.

Additionally, the terminal stance dorsiflexion resistance spring is configured to bias the attachment member in a plantarflexion direction relative to the joint body when the attachment member is within a terminal stance dorsiflexion resistance spring active angular range; the terminal stance dorsiflexion resistance spring active angular range having at least a terminal stance dorsiflexion resistance spring recruitment angle and an angular range increasing in dorsiflexion therefrom. The terminal stance dorsiflexion resistance spring recruitment angle is greater in dorsiflexion than the initial dorsiflexion resistance spring recruitment angle, and typically operates at least in an angular range from the recruitment angle to the maximum dorsiflexion angle of the wearer's gait. In addition, the terminal stance dorsiflexion spring may operate at smaller dorsiflexion angles than its recruitment angle, but as the term "recruitment angle" is defined herein, the initial dorsiflexion resistance spring dominates the torque response of the attachment member between its recruitment angle and that of the terminal stance dorsiflexion resistance spring.

In one embodiment, the initial dorsiflexion resistance spring and the terminal stance dorsiflexion resistance spring are comprised in a single spring. The single spring is in effect a compound or staged spring, having a higher effective spring rate in the terminal stance dorsiflexion resistance spring active angular range than in a range of angles between the initial dorsiflexion resistance spring recruitment angle and the terminal stance dorsiflexion resistance spring recruitment angle. The single spring may be composed of discrete, separate structural sections that produce the respective higher and lower spring rates. Alternatively, for example, the spring may be a uniform mass of material that exhibits non-linear or staged resistance to compression, or it may have evenly distributed gaps or voids along its length, which are diminished in initial lower spring rate phase or mode of spring deflection, and when the gaps or voids are fully closed, the spring may operate in a higher spring rate phase or mode of spring deflection.

Preferably, the attachment member is positionable in at least one neutral angle relative to the joint body in which a net biasing torque transmitted to the attachment member from the joint body is zero. The neutral angle is an angle between the angle of greatest plantarflexion in the plantarflexion resistance spring active angular range and the angle of greatest dorsiflexion in the initial dorsiflexion resistance spring active angular range, such that the attachment member is biased toward the neutral position when a wearer's foot is plantarflexed to the limit of the mechanism or dorsiflexed to the end of a second rocker phase defined by the mechanism. More preferably, the plantarflexion resistance spring active angular range and the initial dorsiflexion resistance spring active angular range do not even partially overlap, but rather only meet at the neutral angle, the neutral angle thus being equal to the angle of least plantarflexion in the plantarflexion resistance spring active angular range and to the angle of least dorsiflexion in the initial dorsiflexion resistance spring active angular range. In this manner, no biasing torque is transmitted to the attachment member at the neutral angle from any of the plantarflexion resistance spring, the initial dorsiflexion resistance spring, and the terminal stance dorsiflexion resistance spring, to facilitate independent substitution of any of those springs, independent adjustment of any of their pre-loads or spring rates, and independent adjustment of any of their active ranges of motion.

Independent adjustment of these torque response and range of motion parameters is achieved, for example, by appropriately sized, shaped, and positioned dorsiflexion resistance and plantarflexion resistance transmission members. In particular, a dorsiflexion transmission member may be operatively connected between the joint body and the attachment member and biased to move toward the attachment member in a direction that opposes dorsiflexion movement of a dorsiflexion-resist contact surface of the attachment member, a fixed dorsiflexion-resist stop restricting the dorsiflexion opposing movement toward the attachment member beyond a neutral position of the dorsiflexion-resist transmission member where the dorsiflexion-resist transmission member abuts the dorsiflexion-resist contact surface of the attachment member disposed at the neutral angle.

Likewise, a plantarflexion-resist transmission member may be operatively connected between the joint body and the attachment member and biased to move toward the attachment member in a direction that opposes plantarflexion movement of a plantarflexion-resist contact surface of the attachment member, a fixed plantarflexion-resist stop restricting the dorsiflexion opposing movement toward the attachment member beyond a neutral position of the plantarflexion-resist transmission member where the plantarflexion-resist transmission member abuts the plantarflexion-resist contact surface of the attachment member disposed at the neutral angle.

For example, the transmission members may be cam follower pins or ball bearings disposed between a spring and a cam surface of the attachment member, whose excursion from respective channels in the joint body in which they are housed is limited by appropriate stop members.

Alternatively, they may simply be the free ends of respective springs affixed to the joint body at opposite ends, in which case the extent of their motion is limited to the position at which the respective spring (or a portion of it comprising the free end) is fully relaxed, and they will not push a cam surface of the attachment member beyond such a point.

In other variations, the initial dorsiflexion resistance spring and terminal stance dorsiflexion resistance spring may be arranged in parallel or in series between the ankle joint body and the attachment member. Further, springs in a parallel arrangement may be positioned as desired, such as concentrically or side-by-side, a side-by-side arrangement advantageously providing the possibility of amplifying the resistance force provided by the terminal stance dorsiflexion resistance spring by employing it to apply a force to the attachment member farther from its pivotal axis. On the other hand, a functionally equivalent concentric parallel arrangement may be more compact in some dimensions than a side-by-side parallel arrangement.

In a parallel arrangement of the dorsiflexion resistance springs, an initial dorsiflexion resisting force may be transmitted from the ankle joint body to the attachment member by a load path avoiding the terminal stance dorsiflexion resistance spring, the terminal stance dorsiflexion resistance spring only beginning to deflect at its recruitment angle, at which point the terminal stance dorsiflexion resistance spring dominates the overall behavior of the parallel arrangement.

In a series arrangement of the dorsiflexion resistance springs, the initial load path may pass through the terminal stance dorsiflexion resistance spring, but the springs are arranged so that they are permitted to deflect by different amounts to transmit an equal force. Thus, if one of the springs has a much lower spring rate/spring constant, as the initial dorsiflexion resistance spring typically does, that spring will dominate the overall behavior of the series arrangement. At the recruitment angle of the terminal stance dorsiflexion resistance spring, the arrangement may transition to parallel, or further deflection of the initial dorsiflexion resistance spring may be halted altogether such that the terminal stance dorsiflexion resistance spring bears essentially all additional dorsiflexion resistance loading.

Recruitment of the terminal stance dorsiflexion resistance spring may be effected by the engagement of an essentially rigid initial range of dorsiflexion limiting member at the terminal stance dorsiflexion resistance spring recruitment angle. This limiting member may, for example, stand in parallel with the initial dorsiflexion resistance spring to isolate the latter from any further deflection, to transmit essentially all of a terminal dorsiflexion resisting force from the terminal stance dorsiflexion resistance spring to the attachment member by a load path avoiding the initial dorsiflexion resistance spring, and to convert essentially all further dorsiflexion movement of the attachment member to deflection of the terminal stance dorsiflexion resistance spring.

The limiting member may initially be spaced by a clearance from a terminal stance dorsiflexion resistance spring engagement surface (e.g., a surface of the spring itself or of a rigid member disposed against an end of the spring) when the attachment member is at the initial dorsiflexion resistance spring recruitment angle. In some embodiments, this clearance is adjustable without affecting a preload (i.e., a load at the neutral angle and/or at a recruitment angle) of either dorsiflexion resistance spring, and in other embodiments, adjusting this clearance changes a preload of one or both springs.

Dorsiflexion movement of the attachment member from the initial dorsiflexion resistance spring recruitment angle to the terminal stance dorsiflexion resistance spring recruitment angle impels movement of the initial range of dorsiflexion limiting member against the terminal stance dorsiflexion resistance spring engagement surface, which in turn impels movement of the terminal stance dorsiflexion resistance spring engagement surface when the attachment member continues to move in dorsiflexion, which in turn produces the terminal stance dorsiflexion resistance force. The terminal stance force increases with dorsiflexion angle at a higher rate than the initial force, which may be effected by greater stiffness of the terminal stance spring and/or a mechanical advantage afforded to the terminal stance spring, such as by positioning it farther from a pivotal axis of the attachment member relative to the joint body than the initial dorsiflexion resistance spring.

In one embodiment, the initial dorsiflexion resistance spring is a helical spring disposed to be loaded in compression by dorsiflexion movement beyond the initial dorsiflexion resistance spring recruitment angle, and the initial range of dorsiflexion limiting member is an elongate rod disposed in an interior channel extending through the initial dorsiflexion resistance spring.

In another embodiment, the terminal stance dorsiflexion resistance spring engagement surface is maintained in a fixed position relative to an attachment member engaging end of the terminal stance dorsiflexion resistance spring, a position of the terminal stance dorsiflexion resistance spring engagement surface being adjustable by adjusting a position of a joint body engaging end of the terminal stance dorsiflexion resistance spring relative to the joint body.

In another embodiment, a first initial range of dorsiflexion limiting member is spaced by a first clearance from a first terminal stance dorsiflexion resistance spring engagement surface when the attachment member is at the initial dorsiflexion resistance spring recruitment angle, the terminal stance dorsiflexion resistance spring being deflectable to produce said terminal dorsiflexion resisting force by movement of said first terminal stance dorsiflexion resistance spring engagement surface, and a first terminal stance dorsiflexion resistance spring engagement surface is fixed relative to an attachment member engaging end of the terminal stance dorsiflexion resistance spring.

Additionally, a second initial range of dorsiflexion limiting member is spaced by a second clearance from a second terminal stance dorsiflexion resistance spring engagement surface when the attachment member is at the initial dorsiflexion resistance spring recruitment angle, the terminal stance dorsiflexion resistance spring being deflectable to produce said terminal dorsiflexion resisting force by movement of said second terminal stance dorsiflexion resistance spring engagement surface. A second terminal stance dorsiflexion resistance spring engagement surface is configured to maintain a fixed position relative to an attachment member engaging end of the terminal stance dorsiflexion resistance spring when subjected to a force in a direction of movement impelled by dorsiflexion movement of the attachment member, said fixed position of the second terminal stance dorsiflexion resistance spring engagement surface being adjustable relative to a position of a joint body engaging end of the terminal stance dorsiflexion resistance spring. The attachment member is configured to move the first initial range of dorsiflexion limiting member toward the first terminal stance dorsiflexion resistance spring engagement surface and the second initial range of dorsiflexion limiting member toward the second terminal stance dorsiflexion resistance spring engagement surface upon further dorsiflexion movement of the attachment member from the initial dorsiflexion resistance spring recruitment angle. In this case, the terminal stance dorsiflexion resistance spring recruitment angle being an angle of the attachment member at which one of the first initial range of dorsiflexion limiting member and the second initial range of dorsiflexion limiting member contacts the respective first or second terminal stance dorsiflexion resistance spring engagement surface.

The attachment member (such as a stirrup-type attachment component for attachment of two such components at left and right sides of a foot orthotic) may comprise a contoured head having a dorsiflexion cam surface and a plantarflexion cam surface to convert its pivotal movement into deflections of the dorsiflexion resistance and plantarflexion resistance springs, respectively. Operatively disposed between the respective cam surfaces and springs are a dorsiflexion cam follower member mounted for linear movement relative to the joint body and a plantarflexion cam follower member mounted for linear movement relative to the joint body.

In one embodiment of an ankle joint device according to the invention, the attachment member is a symmetrical stirrup member to facilitate reversible attachment to an orthotic or other component worn directly on a wearer's limb segment. For example, the attachment member may comprise a first attachment arm extending in a generally forward direction and a second attachment arm extending in a generally rearward direction, the first and second attachment arms being generally symmetrical about a frontal plane perpendicular to the forward and rearward directions. Accordingly, reversing an orientation of the device from a forward facing orientation to a rearward facing orientation does not change a combined shape of the first attachment arm and the second attachment arm in a sagittal plane perpendicular to the frontal plane. Thus, for example, the device may easily be inverted from front to back and switched from one side of a foot orthotic to the opposite side, reversing the action of the device (for example from providing multi-stage plantarflexion resistance and single-stage dorsiflexion resistance to providing multi-stage dorsiflexion resistance and single-stage plantarflexion resistance) without having to switch out any of its components.

The cam follower members may be of a pin type, presenting a generally flat surface for contact with the respective cam surface, a ball type, presenting a generally hemispherical surface for contact with the respective cam surface, or any other suitable type or shape.

Thus, the dorsiflexion cam surface, when in the active angular range of the initial dorsiflexion resistance spring or the terminal stance dorsiflexion resistance spring, engages the dorsiflexion follower member in normal contact so that dorsiflexion rotation of the dorsiflexion cam surface produces a loading translation of the dorsiflexion follower member, resulting in increased dorsiflexion resistance loading of at least one of the initial dorsiflexion resistance spring and the terminal stance dorsiflexion resistance spring.

Conversely, plantarflexion rotation of the dorsiflexion cam surface produces an unloading translation of the dorsiflexion follower pin, resulting in decreased dorsiflexion resistance loading of at least one of the initial dorsiflexion resistance spring and the terminal stance dorsiflexion resistance spring. Likewise, the plantarflexion cam surface, when in the active angular range of the plantarflexion resistance spring, engages the plantarflexion follower member in normal contact so that plantarflexion rotation of the plantarflexion cam surface produces a loading translation of the plantarflexion follower member and increased loading of the plantarflexion resistance spring, and dorsiflexion rotation of the plantarflexion cam surface produces an unloading translation of the plantarflexion follower member and unloading of the plantarflexion resistance spring.

In another embodiment, the attachment member comprising a first attachment arm extending in a generally forward direction and a second attachment arm extending in a generally rearward direction, the first and second attachment arms being generally symmetrical about a frontal plane perpendicular to the forward and rearward directions, so that reversing an orientation of the device from a forward facing orientation to a rearward facing orientation does not change a combined shape of the first attachment arm and the second attachment arm in a sagittal plane perpendicular to the frontal plane.

In accordance with another aspect of the invention, an ankle joint device having an independently adjustable neutral angle is provided. The device may comprise essentially all of the components of the triple action device described above, or it may omit, for example, the terminal stance dorsiflexion resistance spring. In addition, the device comprises a second attachment member pivotally connected to the joint body and extending from the joint body in a direction generally opposite to that in which the first attachment member extends. The device further includes a locking mechanism operable to lock the second attachment member at a selected angle relative to the joint body. One of the attachment members attaches to a wearer's foot, and the other to the corresponding lower leg. Thus, the neutral angle may be adjusted independently of plantarflexion and dorsiflexion ranges of motion and resistance torque preloads and responses. Changing the neutral angle also displaces the absolute extremes of plantarflexion and dorsiflexion of the wearer's foot relative to the wearer's lower leg permitted by the mechanism, as the plantarflexion and dorsiflexion ranges of motion of the device are set relative to the neutral angle.

In accordance with another aspect of the invention, an orthosis is provided including the components of the triple action ankle joint as described above, and further comprising a second attachment member, so that one of the two attachment members can attach to a wearer's leg, and the other to the wearer's foot. In this aspect of the invention, a neutral angle of the second attachment member relative to the lower attachment member may or may not be adjustable.

In accordance with another aspect of the invention, a method of making an ankle joint device is provided. The method comprises forming an assembly of a joint body, an attachment member, a plantarflexion resistance spring, an initial dorsiflexion resistance spring, and a terminal stance dorsiflexion resistance spring, and assembling those components substantially to produce the structure and function described above for the triple action joint.

In accordance with another aspect of the invention, a method of supporting an ankle of a human in a range of dorsiflexion and plantarflexion motions is provided. The method uses a triple action joint device, substantially as described above, and further comprises attaching the attachment member to one of a foot and a lower leg corresponding to said ankle; and attaching the joint body to the other of the foot and the lower leg, the attached attachment member being configured to move in said dorsiflexion direction relative to the attached joint body when the human's foot dorsiflexes and in said plantarflexion direction relative to the attached joint body when the human's foot plantarflexes.

According to yet another aspect of the invention, a staged resistance adapter is provided for use in converting an existing orthotic joint device from a single-stage resistance function to a multi-stage resistance function in one or more active ranges. The existing joint device may comprise a single stage spring (which acts as a first-stage spring when the multi-stage adapter is connected), a joint body, and a limb attachment member pivotally connected to the joint body. The staged resistance adapter comprises an adapter housing, and a second stage spring retained by the adapter housing. Advantageously, the adapter housing retains all components of the adapter to avoid the possibility of components falling out of the adapter housing when the adapter is removed from a joint device, for example to be transferred from one resistance channel to another of the same joint body component. When the adapter is removably connected to a joint body (for example by threading the adapter housing into a threaded plantarflexion or dorsiflexion resistance channel of a clevis type ankle joint body), a first stage spring engaging portion of the adapter, such as an annular lower end face of the adapter housing itself, operatively engages the first stage spring to bias the limb attachment member in a biased pivotal direction (e.g., a plantarflexion or dorsiflexion direction) when the limb attachment member is within a first stage spring active angular range relative to the joint body. Similarly to staged resistance joint devices described above, such as triple action ankle joint devices according to another aspect of the invention, the first stage spring active angular range begins at a first stage spring recruitment angle and increases therefrom in an opposed pivotal direction opposite to the biased pivotal direction.

The second stage spring may advantageously be housed in an interior channel of the adapter housing and likewise configured, when the adapter housing is connected to the joint body, to bias the attachment member in the biased pivotal direction relative to the joint body when the attachment member is within a second stage spring active angular range, the second stage spring active angular range beginning at a second stage spring recruitment angle and increasing therefrom in the opposed pivotal direction, the second stage spring recruitment angle being greater in the opposed pivotal direction than the first stage spring recruitment angle. In the example illustrated herein, the second stage spring engages a cam follower (such as a ball bearing) of the joint device by way of a T-shaped force transmission pin with a head portion of larger diameter than a bottom hole in the adapter housing that slidingly accommodates a protruding shaft portion of the force transmission pin. The distance between the shaft portion of the force transmission pin and the cam follower defines a first active range of motion of the joint device, which may be adjusted (along with a first stage spring preload) by threading the housing into and out of the joint body channel.

According to still another aspect of the invention, a low noise intermittent contact orthotic joint device is provided. The joint device comprises a joint body, a limb attachment member (such as a stirrup or other type of splint member that moves together with a wearer's limb segment), a biasing force transmission member (such as a ball or pin type cam follower) movably connected to the joint body (such as being movably retained in a ball channel or pin slot), and an acoustic damper carried by the limb attachment member, which may, for example, comprise a flat wire clip or leaf spring that generally follows the shape of a head section of the limb attachment member, with intermittent clearances present between the acoustic damper and the limb attachment member head when the acoustic damper is in a relaxed state. The biasing force transmission member is biased in a biased direction toward a stop position relative to the joint body, such as by a separate resistive element or by its own internal stresses if the biasing force transmission member is itself a resistive element. When in the stop position, the biasing force transmission member is obstructed by contact with the joint body (or by contact with a stop member or equivalent structure affixed thereto) from moving in the biased direction past the stop position. At the stop position, the transmission member is also referred to herein as "bottomed out." The limb attachment member is movably connected to the joint body for movement of the limb attachment member into and out of initial normal contact with the biasing force transmission member at a biasing force transmission member recruitment position, and for movement of the limb attachment member within an active range of motion in which the biasing force transmission member is impelled out of the stop position in an opposed direction opposite to the biased direction by a normal contact force from the limb attachment member. The acoustic damper eases the biasing force transmission member into contact with the limb attachment member by obliquely contacting the biasing force transmission member at a range of positions of the limb attachment member near the biasing force transmission member recruitment position. In particular, the acoustic damper is deflected in a deflection direction oblique to a direction of said initial normal contact, while transmitting in response to its deflection an acoustic damping spring force in a direction generally opposite to said deflection direction to limit an amplitude of acoustic vibration of the force transmission member and the limb attachment member following said initial normal contact. It is believed that acoustic noise reduction is thus achieved at least in part by reducing the magnitude of the impact impulse by slowing the impact speed of the force transmission member. In addition, vibration from the impact may be inhibited by the force transmission member being laterally gripped between the acoustic damper and a ball channel or pin slot that retains the force transmission member.

BRIEF DESCRIPTION OF THE DRAWINGS

FIG. 5A is a top plan view of the assembled device shown in FIG. 4.

FIG. 5B is a sectional top plan view of the assembled device shown in FIG. 4.

FIG. 5C is a left side elevation view of the assembled device shown in FIG. 4.

FIG. 5D is a rear elevation view of the assembled device shown in FIG. 4.

FIG. 5E is a right side elevation view of the assembled device shown in FIG. 4.

FIG. 5F is a sectional left side elevation view of the assembled device shown in FIG. 4.

FIG. 36 is a perspective view of an ankle joint device according to another embodiment of the invention.

FIG. 37 is a top plan view of the device shown in FIG. 36.

FIG. 38 is a right side elevation view of the device shown in FIG. 36.

FIG. 39 is a front elevation view of the device shown in FIG. 36.

DETAILED DESCRIPTION OF THE INVENTION

The present disclosure relates to orthotic alignment devices, according to one aspect of the invention, and to orthotic joint devices, according to another aspect of the invention, in which the orthotic alignment devices may optionally be incorporated or used. Embodiments illustrating these and other aspects of the invention are described in detail below.

Orthotic Joint Alignment Devices and Methods

With reference to the accompanying drawings, illustrated embodiments of orthotic joint alignment devices (or "alignment devices") will now be described in detail. The illustrated alignment devices are configured to facilitate adjustment of first and second joint members of a joint device to a desired relative angular orientation and locking of the two joint members in that desired relative angular orientation. The relative angular orientation may correspond to a fixed or a neutral angular orientation of a wearer's limb segments supported by an orthotic joint device in which the orthotic joint alignment device is deployed. For example, in a static orthotic joint device according to the invention, the first and second joint members may be configured to attach directly (i.e., with no intervening movable linkage) to respective first and second limb segments of a wearer, so that the joint device essentially prevents any relative movement of the wearer's limb segments away from an angular orientation corresponding to a fixed angle of the device. Static joint devices according to the invention may, for example, be formed by affixing suitable limb attachment structure (not shown) to first and second joint members 12 and 14 of an orthotic joint alignment device 10, shown in FIGS. 1-2E and described in more detail below. On the other hand, the invention also encompasses dynamic joint devices that include movable linkage configured to be connected between a first limb segment of a wearer and a corresponding first joint member of the alignment device, while the second joint member of the alignment device is attached directly to a wearer's corresponding second limb segment, so that the movable linkage permits relative articulation of the wearer's first and second limb segments even when the alignment device is locked. The movable linkage may be configured to bias the wearer's first limb segment to a desired neutral angle relative to the wearer's second limb segment, the neutral angle being configured to be set by adjusting and locking the angular orientation of the alignment device. Illustrated examples of such dynamic joint devices include orthotic ankle joint devices 52, 116, 137, and 162 shown in FIGS. 6A-33.

Figure 1:
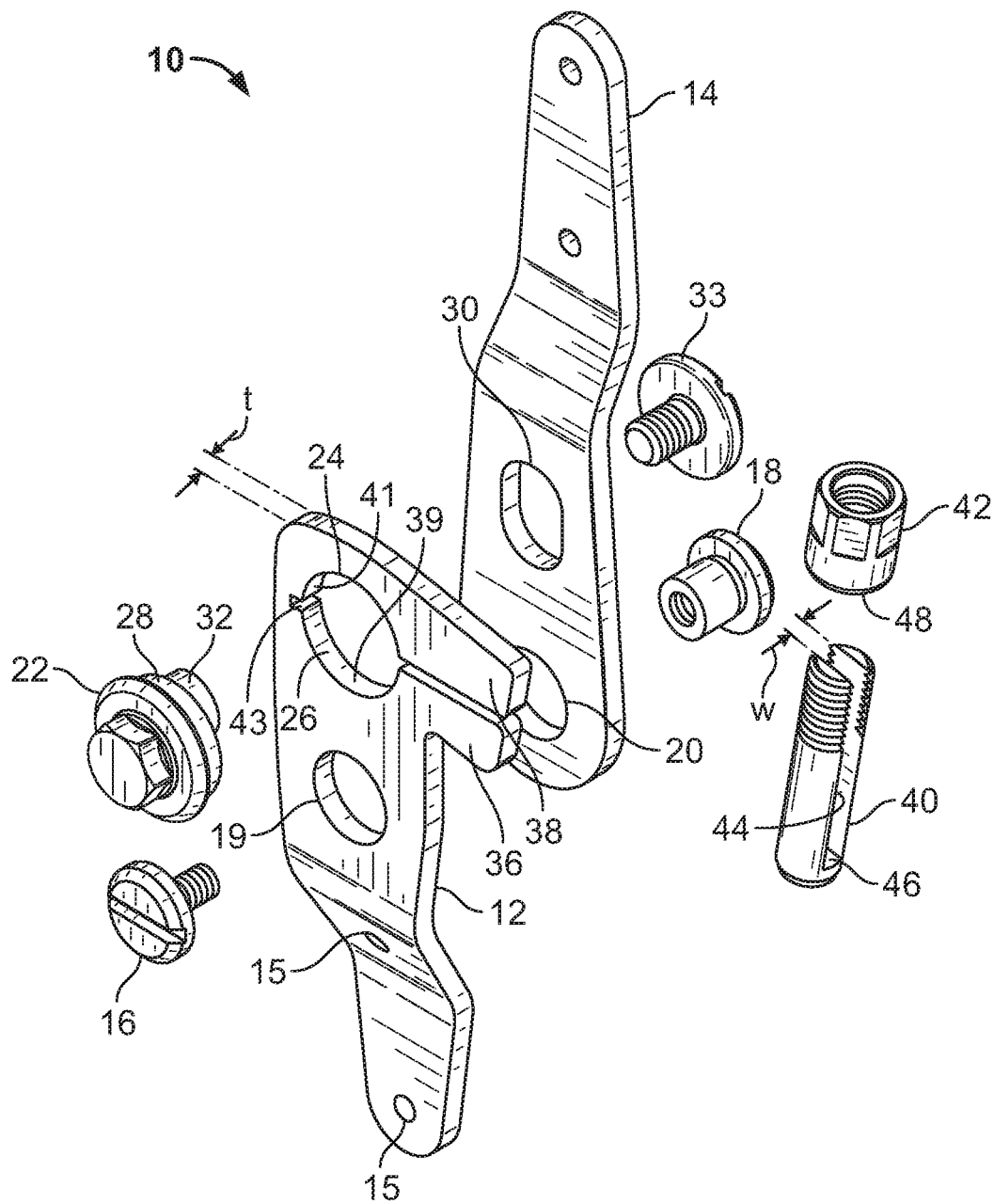
FIG. 1 is a top-right exploded perspective view of an orthotic joint alignment device according to an aspect of the invention.
Figure 2A:
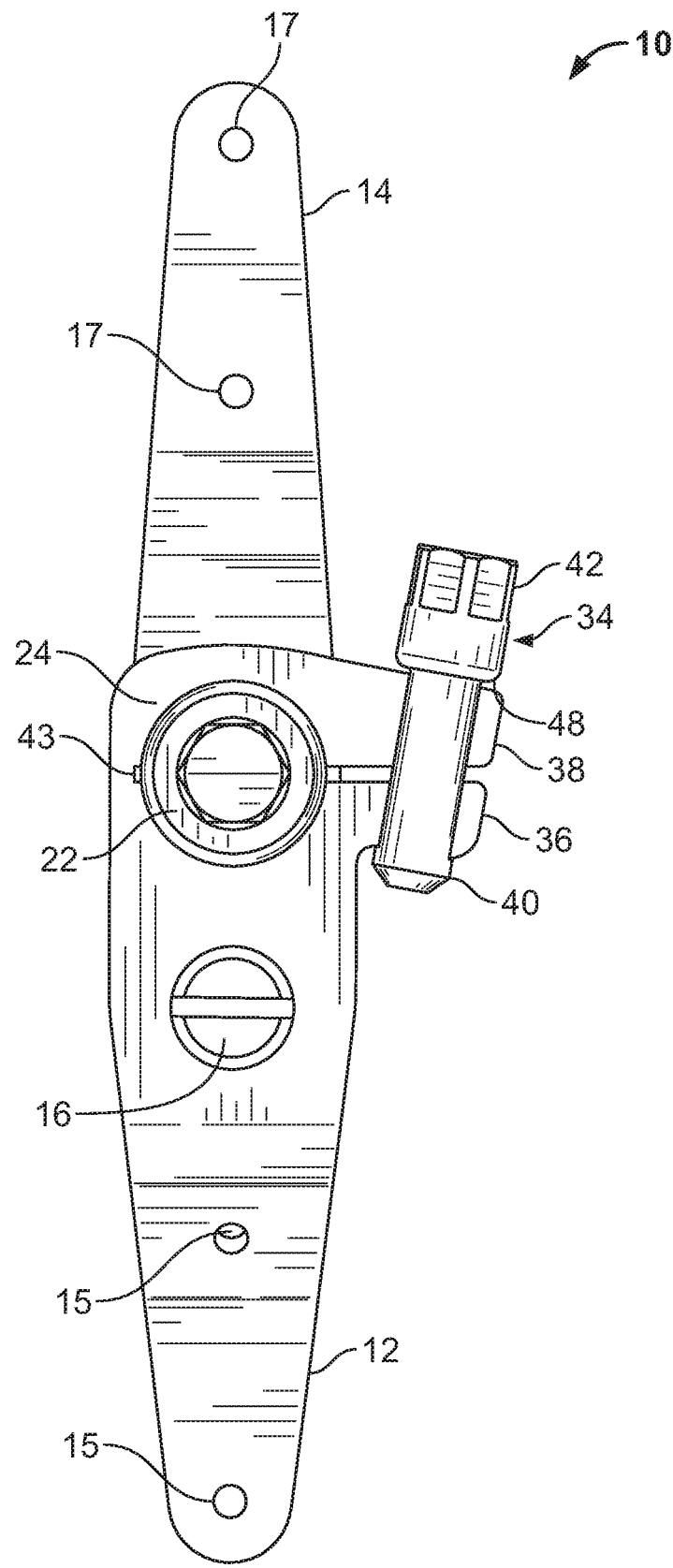
FIG. 2A is a right side elevation view of the device shown in FIG. 1.
Figure 2B:
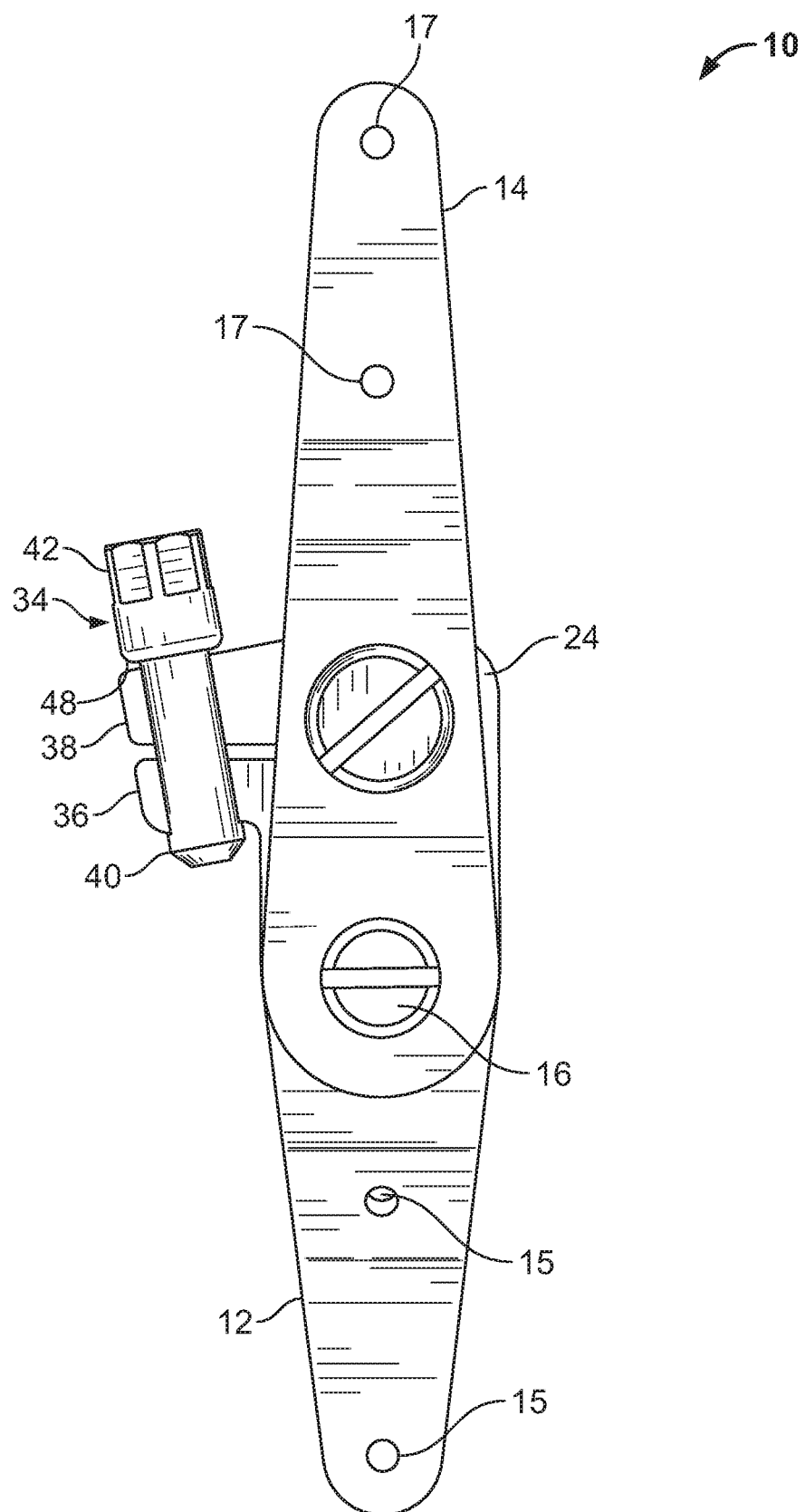
FIG. 2B is a left side elevation view of the device shown in FIG. 1.
Figure 2C:
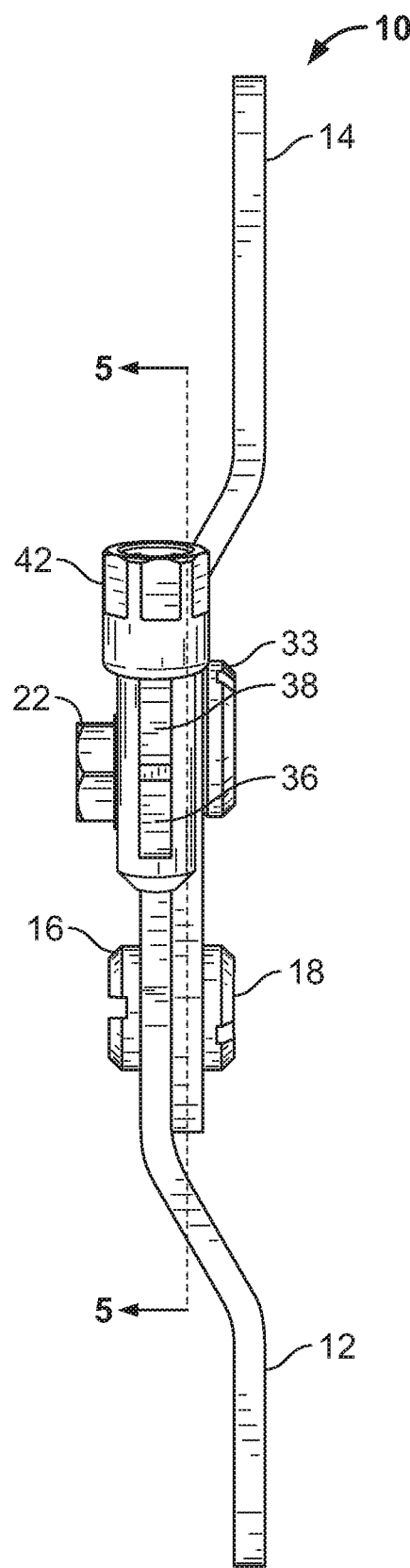
FIG. 2C is a front elevation view of the device shown in FIG. 1
Figure 2D:
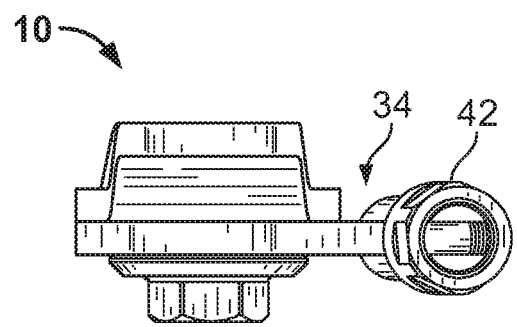
FIG. 2D is a top plan view of the device shown in FIG. 1.
Figure 2E:
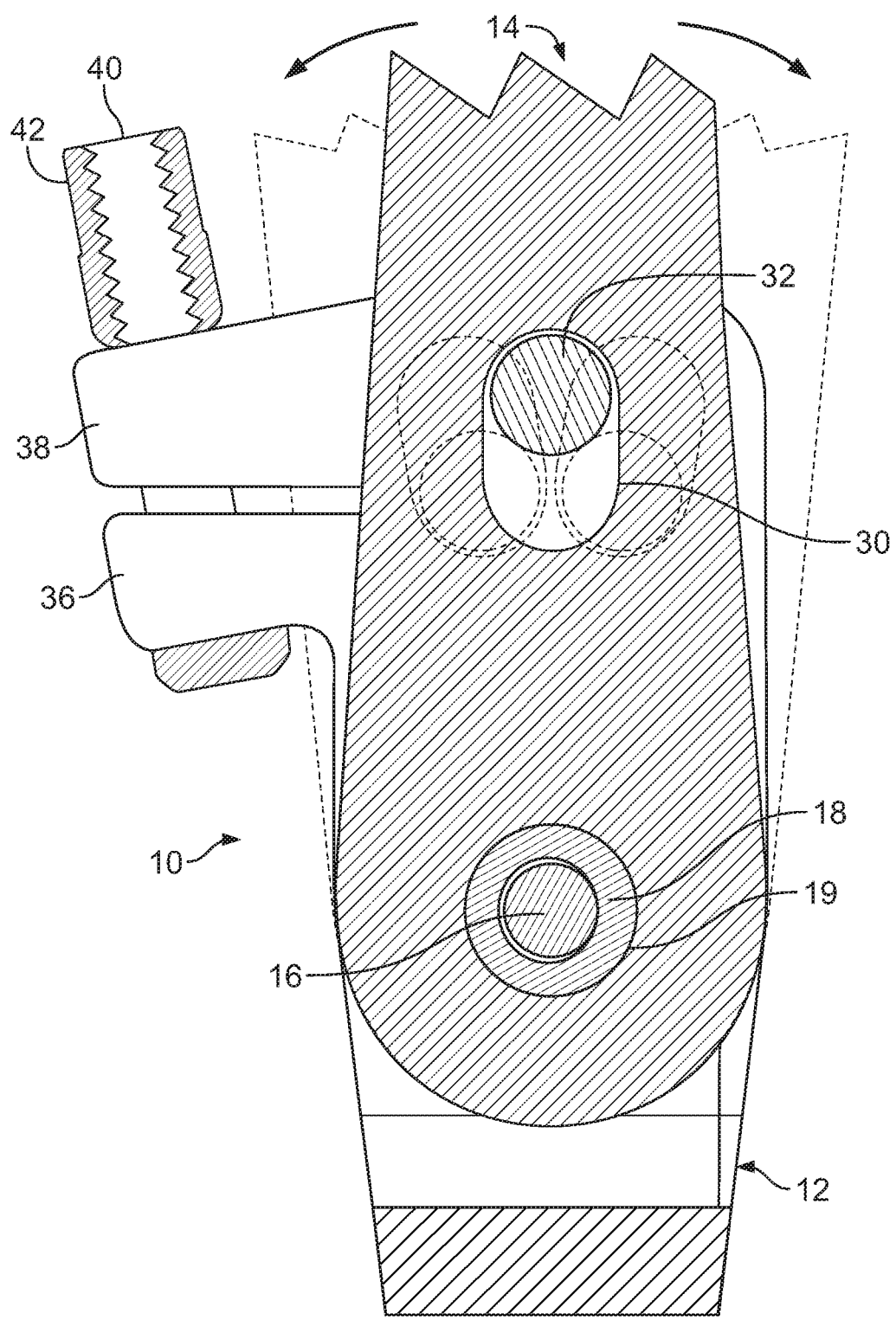
FIG. 2E is a cross sectional, truncated left side elevation view of the device shown in FIG. 1.
Figure 3:
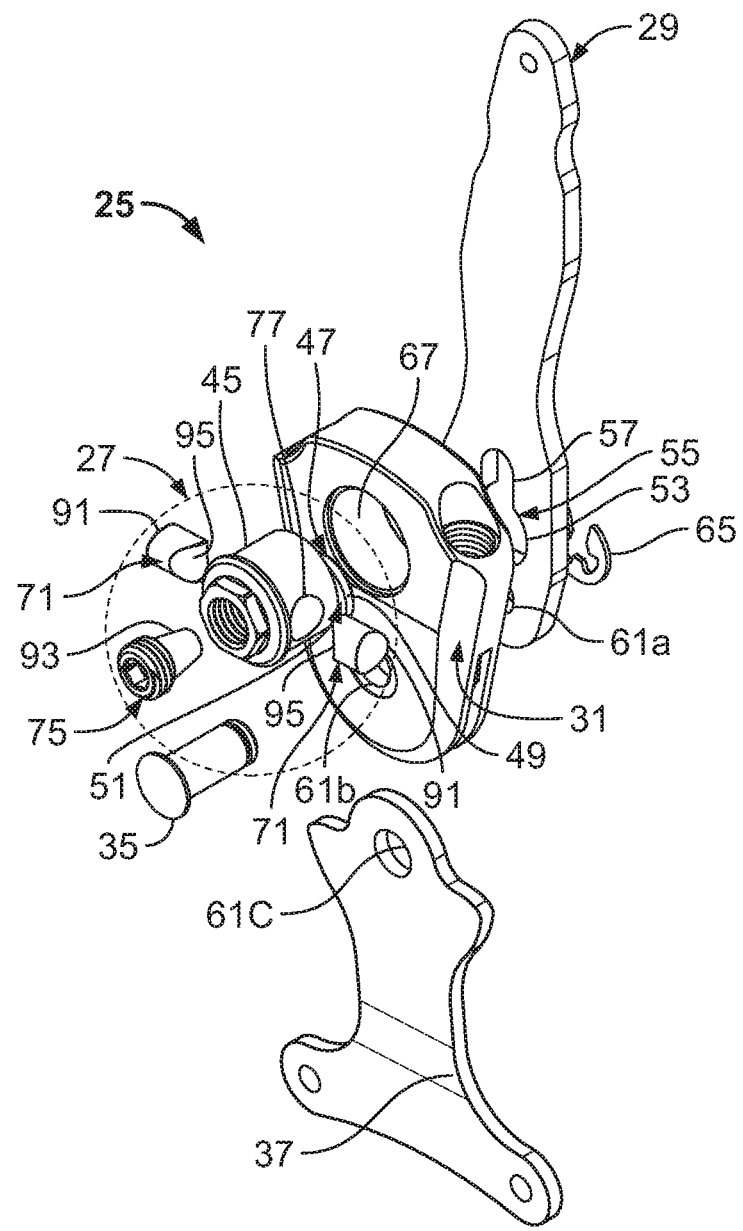
FIG. 3 is an exploded perspective view of a joint device incorporating an alignment device according to another aspect of the invention.
Figure 4:
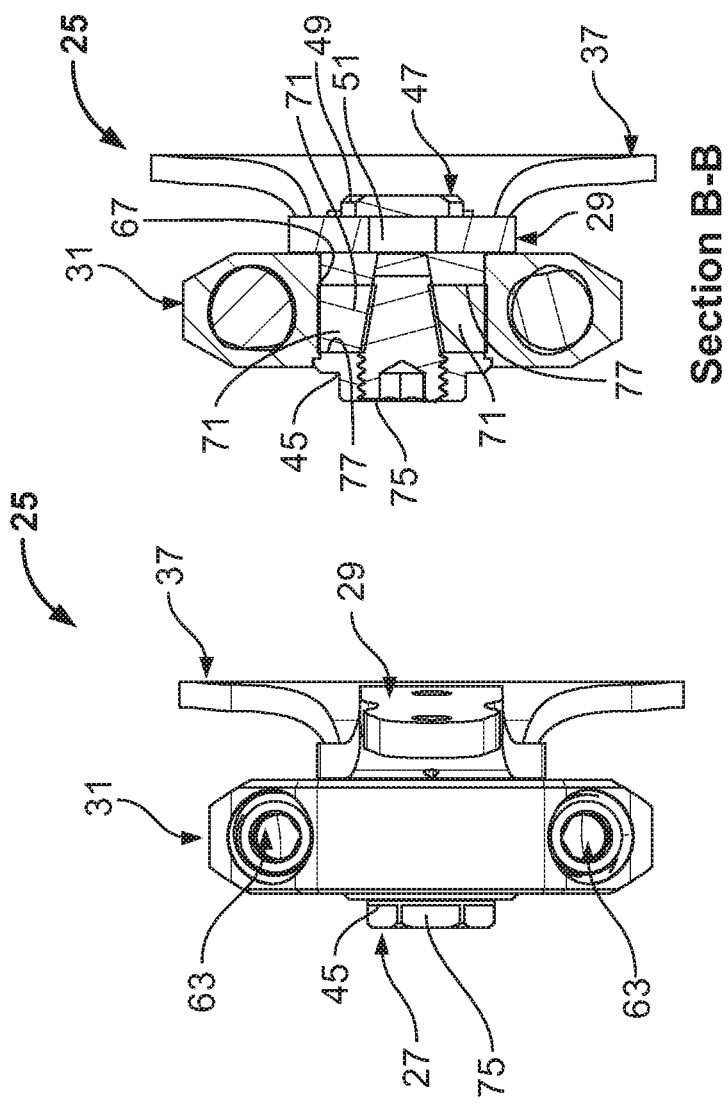
FIG. 4 is an assembled perspective view of the device shown in FIG. 3.
Figure 4:
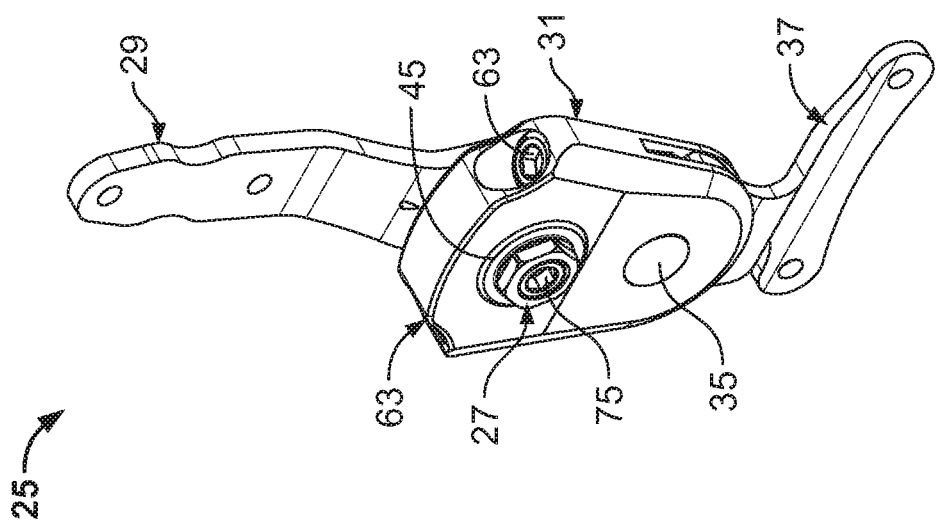

Turning to FIGS. 1-2E, an orthotic joint alignment device 10 is illustrated. Device 10 includes a first joint member 12, for attachment to a first limb segment of a wearer via suitable attachment structure (not shown) that may connect to first joint member 12 using attachment structure mounting holes 15 formed therein, pivotally connected to a second joint member 14, which similarly comprises attachment structure mounting holes 17 for connecting suitable attachment structure (not shown) for attaching second joint member 14 to a second limb segment of a wearer. First joint member 12 is coupled to second joint member 14 by a pivot screw 16 and pivot bushing 18 extending through respective pivot through holes 19, 20 of joint members 12, 14. A cam bushing 22 is rotatably retained in a cam bushing retention collar 24 of first joint member 12. Cam bushing retention collar 24 comprises a generally annular, radially inwardly facing cam bushing retention surface 26 configured to align with a generally annular, radially outwardly facing retained surface 28 of cam bushing 22. Second joint member 14 includes an elongate cam slot 30 configured to retain an eccentric cam pin 32 of cam bushing 22, while a cam pin screw 33 threadably engages cam pin 32 to hold cam pin 32 in cam slot 30 and cam bushing 22 in retention collar 24. In this manner, when second joint member 14 is rotated relative to first joint member 12, cam slot 30 guides translational movement of cam pin 32 with respect to joint member 14.

When cam bushing retention collar 24 is in a relaxed state, cam bushing retention surface 26 transmits relatively little to no normal contact pressure to retained surface 28 of cam bushing 22, permitting cam bushing 22 to rotate relatively freely with respect to first joint member 12 for adjustment of alignment device 10 to a desired angular orientation. Alignment device 10 further includes an alignment locking mechanism 34 to provide (or increase) contact pressure from cam bushing retention surface 26 on retained cam bushing surface 28.

Alignment locking mechanism 34 includes retention collar 24, first and second collar clamping arms 36 and 38 that are radial extensions of collar 24, an alignment locking bolt 40, and an alignment locking nut 42 which serve to tighten collar 24 when nut 42 is tightened to urge clamping arms 36 and 38 together, thereby moving corresponding first and second portions 39 and 41 of cam bushing retention surface 26 closer to each other. The latter relative movement of first and second cam bushing retention surface portions 39 and 41 is facilitated by a notch 43 formed in the interior of collar 24 opposite clamping arms 36 and 38, to provide a reduced section modulus, and thus reduced resistance to bending, of collar 24 proximate to notch 43. In addition, alignment locking bolt 40 and nut 42 are offset radially outwardly from cam bushing retention surface 26 to provide leverage to assist with frictionally locking cam bushing 22. In this manner, alignment locking mechanism 34 is configured to lock cam bushing 22 firmly enough to resist rotation out of a desired fixed or neutral angular position during normal use, such as that resulting from a wearer's limb segments straining to move away from a therapeutically desired angular position supported by a joint device that includes orthotic joint alignment device 10. In alignment device 10, alignment locking bolt 40 is illustrated as a slotted bolt including a slot 44 having a width w sized to a thickness t of clamping arms 36 and 38 to receive and retain clamping arms 36 and 38 between an end surface 46 of slot 44 and an end face 48 of alignment locking nut 42. In other embodiments, such as in the dynamic joint devices described in the following sections with reference to FIGS. 6B-34, a bolt having a solid cylindrical shaft may be employed instead, with the clamping arms including suitable holes to receive the bolt, rather than the bolt receiving the clamping arms.

A variation of the orthotic joint alignment device aspect of the invention is illustrated in FIGS. 3-5F, embodied in a dual-action ankle joint device 25. Joint device 25 comprises a locking cam alignment device 27 configured to selectively lock an angular alignment adjustment of a first limb segment attachment member 29 relative to a joint body 31. Attachment member 29 is pivotally connected to joint body 31 by a pivot pin 35. Joint body 31 is configured to receive a second limb segment attachment member 37 in a lower clevis portion of joint body 31. Second limb segment attachment member 37 is illustrated as a normal contact stirrup member, analogous to those described in more detail below, in the context of staged resistance joint device embodiments of the invention. Alignment device 27 includes a cam bushing 45 having an eccentric cam pin 47 offset radially from an axis of cam bushing 45, similarly to cam bushing 22 of alignment device 10. Cam pin 47 includes a retention flange 49 having a wider periphery than a generally circular rod-shaped cam pin shaft 51. Retention flange 49 is configured to insert into a wide portion 53 of a key hole 55 formed in attachment member 29, permitting cam pin shaft 51 to be received and slidingly retained in a narrow cam slot 57 of key hole 55 by moving attachment member 29 downwardly, with reference to FIG. 3, to align a pivot hole 61a of attachment member 29 with a corresponding pivot hole 61b of joint body 31 and a corresponding pivot hole 61c of second limb segment attachment member 37. When pivot pin 35 is inserted through pivot holes 61a, 61b, 61c and secured by a pivot pin retaining ring 65, attachment member 29 is prevented from moving upwardly relative to joint body 31, so that retention flange 49 is prevented from aligning with wide portion 53 of key hole 55, and alignment cam assembly is thus retained in a cam bore 67 of joint body 31, without the need for a separate retaining ring for securing cam pin 47, in an assembled configuration best seen in FIG. 5E. For illustrative purposes, joint device 25 is illustrated with simple dorsiflexion/plantarflexion resistance assemblies 63 that operate in conjunction with upper contact surfaces of second limb segment attachment member 37. Each assembly 63 is shown to provide only a single stage of resistance with adjustable preload. However, either or both of assemblies 63 may be replaced by a component or assembly providing multi-stage resistance, range of motion adjustments, and/or any other adjustment described in more detail below, in the context of any of the staged resistance joint device embodiments of the invention.

Cam bushing 45 also differs from cam bushing 22 in that it includes an integral locking mechanism in the form of cam locking jaw pins 71 actuated by a cam locking screw 75. Cam locking jaw pins 71 are received in respective transverse holes 77 (shown in FIGS. 3 and 5B) formed in generally diametrically opposite sides of cam bushing 45. Each jaw pin 71 includes a radially outer end engagement surface 91 that generally conforms to a cylindrical curvature of cam bore 67 for locking engagement therewith when jaw pins 71 are forced radially outwardly against bore 67. Such radially outward locking force is applied to jaw pins 71 by advancing cam locking screw 75, so that a convex conical driving surface 93 thereof applies a driving force with a radially outward component to respective complementary concave conical driven surfaces 95 of the radially inward facing ends of jaw pins 71. In one embodiment, jaw pin engagement surfaces 91 are configured to frictionally engage cam bore 67. For example, jaw pin engagement surfaces 91 may comprise a frictional facing, which may, for example, be a serrated surface composed of a material common to other portions of jaw pin 71 or of a different material, a spray-on friction coating, an adhesively retained layer of high-friction material, or a metallurgically bonded metallic layer, such as a Carbinite® tungsten-carbide alloy, applied by electrofusion. Alternatively, engagement surfaces 91 and cam bore 67 may be finely splined, such that, when jaw pins 71 are forced radially outwardly, their respective splines (not shown) interdigitally engage to lock rotation of cam bushing 45, revolution of cam pin 47, and pivotal movement of attachment member 29 relative to joint body 31.

Figure 5G:
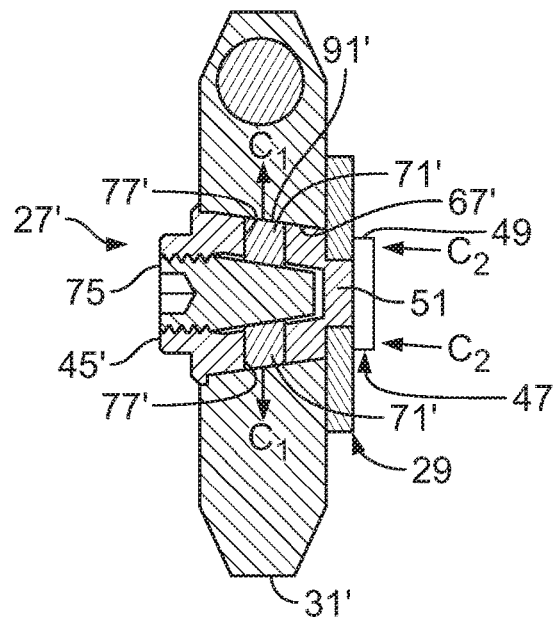
FIG. 5G is a sectional top plan view of another embodiment of an assembled alignment device.
Figure 5H:
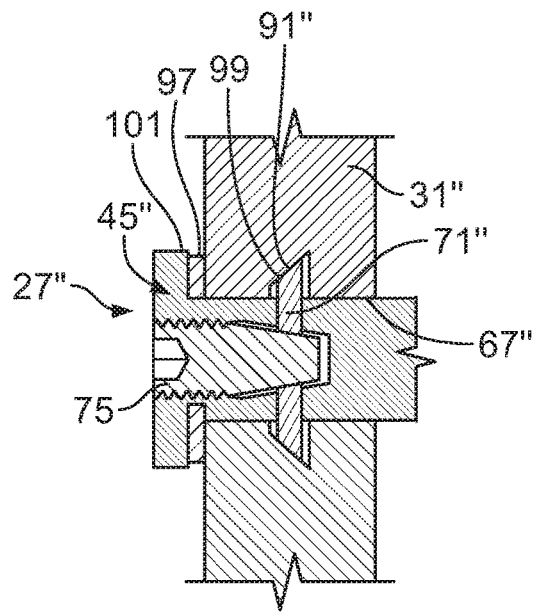
FIG. 5H is a sectional top plan view of another embodiment of an assembled alignment device.
Figure 5I:
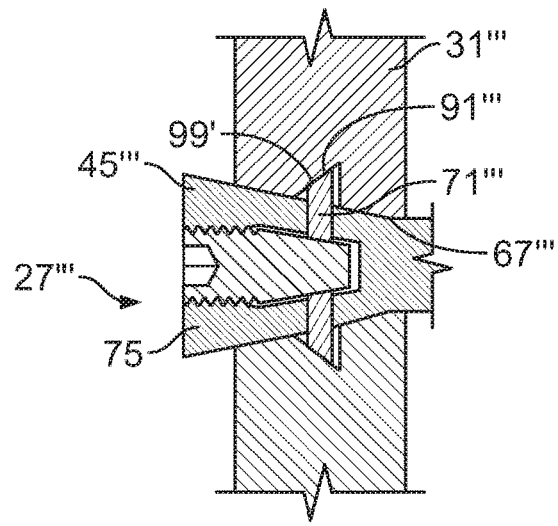
FIG. 5I is a sectional top plan view of another embodiment of an assembled alignment device.

According to three alternative embodiments depicted in FIGS. 5G-5I, a locking cam alignment mechanism includes locking jaw pins with tapered (frustoconical) engagement surfaces, configured to wedge the cam bushing that carries them in an axially forward (proximal-to-distal) or rearward (distal-to-proximal) direction, to introduce an axial dimension to the clamping action of the locking mechanism.

In an embodiment shown in FIG. 5G, a locking cam alignment device 27' includes a cam bushing 45' having a generally frustoconical radially outer retained surface, complementary to a generally frustoconical radially inner retention surface of a cam bore 67' formed in a joint body 31'. Thus, when cam locking screw 75 is advanced to push a pair of jaw pins 71' (whose radially outer jaw pin engagement surfaces 91' may be frustoconical segments complementary to cam bore 67') radially outwardly in transverse holes 77' of cam bushing 45', not only is a primary radially outward clamping force $C_1$ produced against cam bore 67', but also a secondary axially inward clamping force $C_2$ is produced by wedging of engagement surfaces 91' in an axially rearward/distal-to-proximal direction (right to left in FIG. 5G) against the taper of cam bore 67', tending to clamp limb segment attachment member 29 between eccentric cam pin retention flange 49 and joint body 31', for an enhanced overall clamping effect.

In other embodiments, the taper of the cam locking jaw pins is reversed compared to that of locking cam alignment device 27', so as to wedge the cam bushing axially forward as they are engaged. Two variations of such embodiments are illustrated in FIGS. 5H and 5I as locking cam alignment devices 27" and 27'". In these embodiments, assembly of a cam bushing to a joint body requires withdrawing a cam locking screw to permit cam locking members to fully retract radially inwardly (not shown), and advancing the cam locking screw only when the cam locking member is aligned with the retention surface groove. Clamping is achieved by the locking member engaging the cam bushing retention surface groove to wedge the cam bushing in a forward axial direction.

Figure 5J:
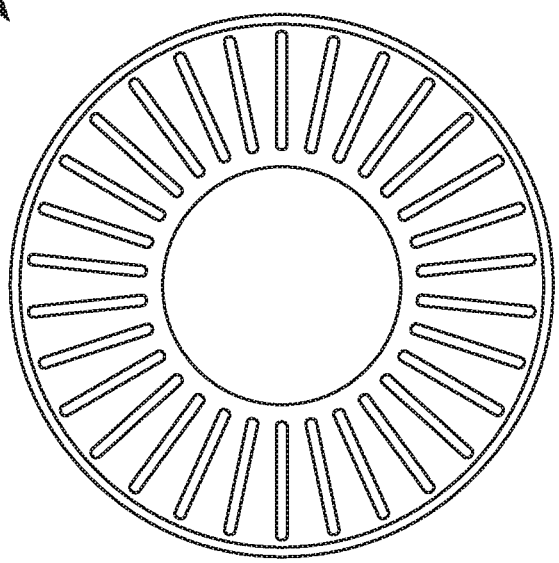
FIG. 5J is a perspective view of a serrated washer for use with the embodiment shown in FIG. 5H.
Figure 5K:
FIG. 5K is a sectional side elevation view of the washer shown in FIG. 5J.
Figures 6A, 6B:
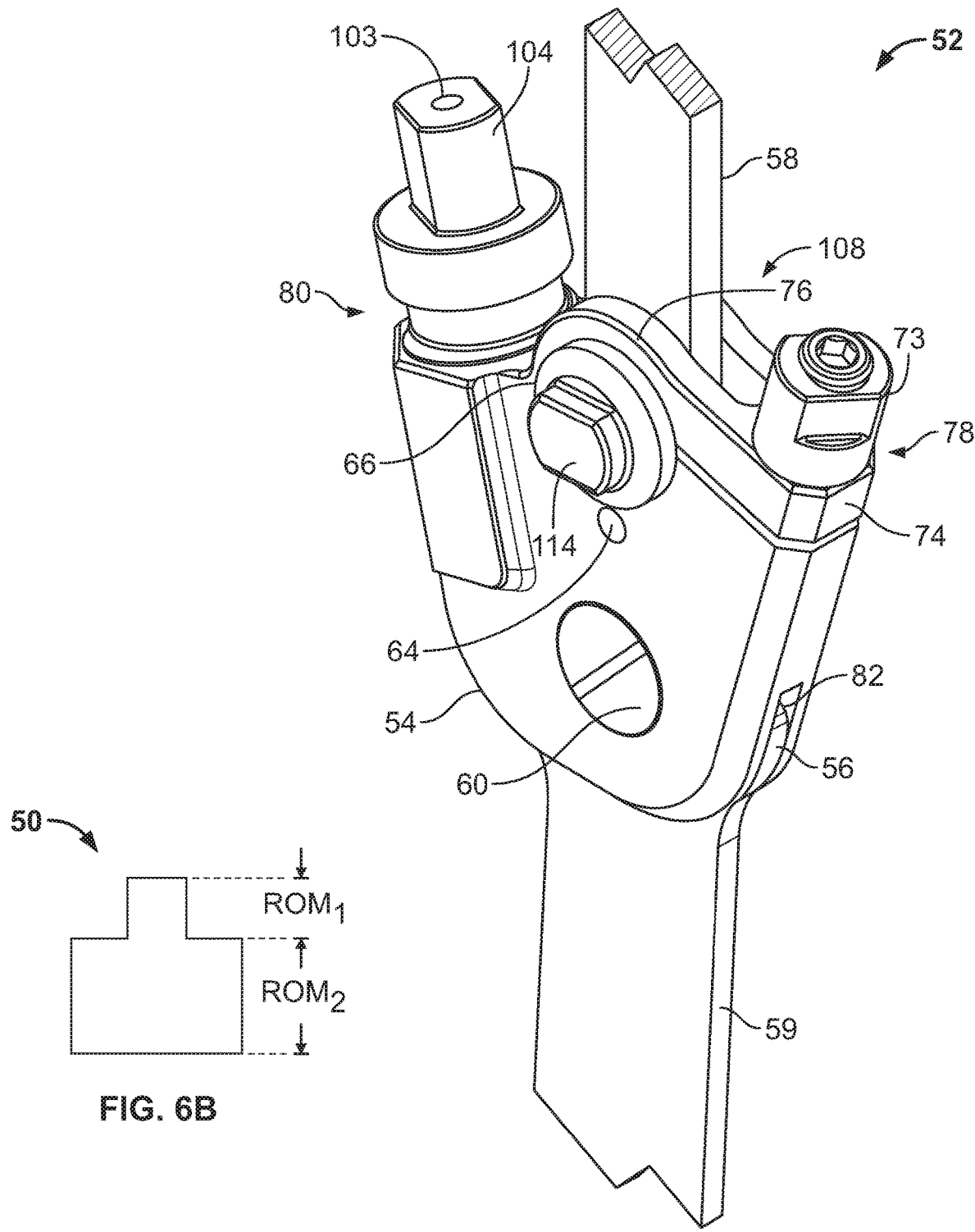
FIG. 6A is a perspective view of an ankle joint device according to an embodiment of the invention.
FIG. 6B is a schematic representation of a staged or compound dorsiflexion resistance spring for use in an ankle joint device according to an aspect of the invention.

Turning to FIG. 5H, locking cam alignment device 27" includes a cam bushing 45" having a generally cylindrical retained surface, inserted into a generally cylindrical bore 67" of a joint body 31". A pair of jaw pins 71", driven by cam locking screw 75 in the same manner as previously described, include convex (exterior) frustoconical segment engagement surfaces 91", received in a locking groove 99 having a complementary concave (interior) frustoconical engaged surface. Engagement surfaces 91" and the engaged surface of groove 99 are tapered outwardly in a proximal-to-distal axial direction extending from a proximal end of bore 67", in which cam bushing 45" is configured to be inserted, to a distal end of bore 67" at an opposite side of joint body 31" where a limb segment attachment member or other member to be aligned (not shown) may connect to a cam pin or other connecting feature on a distal end (truncated) of cam bushing 45". Thus, when jaw pins 71" are driven outwardly, their engagement with groove 99 wedges cam bushing 45" forward to clamp a washer 97 between an annular proximal flange 101 of cam bushing 45" and a proximal face of joint body 31". This axial clamping of washer 97 produces friction that further resists rotation of cam bushing 45" relative to joint body 31". Washer 97 may, for example, be a splined or serrated locking washer as shown in FIGS. 5J and 5K, to enhance its frictional locking action.

Turning to FIG. 5I, a locking cam alignment device 27''' includes a retained surface of a cam bushing 45''' and a retention surface of a bore 67''' formed in a joint body 31''' that are each frustoconical, being generally tapered inwardly in a forward, proximal-to-distal axial direction. An outwardly tapered locking groove 99' similar to locking groove 99 is formed in bore 67". Groove 99' receives jaw pins 71''' having outwardly tapered frustoconical segment engagement surfaces 91'''. Thus, when jaw pins 71''' are engaged and driven radially outwardly by cam locking screw 75, cam bushing 45''' is driven in the forward axial direction in the same manner as cam bushing 45". However, cam bushing 45''' does not require a proximal annular flange to produce axial clamping, as the retained surface of cam bushing 45" itself is inclined obliquely to the axial direction, so as to be axially clamped against the similarly oblique retention surface of bore 67'''.

According to a method of using alignment device 10, 27, 27', 27", or 27''', a human user, such as a wearer of alignment device 10 or double-action ankle joint 25, or a therapist, loosens locking nut 42 or cam locking screw 75 to permit rotation of cam bushing 22 or 45 relative to first joint member 12 or joint body 31 and revolution of eccentric cam pin 32 or 47, manually grasps joint members 12 and 14, or attachment member 29 and joint body 31, and adjusts them to a desired alignment angle as cam bushing 22 or 45 rotates and cam pin 32 or 47 revolves about the axis of cam bushing 22 or 45 and slides in cam slot 30 or 57. Once joint members 12 and 14, or attachment member 29 and joint body 31, reach the desired alignment angle, the human user tightens nut 42 or cam locking screw 75 to prevent rotation of cam bushing 22 or 45, thereby locking joint members 12 and 14, or attachment member 29 and joint body 31, at the desired alignment angle.

Staged-Resistance Orthotic Joint Devices and Methods

Orthotic joint devices and therapeutic and adaptive methods of treating biomechanical deficits according to the invention will now be described, with reference to features and embodiments illustrated in the accompanying drawings. Orthotic joint devices as described in this section provide staged resistance to angular movement of a first joint member relative to a joint body, applied in distinct phases of said movement. In the illustrated embodiments, these orthotic joint devices are shown also to incorporate orthotic joint alignment devices for adjusting the fixed alignment angle of a second joint member (namely, an upper bar) relative to a joint body. These orthotic joint alignment devices are embodiments of an aspect of the invention described in the preceding paragraphs. Other means of adjusting a fixed alignment angle between a first joint member and a joint body, whether within or outside the scope of the orthotic joint alignment device aspect of the invention, may alternatively be advantageously employed in conjunction with joint devices according to the staged resistance orthotic joint device aspect of the invention. In addition, certain benefits and advantages of the staged-resistance orthotic joint devices and methods would be retained in alternative devices in which a second joint member is integral to a joint body, or otherwise not angularly adjustable relative to a joint body.

The illustrated devices and methods provide plantarflexion ("PF") resistance by way of a PF-resist spring producing a force that limits foot slap in the wearer, but which is not so stiff as to cause the wearer to excessively flex the knee—to compensate for reduced plantarflexion—in rotating the foot forward to bring the ball of the foot into contact with the ground after heel strike. Dorsiflexion ("DF") resistance is likewise provided by a DF-resist spring. In the illustrated embodiments, the PF-resist and DF-resist springs are linear compression springs. However, the invention is not limited to devices using springs that deflect rectilinearly or in compression, or for that matter to solid state springs. A more general discussion of resistive elements within the scope of the invention is included later.

The illustrated devices and methods provide a step up in mid- to late-stance dorsiflexion resistance, to improve stance control in a wearer with a knee extensor insufficiency. The relationship between dorsiflexion and a knee extension is as follows: When the foot is planted, dorsiflexion of the foot entails pivoting the lower leg forward. In response, the knee tends to flex to keep the body's center of mass over the planted foot. Thus, the more the foot dorsiflexes in late stance, the more the knee must flex to maintain stability. In turn, the more the knee flexes, the harder the knee extensor has to work to support one's weight. Accordingly, limiting maximum dorsiflexion can reduce the heaviest torque loads on a knee extensor. Likewise, sudden onset of heavy knee extensor loading can be prevented by slowing the rate of ankle dorsiflexion in late stance. Thus, according to the present invention, a wearer's actual maximum dorsiflexion and/or the rate at which that maximum dorsiflexion is approached are limited by increasing the resistance to dorsiflexion as the dorsiflexion angle approaches the angle of maximum dorsiflexion, corresponding to a "terminal stance" state or position of the wearer's gait. The increase in resistance is preferably an abrupt stepwise increase, occurring at a desired dorsiflexion angle near the dorsiflexion angle corresponding to terminal stance.

The stepwise increase in resistance may be produced by "recruiting" a second, stiffer terminal stance DF-resist spring at a terminal stance spring recruitment angle, as in the illustrated embodiments. Alternatively, an initial (or "second rocker") DF-resist spring and a terminal stance DF-resist spring may be the same spring, such as a compound or staged DF-resist spring 50, represented schematically in FIG. 6B. Spring 50 exhibits a lower first spring rate over an initial range of deflection $ROM_1$ and abruptly transitioning to a higher second spring rate over a subsequent range of deflection $ROM_2$. The transition in spring rates is depicted schematically as a width increase, but spring 50 is not necessarily physically wider over some stiffer portion of its length. Instead, for example, it may be a coil spring that transitions to a heavier gauge or stiffer material at some point, two blocks of different compressible materials of different compression rates joined together, or some other combination of two joined sections of approximately the same width, the step up in resistance being provided by one of the sections being compressed to an effective maximum limit, such as in a coil spring compressed until the gaps between successive coils close. Alternatively, the structure of spring 50 may be essentially uniform along its entire length, the step up in resistance (such as a spring rate, which is expressed in force/distance units such as lbf/in) being provided by the entire spring being compressed to the limit of one mode of compression and another mode begins to dominate the behavior of the spring, such as when longitudinal gaps or voids are closed, and solid material begins to deform by compressing longitudinally and expanding transversely, for example. Regardless of whether a single compound or staged spring or two separate DF-resist springs is/are employed as the initial and terminal stance springs, the term "recruitment angle" will be understood to refer to an angle at which a spring or a mode of deformation or deflection becomes the dominant spring or dominant mode. For example, an angle at which a stiffer (higher spring rate) spring/mode and a softer (lower spring rate) spring/mode are simultaneously engaged in series, or only the softer spring/mode is engaged, is referred to herein as the recruitment angle of the softer spring. On the other hand, an angle at which the two springs/modes are engaged in parallel, or only the stiffer spring/mode is engaged, is referred to as the recruitment angle of the stiffer spring/mode. Thus, in the case of a compound or staged spring 50 serving as both the initial DF-resist spring and the terminal stance DF-resist spring, the "initial DF-resist spring recruitment angle" refers to the angle at which spring 50 begins to be compressed, and the "terminal stance spring recruitment angle" refers to the angle at which the softer mode of deflection essentially ceases to operate and the stiffer mode of deflection abruptly becomes dominant.

In addition to providing resistance to plantarflexion over an active plantarflexion range and two distinct phases of resistance over an active dorsiflexion range, devices according to the invention permit several parameters to be adjusted independently. These include dorsiflexion and plantarflexion resistance preloads, range of permitted dorsiflexion motion from sagittal alignment, range of permitted plantarflexion motion from sagittal alignment, and the angle in the sagittal plane between a lower leg attachment member (such as a lower leg splint, also termed a "tibial shank", or a socket or other structure into which a lower leg splint/tibial shank may be inserted, and which will move together with the lower leg splint/tibial shank) and a foot attachment member (one or the other of the attachment members, typically the foot attachment member, typically comprising a stirrup component) at a neutral position of the foot attachment member from which it is not biased in either direction.

As the lower leg attachment member is affixed to the wearer's lower leg and the foot attachment member is affixed to the wearer's foot, the angle between the splint mounting and stirrup defines a neutral or equilibrium ankle alignment angle between the wearer's lower leg and foot, in the sagittal plane. In the embodiments described below, this angle is referred to as a "tibial shank angle," with reference to the structure of the device. The neutral sagittal tibial shank angle will be understood to be the same angle as the "(equilibrium/neutral) ankle alignment angle" or simply "alignment angle" of the device. The neutral sagittal tibial shank angle is the angle by which the upper bar is displaced from its vertical orientation when the foot attachment member is in a neutral position and the wearer's foot is horizontal (planted). To facilitate measuring and adjusting the neutral sagittal tibial shank angle, the vertical orientation of the upper bar may be marked by a vertical line or notch on the joint body, provided that, as in the illustrated embodiments, the orientation of the joint body relative to the neutral position of the foot attachment member does not change with any adjustments to the device.

The scope of the invention is not limited to devices in which the reference structure affixed to a wearer's lower leg is a bar or shank. Likewise, any suitable leg retention structure may be secured directly to a wearer's lower leg and connected to the lower leg attachment member. Ankle joint devices according to the invention are suitable for use in any orthosis comprised of body mounted segments that exert control across the ankle joint, including, but not limited to, ankle-foot orthoses ("AFOs"), knee-ankle-foot orthoses ("KAFOs"), and hip-knee-ankle-foot orthoses ("HKAFOs"), typically fabricated using metal and other materials including, but not limited to, leather, polymer, filled polymer, and composite materials. In addition, though not shown in any illustrated embodiment, the device may alternatively be inverted so that the upper/leg attachment member is the member that pivots under resistance torque loads relative to the joint body with flexion of a wearer's foot, while the lower/foot attachment member is the member that is adjustably locked at a selected angle relative to the joint body.

First Illustrated Staged Resistance Joint Device Embodiment

A first illustrated embodiment of an orthotic ankle joint device according to the invention is shown as ankle joint device 52 in FIGS. 6A-15B, and an alternative embodiment is shown as ankle joint device 116 in FIGS. 16-24. Referring to FIGS. 6A-15B, ankle joint device 52 includes a joint body 54 pivotally connected to a normal contact stirrup head 56 and to an upper bar 58 that may serve as a lower leg splint mounting bar or tibial shank. Stirrup head 56, typically formed in the upper end of a lower bar 59 (also commonly termed a "stirrup") attachable to a foot orthotic or other similar structure constraining it to pivot in tandem with plantarflexion and dorsiflexion of the wearer's foot, is pivotally mounted to joint body 54 by a stirrup bushing screw 60 connected to a stirrup bushing 62, shown in FIG. 8. Similarly, upper bar 58 is pivotally mounted to an upper bar pivot pin 64. For convenience, the terms "active/relative PF/DF ROM" or "active/relative PF/DF angle" are used herein to mean an angular range of motion or angle of a foot attached component (such as stirrup head 56) relative to a sagittal neutral alignment angle in a PF or DF direction. In addition, "absolute PF/DF ROM" and "absolute PF/DF angle" are used to refer to an angular range of motion or angle of stirrup head 56 relative to upper bar 58—typically affixed to a wearer's leg and thus providing an absolute reference to its angular position—in a PF or DF direction. Additionally, a "second rocker ROM" refers to a range of motion in dorsiflexion from the sagittal neutral alignment angle to a recruitment angle of a terminal stance spring, which generally provides a step up in torque response to further dorsiflexion movement from the terminal stance spring recruitment angle. "Second rocker ROM" is not to be confused with an entire range of dorsiflexion motion permitted by the device. Indeed, a "hard stop" to dorsiflexion, such as may be formed of a solid piece of stainless steel or other generally incompressible material, is not typically necessary according to the invention, as the terminal stance spring is designed to provide a very stiff torque response, typically capable of resisting dorsiflexion torques of the magnitude produced by a wearer's gait when approaching terminal stance, without fully compressing the terminal stance spring. Thus, an entire active DF ROM could vary noticeably from wearer to wearer depending on the amount of dorsiflexion torque applied by the wearer in the third rocker/terminal stance phase.

A tibial shank angle adjustment cam 66 mated to a tibial shank angle adjustment cam bushing 68 is mounted in joint body 54 for rotation relative to joint body 54 when upper bar 58 is rotated relative to joint body 54 within a permitted adjustable range of tibial shank angles. An upper bar pocket cap 69 serves as a bushing for upper bar pivot pin 64 and as a seat for tibial shank angle adjustment cam bushing 68. Optionally, a visual tibial shank angle indicator feature 70 of tibial shank angle adjustment cam 66 cooperates with a scale 72 of joint body 54 to indicate a current tibial shank angle. In addition, tibial shank angle adjustment cam 66 and bushing 68 serve to facilitate locking the angular position of upper bar 58 by tightening a tibial shank angle locking bolt 73 to apply a clamping force to a clamping arm 74 of a tibial shank angle locking collar 76. This arrangement illustrates one way in which an angle of upper bar 58 relative to joint body 54 in the sagittal plane (a "sagittal alignment angle") may be adjusted and locked in place independently of the dorsiflexion and plantarflexion torque responses and independently of relative PF and DF ranges of motion (ROM). Advantageously, the tibial shank angle of joint device 52 can be adjusted to address (e.g., accommodate, treat/correct, or some combination) the particular condition of a wearer without a corresponding change in the support or assistance provided by joint device 52 at a given relative PF or DF angle.

Figure 12:
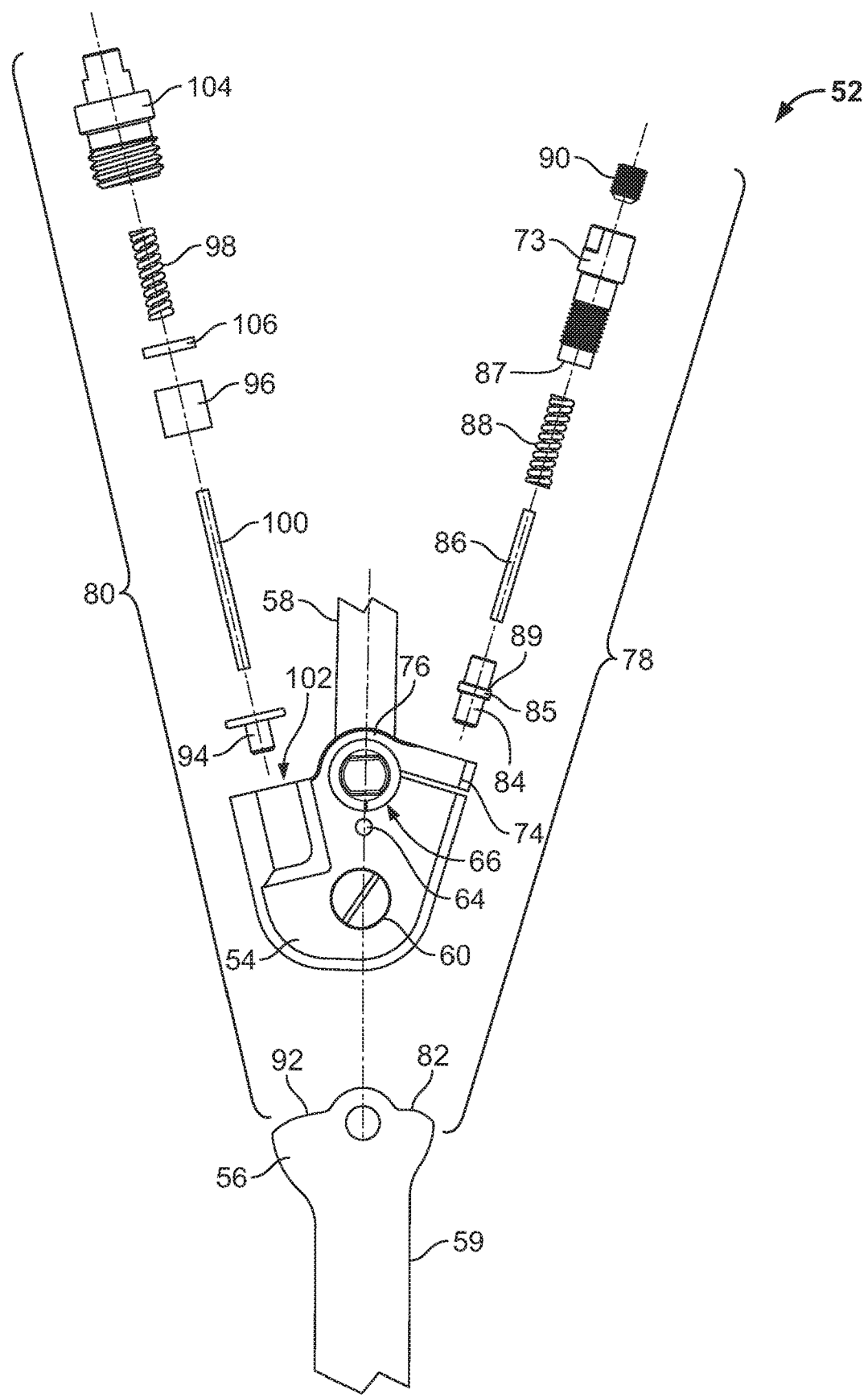
FIG. 12 is a left side exploded elevation view of the device shown in FIG. 6A.
Figure 13:
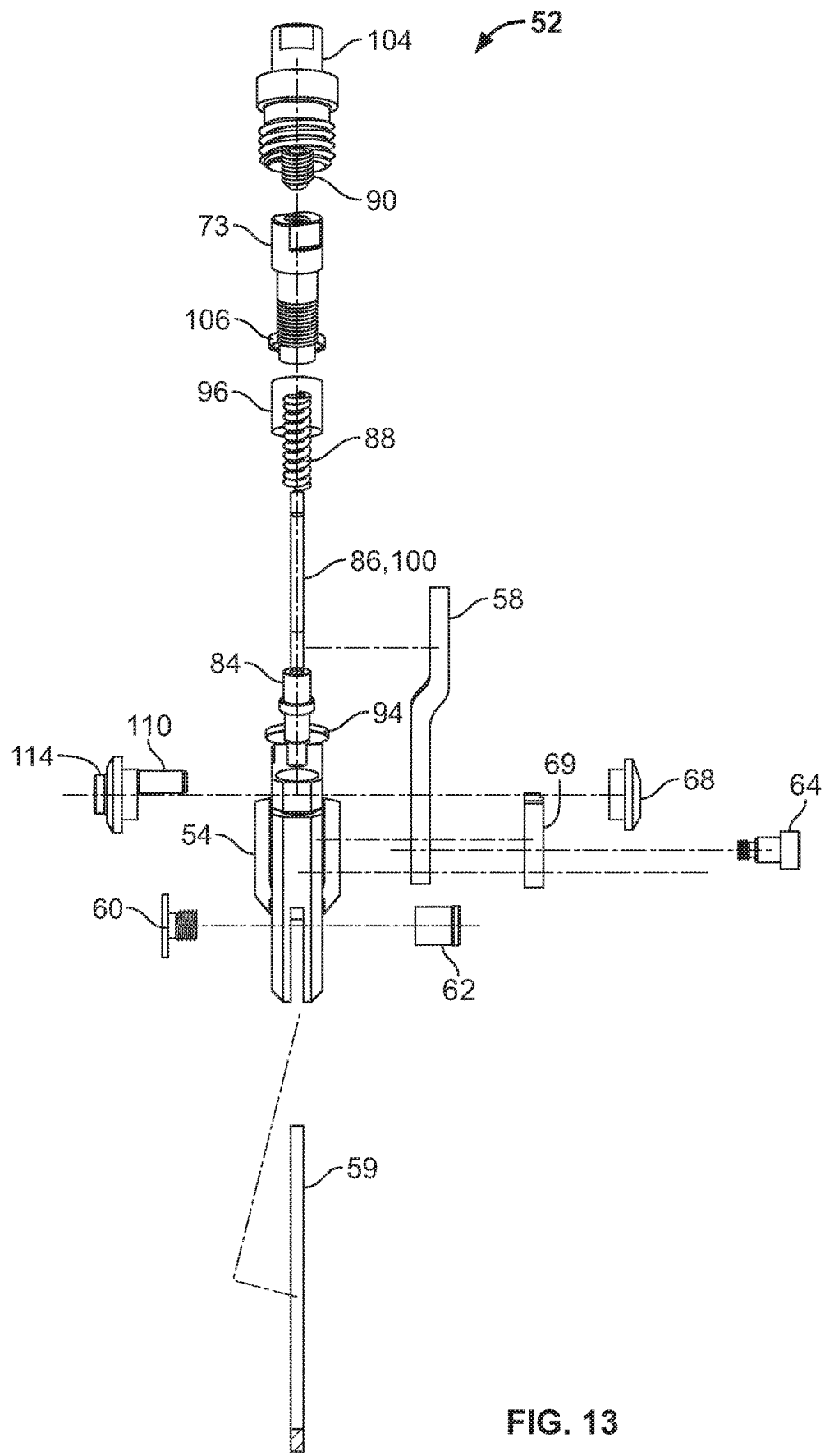
FIG. 13 is a rear exploded elevation view of the device shown in FIG. 6A.
Figure 15A:
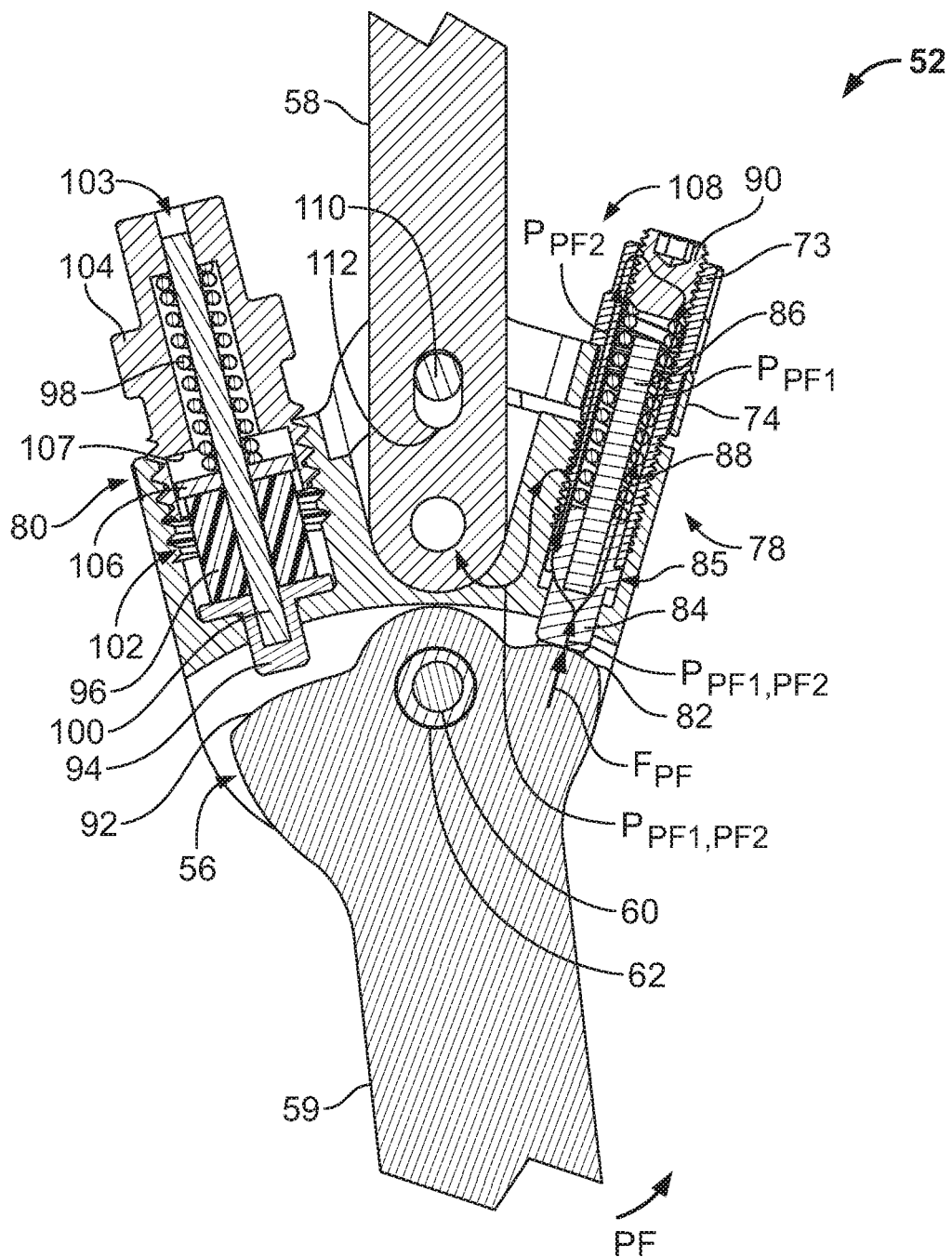
FIG. 15A is a left side sectional elevation view of the device shown in FIG. 6A, depicting an orientation of the device within an active plantarflexion range of motion.

As best seen in the exploded view of FIG. 12 and the cross sectional elevation view of FIG. 15A, ankle joint device 52 includes a PF-resist assembly 78 and a DF-resist assembly 80. During use of joint device 52 as part of an AFO or KAFO, PF-resist assembly 78 provides resistance to plantarflexion of the wearer's foot (relative to a tibial shank angle) occurring in a "first rocker phase" of a human walking gait between heel strike and midstance, corresponding to the full range of plantarflexion motion. Similarly, DF-resist assembly 80 provides resistance to dorsiflexion in a "second rocker phase" (corresponding to a first range of dorsiflexion motion) of a human walking gait between midstance and terminal stance and a "third rocker phase"/"terminal stance phase" (corresponding to a second range of dorsiflexion motion) of a human walking gait in which the wearer's foot is maximally dorsiflexed, typically until just before the wearer's heel lifts from the ground.

Plantarflexion Resistance and Range of Motion

Figure 14:
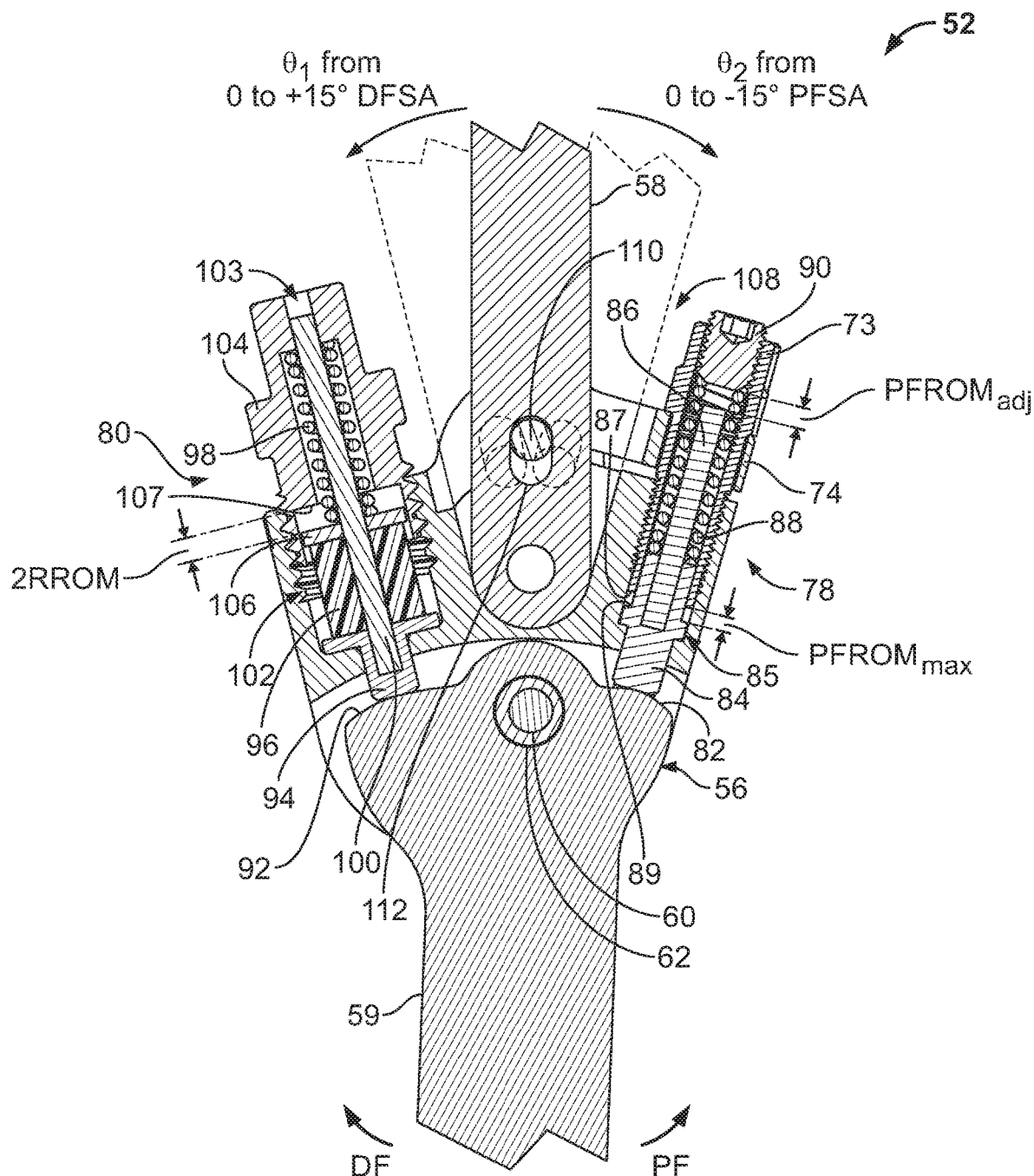
FIG. 14 is a left side sectional elevation view of the device shown in FIG. 6A.

PF-resist assembly 78 includes a PF-resist cam surface 82 and a PF-resist follower pin 84 slidingly housed in a PF-resist channel 83 formed in joint body 54, engaged by normal contact with PF-resist cam surface 82 in plantarflexion. Follower pin 84 includes a collar 85 with a lower annular end face 79 (seen in FIG. 15A) that abuts or "bottoms out" against a generally upwardly facing annular bottom surface 81 (seen in FIG. 15A) of channel 83 to provide a fixed lower stop position of pin 84, as illustrated in FIGS. 14 and 15A. In addition, assembly 78 includes a PF range of motion ("ROM") limiter pin 86 inserted through a first rocker/PF-resist spring 88; tibial shank angle locking bolt 73, which slides over PF-resist spring 88; and a PF ROM set screw 90 threaded into locking bolt 73.

PF-resist channel bottom surface 81 limits the downward excursion of pin 84 so that pin 84 ceases to transmit a PF-resist biasing force to PF-resist cam surface 82 at the equilibrium angle of lower bar 59 shown in FIG. 14, and cam surface 82 loses contact with pin 84 when pivoted from the equilibrium angle in a dorsiflexion direction. Throughout the embodiments illustrated herein, a similar arrangement of a pin or ball bearing having a limited excursion in or from a channel in which it is housed is employed to isolate the lower bar from PF-resist torques (both preload and variable) when outside the active PF-resist range of angular motion, and from DF-resist torques (both preload and variable) when outside the active DF-resist range of angular motion. In addition, in the illustrated embodiments, the components are sized, shaped, and arranged so that the respective DF-resist and PF-resist active ranges of motion cannot overlap, because the PF-resist cam follower member bottoms out in its channel just before the DF-resist cam surface of the lower bar/stirrup begins to displace the DF-resist cam follower member, and likewise, the DF-resist cam follower member bottoms out in its channel just before the PF-resist cam surface of the lower bar/stirrup begins to displace the PF-resist cam follower member. Thus, the stirrup is in flush contact with both follower members in its neutral position, but at the same time isolated from biasing forces transmitted by either cam follower member until it begins to move in one direction or the other. Advantageously, this permits DF-resist adjustments (such as preload or ROM) to be made without affecting PF-resist adjustments, and vice versa, while at the same time avoiding any play in the joint between the active DF- and PF-resist ranges, thus assisting the wearer with midstance stability. In the event that some play is desired for a particular purpose or a particular individual wearer, this could be achieved, for example, by shortening the protruding portion of one or both follower members, or by receding one or both cam profiles of the stirrup, relative to those of the illustrated embodiments. Finally, it should be noted that isolating the lower bar from DF- and PF-resist forces outside of the respective desired ranges may be achieved in other ways without departing from the scope of the invention. For example, instead of an intervening rigid component (i.e., a follower/force transmission member), a portion of a spring/resistive element may be configured to contact part of the lower bar, subject to a fixed limitation on its movement toward the contacted part of the lower bar. Moreover, in the absence of preload, a "fixed stop" on the displacement of the lower bar contacting component need not take the form of an abutting fixed surface as in the illustrated embodiments, but may simply be the fully relaxed position of the free end of a compression spring having an opposite end fixed to the joint body, or of a rigid body that is fixedly attached to an end of a fully relaxed compression spring having an opposite end attached to the joint body. Thus, the term "fixed stop" will be understood as encompassing such a relaxed free end arrangement, and not only arrangements involving abutment against a fixed surface or other form of "stop member." In addition, the displacement path of whatever component contacts the lower bar need not be purely translational; it may instead be purely rotational or include both translation and rotation.

PF ROM set screw 90 serves to define an adjustable plantarflexion range of motion as a clearance between PF ROM limiter pin 86 and a selected "fixed" position of set screw 90, "fixed" in the sense that, though adjustable by turning, it is essentially immovable by linear forces transmitted from PF-resist spring 88. In addition to adjusting plantarflexion range of motion, PF ROM set screw 90 also serves to adjust the preload applied to PF-resist spring 88, as PF ROM limiter pin 86 and spring 88 are disposed in parallel between PF-resist follower pin 84 and PF ROM set screw 90. Thus, advancing PF ROM set screw 90 increases the preload of PF-resist spring 88 and reduces the range of plantarflexion pivotal movement of stirrup head 56 relative to joint body 54, while retracting PF ROM set screw 90 decreases the preload of spring 88 and increases the range of plantarflexion pivotal movement of stirrup head 56 relative to joint body 54. For a typical patient, PF-resist spring 88 may be adjusted to provide as little as 0 in-lb or as much PF-resist preload torque as can be provided by the spring through its active range. At the end of its active range and under maximum compression, the motion limiting stop exerts the maximum resistive torque bypassing the spring. Additional flexibility in torque ranges may be provided by substituting stiffer or softer springs, which is permitted in each of the illustrated embodiments by simply unscrewing a cap or adjustment/set screw.

Joint device 52 permits several additional ways of adjusting plantarflexion range of motion according to the invention. For example, the modular design of PF-resist assembly 78 advantageously permits the substitution of a longer or shorter PF ROM limiter pin for pin 86 (or if PF ROM limiter pin 86 is permanently joined to PF-resist follower pin 84 to form a single member, removal and replacement of the combined member with one having a longer or shorter ROM limiter portion corresponding to pin 86), as well as the insertion or removal of any of a plurality of spacers, such as rod-, disc-, or washer-like spacers (not shown) stacked above or below pin 86 in the interior of PF-resist spring 88. Any of the foregoing adjustments would change the angle of maximum permitted plantarflexion relative to the neutral ankle angle. Further, adding or removing one or more washers (not shown) in series with PF-resist spring 88 can compensate for a change in the preload of PF-resist spring 88 resulting from an adjustment of PF ROM set screw 90, thus providing a multistep plantarflexion range of motion adjustment independent of PF-resist preload and neutral ankle angle. Finally, in the illustrated embodiment, collar 85 abuts a lower end surface 87 of tibial shank angle locking bolt 73 at a fixed maximum range of plantarflexion motion, acting as a fallback or default plantarflexion stop member whenever PF ROM set screw 90 is retracted to a distance $PFROM_{adj}$ from the upper end face of PF ROM limiter pin 86 that is greater than a distance $PFROM_{max}$ between an upper surface 89 of collar 85 and lower end surface 87 of tibial shank angle locking bolt 73. Thus, in this embodiment, a clearance between collar 85 and lower end surface 87 serves to set a maximum limit on plantarflexion range of motion, which may, for example, permit no more than 14 degrees of plantarflexion movement from the sagittal tibial shank angle.

In addition, as will be described in more detail below, absolute plantarflexion range of motion can be adjusted by changing the tibial shank angle of upper bar 58 relative to joint body 54, i.e., by independently adjusting the equilibrium ankle alignment angle itself, without altering the kinematic relationship between stirrup head 56 and joint body 54. It should be noted that changing the equilibrium angle in this manner produces not only an absolute PF ROM adjustment, but also an equal and opposite absolute DF ROM adjustment.

Respective primary and secondary PF load paths $P_{PF1}$, $P_{PF2}$ of a plantarflexion force $F_{PF}$ from stirrup head 56 through PF-resist assembly 78 and ankle joint body 54 to upper bar 58 are illustrated in FIG. 15A. With reference to primary load path $P_{PF1}$ shown in the drawing, force $F_{PF}$ is applied by normal contact of PF-resist cam surface 82 on PF-resist follower pin 84. The shape of the contours of stirrup head 56 is configured such the direction of this normal contact is essentially aligned with an axis of PF-resist spring 88, so as to limit radial forces between joint body 54 and follower pin 84 and the resulting wear on both (and even possible component failure) through rubbing contact and bending forces, as well as limiting any unaccounted for frictional resistance associated with such rubbing contact. In addition, such axial alignment of normal contact may enhance the end constraint of PF-resist spring 88, increasing its cycle life. Force applied to PF-resist follower pin 84 is then transmitted through pin 84 to PF-resist spring 88, through PF-resist spring 88 to PF ROM set screw 90, through the threads of PF ROM set screw 90 to the inner threads of tibial shank angle locking bolt 73, through the outer threads of tibial shank angle locking bolt 73 to the inner threads of ankle joint body 54, and finally through ankle joint body 54 to upper bar 58. Until stirrup head 56 is rotated in plantarflexion to the end of its plantarflexion range of motion, substantially all of force $F_{PF}$ is transmitted via primary load path $P_{PF1}$.

However, once PF-resist follower pin 84 "bottoms out" by traversing a maximum range of motion $PFROM_{max}$ so that its collar 85 abuts tibial shank angle locking bolt 73 (as shown in FIG. 15A), or an adjustable range of motion $PFROM_{adj}$ so that PF ROM limiter pin 86 abuts PF ROM set screw 90 (not shown, but refer to FIG. 24 for an illustration of the analogous secondary load path via an ROM limiter pin in an alternative joint device embodiment), any excess force then bypasses PF-resist spring 88 via a secondary load path $P_{PF2}$, which essentially provides a hard stop preventing any further plantarflexion.

Dorsiflexion Resistance and Ranges of Motion

Figure 15B:
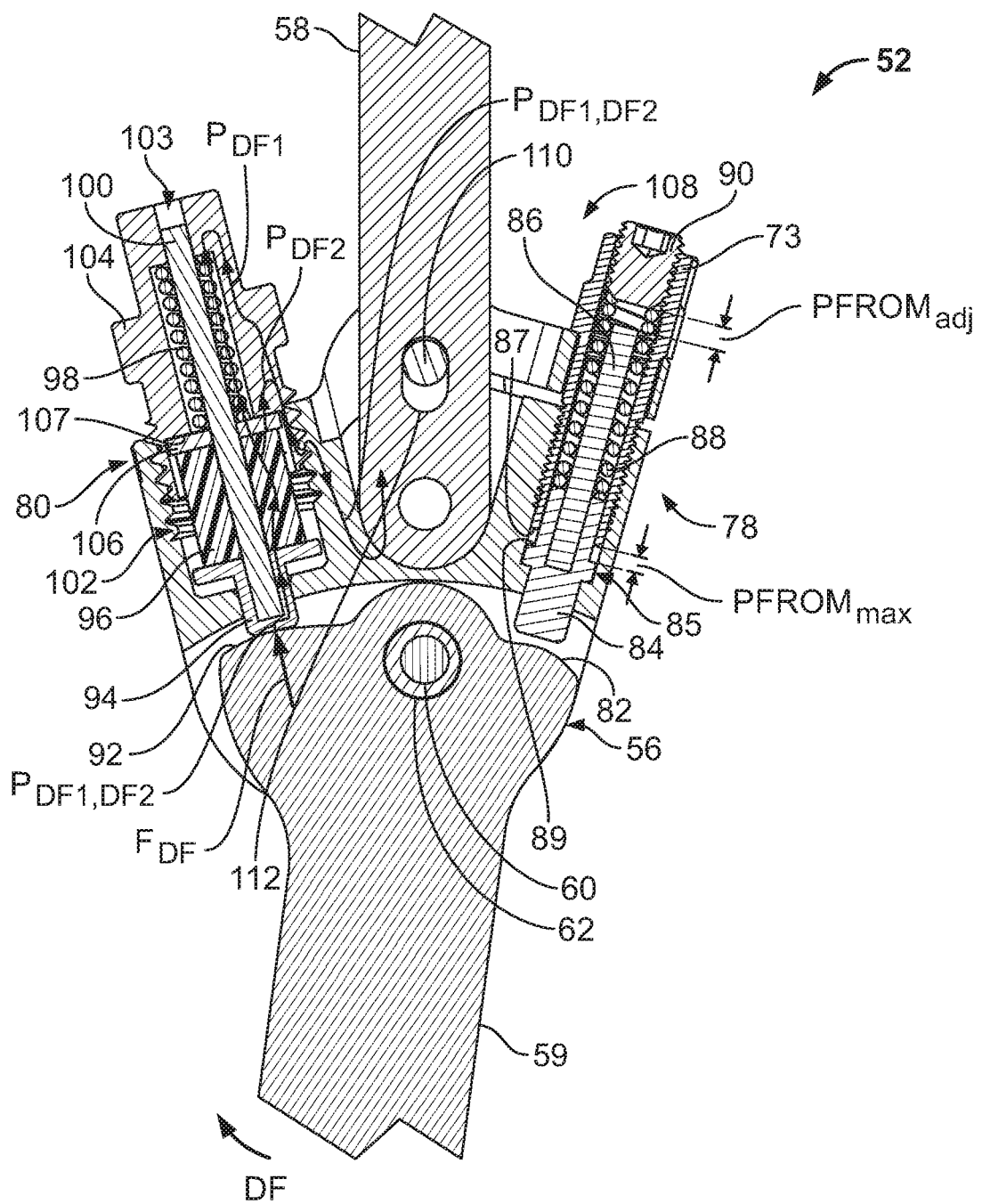
FIG. 15B is a left side sectional elevation view of the device shown in FIG. 6A, depicting an orientation of the device at a terminal stance spring recruitment angle, at the end of a second rocker range of motion and within an overall dorsiflexion range of motion.
Figure 16:
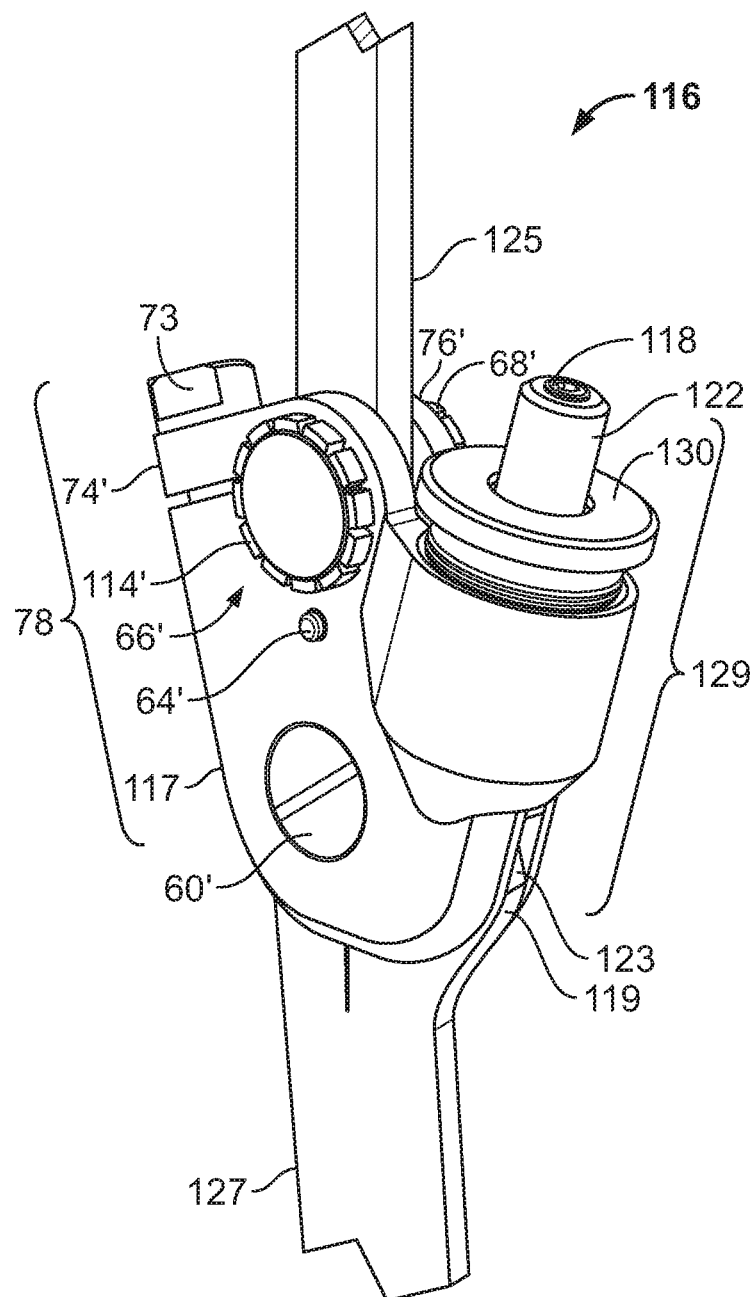
FIG. 16 is a perspective view of an ankle joint device according to another embodiment of the invention.
Figure 17:
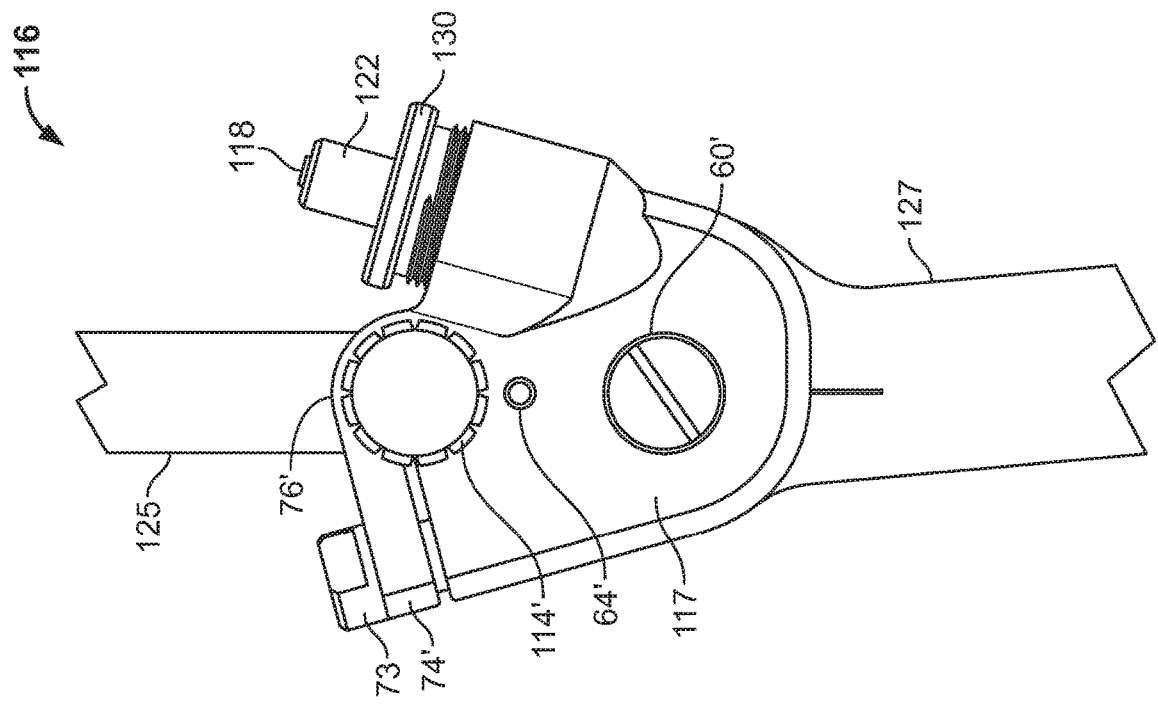
FIG. 17 is a left side elevation view of the device shown in FIG. 16.
Figure 18:
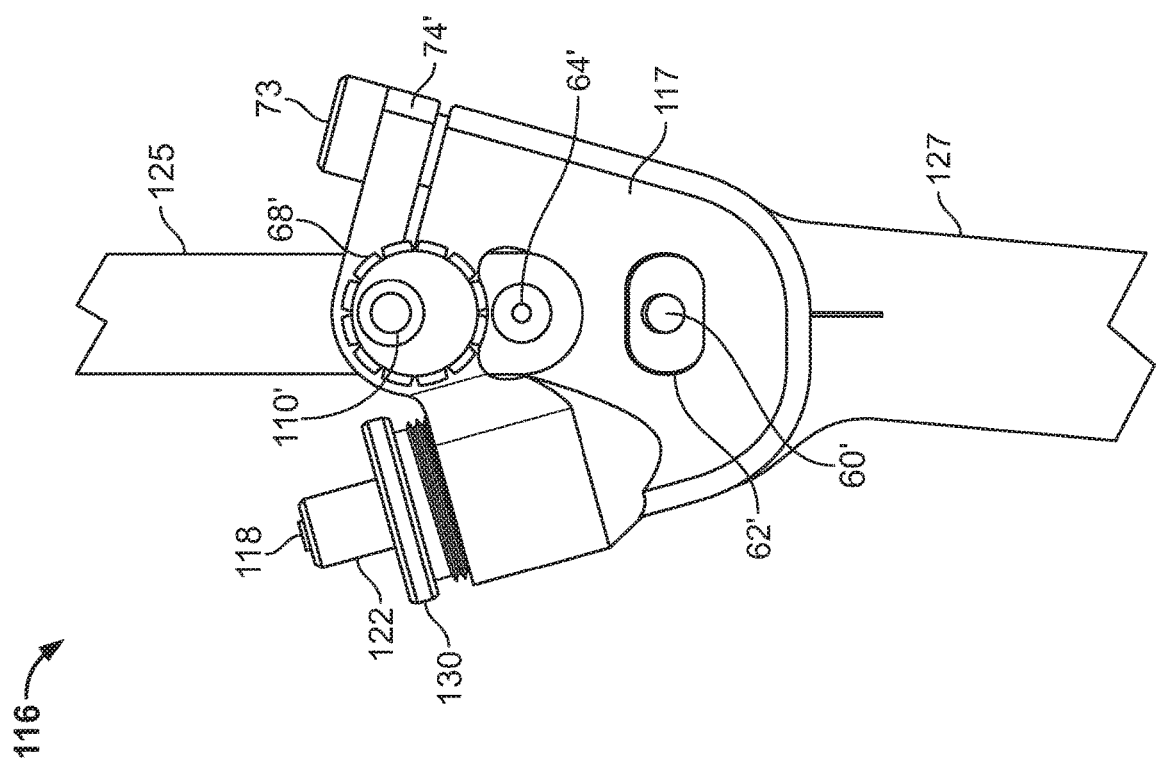
FIG. 18 is a right side elevation view of the device shown in FIG. 16.
Figure 20:
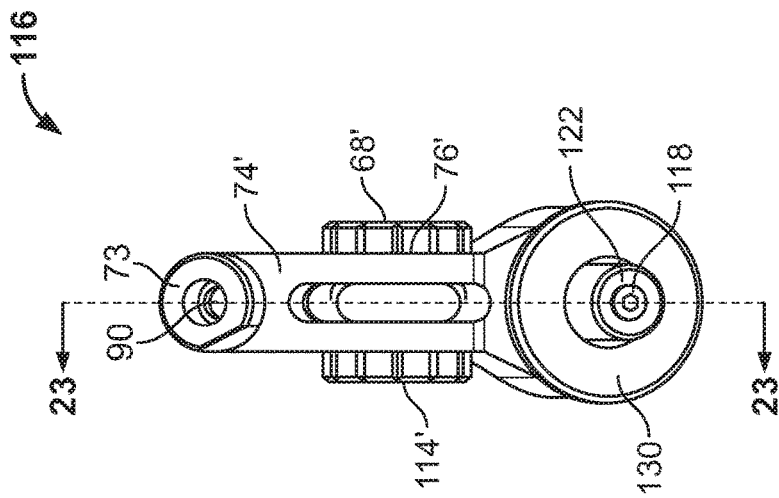
FIG. 20 is a top plan view of the device shown in FIG. 16.
Figure 19:
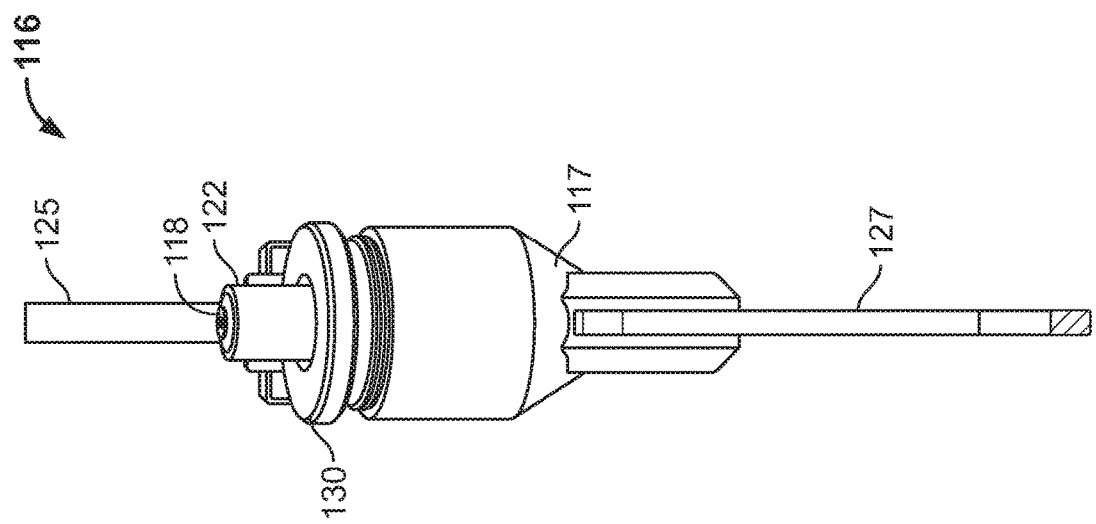
FIG. 19 is a front elevation view of the device shown in FIG. 16.
Figure 21:
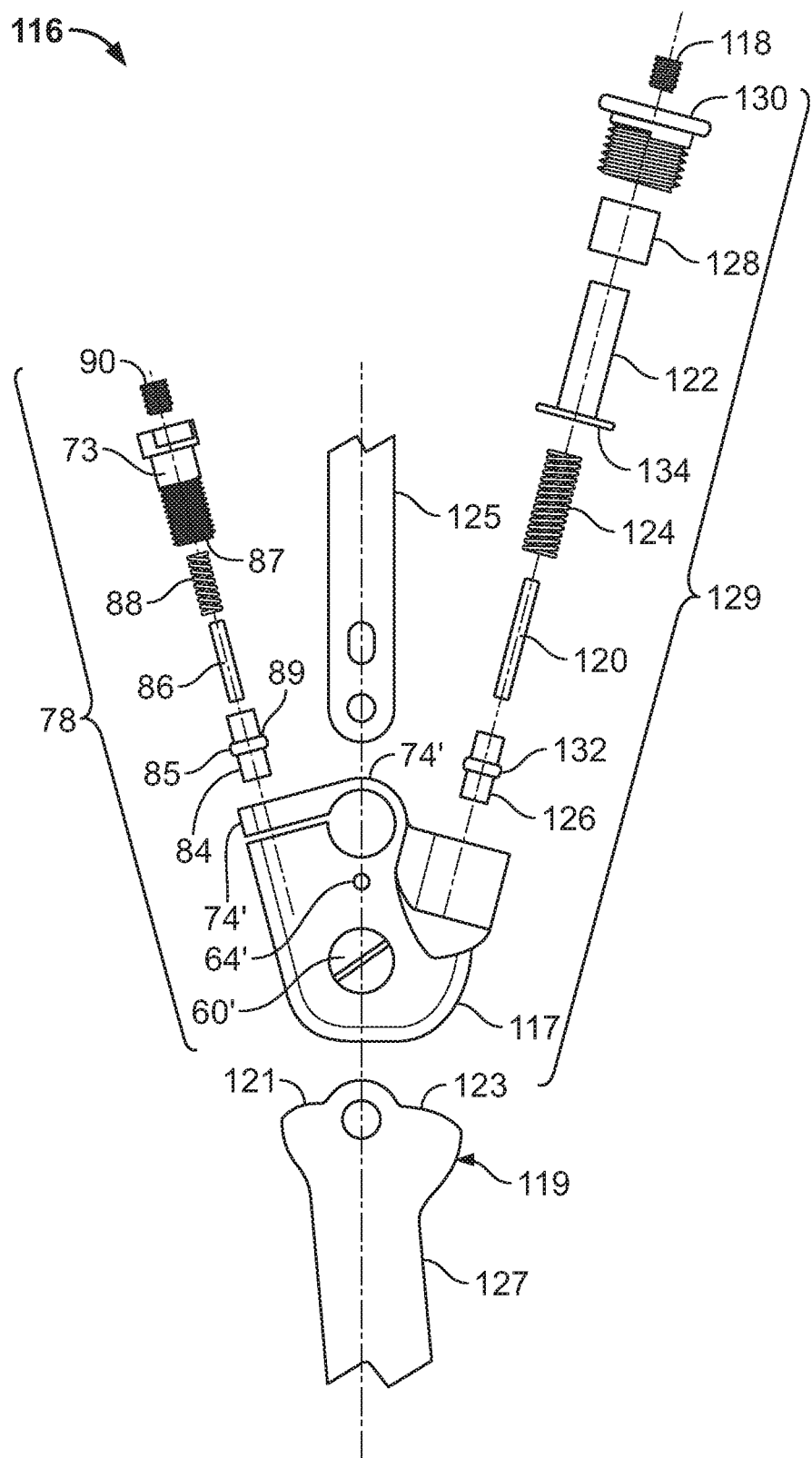
FIG. 21 is a right side exploded elevation view of the device shown in FIG. 16.
Figure 22:
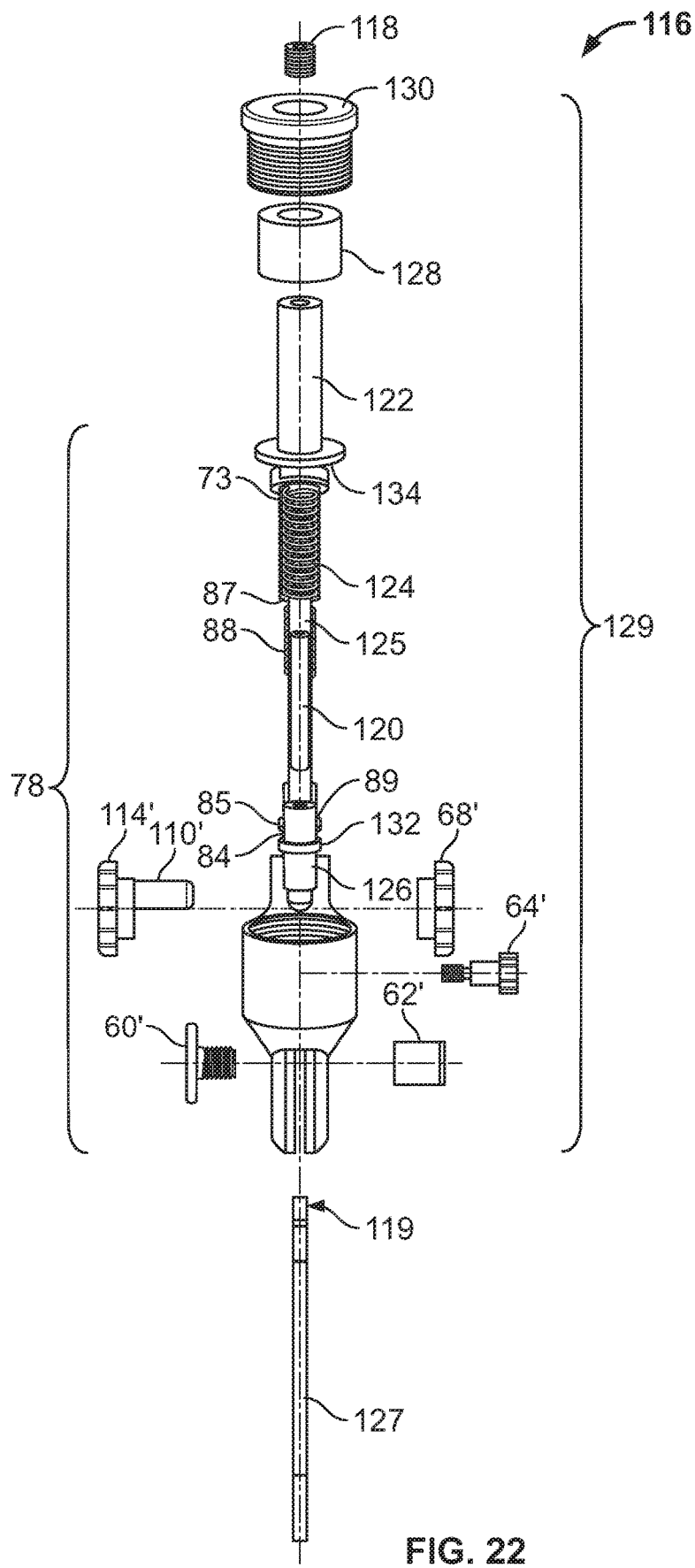
FIG. 22 is a front exploded elevation view of the device shown in FIG. 16.

DF-resist assembly 80 comprises a DF-resist cam surface 92 and a DF-resist follower pin 94 engaged by normal contact with DF-resist cam surface 92 when stirrup head 56 is pivoted past the neutral position in the dorsiflexion direction. With reference to FIGS. 14, 15A and 15B, it will be readily understood that the extent of downward excursion of a narrow lower portion of DF-resist follower pin 94 from a DF-resist channel formed in joint body 54 is limited by an annular flange portion of follower pin 94 abutting a bottom surface of the channel, in a manner similar to that described above in more detail with respect to PF-resist follower pin 84. Additionally, DF-resist assembly 80 includes a terminal stance ("TS") DF-resist spring 96 (which may also be referred to for brevity as a "terminal stance spring"); a second rocker DF-resist spring 98; and a DF-resist spring guide pin 100 extending through DF-resist springs 96 and 98 and a hole 103 in an upper end of a DF-resist cap 104; cap 104 being threaded into joint body 54. A washer 106 is shown as a spacer/coupling element between DF-resist springs 96 and 98.

Respective primary and secondary load paths through the components of DF-resist assembly 80 are best illustrated in FIG. 15B. With reference to a primary load path $P_{DF1}$ shown in the drawing, force $F_{DF}$ is applied by normal contact of DF-resist cam surface 92 on DF-resist follower pin 94 and transmitted through pin 94 to TS DF-resist spring 96, through TS DF-resist spring 96 to second rocker DF-resist spring 98, through second rocker DF-resist spring 98 to DF-resist cap 104, through the threads of DF-resist cap 104 to the threads of ankle joint body 54, and finally through joint body 54 to upper bar 58. Until stirrup head 56 is rotated in dorsiflexion to the end of its second rocker range of motion, substantially all of force $F_{DF}$ is transmitted via primary load path $P_{DF1}$. However, once TS DF-resist spring 96 traverses a second rocker ROM clearance 2RROM (shown in FIG. 14), so that a washer 106 abuts an annular lower end face 107 of DF-resist cap 104, any excess force then bypasses second rocker DF-resist spring 98 and is instead transmitted via a secondary load path $P_{DF2}$ leading directly from TS DF-resist spring 96 into DF-resist cap 104.

Analogously to PF-resist assembly 78, DF-resist assembly 80 permits adjustment of a second rocker range of motion and a preload of second rocker DF-resist spring 98 by advancing (lowering) and withdrawing (raising) DF-resist cap 104 into and out of a tapped hole 102 in ankle joint body 54. In particular, advancing DF-resist cap 104 increases second rocker preload and decreases second rocker ROM, while withdrawing DF-resist cap 104 decreases second rocker preload and increases second rocker ROM. In one preferred embodiment, an active second rocker range of motion of up to about 10° and an active terminal stance range of motion of up to about 7° are permitted, for a total active DF range of motion of up to about 17°. A second rocker DF-resist spring 98 may be adjusted to provide as little as 0 in-lb preload torque and up to a desired amount, which may depend on the wearer's weight and strength and other clinical factors.

TS DF-resist spring 96 should typically provide on the order of up to about 10 times the torque, or more if desired, of second rocker DF-resist spring 98. Thus, the wearer of joint device 52 will feel a dramatic increase in supportive resistance to dorsiflexion when it is most needed, in an uppermost range of dorsiflexion leading up to terminal stance, just before the wearer's heel lifts off the ground.

A polyurethane bushing is a compact and economical candidate to serve as TS DF-resist spring 96, being capable of providing a substantial step up in resistance without requiring a diameter so large as to impinge the wearer's leg or ankle or otherwise render the device cumbersome to wear. A significant consideration for polyurethane springs is that, at the required frequency of about 1 to 2 dorsiflexion cycles per second, the compression ratio acting on a polyurethane spring must be less than about 15% to avoid pre-set or slow recoil/response. Polyurethane springs are comparatively large as well, but not as large as comparable coil springs would be.

Analysis of required dorsiflexion resist torque, using representative values for post-CVA (cerebrovascular accident) orthotic management from the literature, suggests that even nested helical compression springs may need to be excessively large to deliver the required torque for management of knee flexion in late stance. Machined springs are likely a functionally suitable alternative to polyurethane springs, but could be prohibitively expensive. Gas springs may also be a suitable alternative resistive element.

Neutral Sagittal Tibial Shank Angle Adjustment

Figure 8:
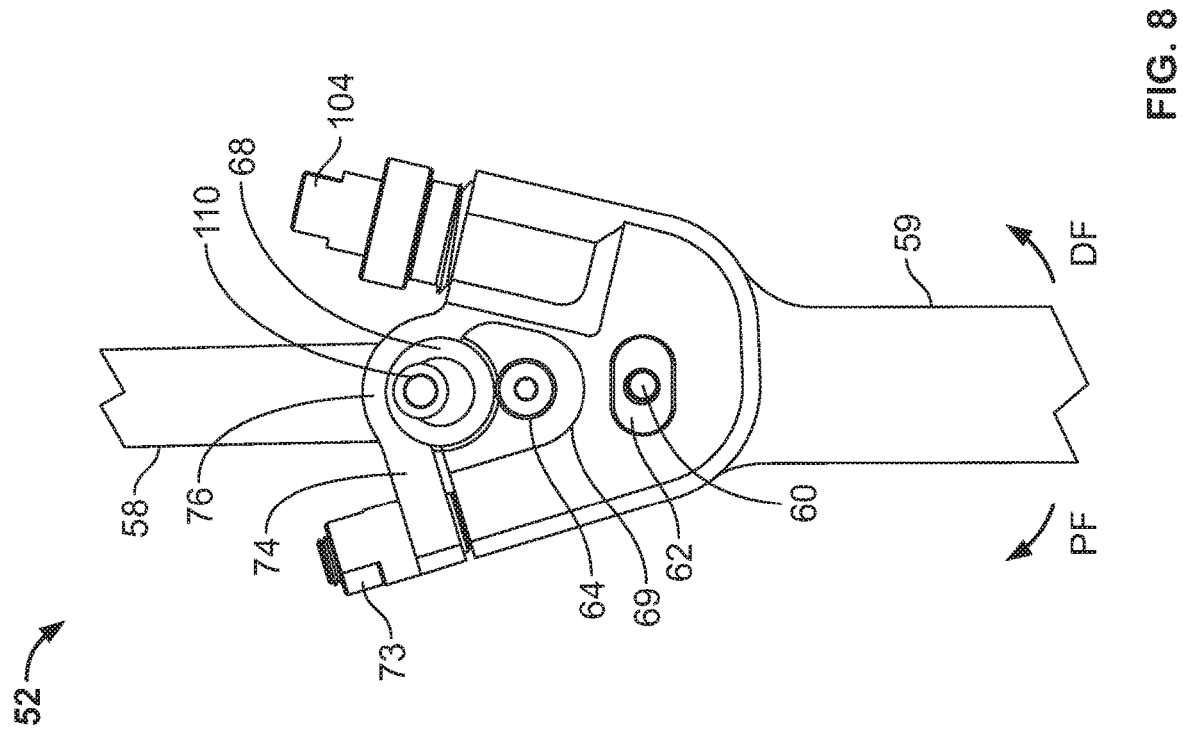
FIG. 8 is a right side elevation view of the device shown in FIG. 6A.
Figure 7:
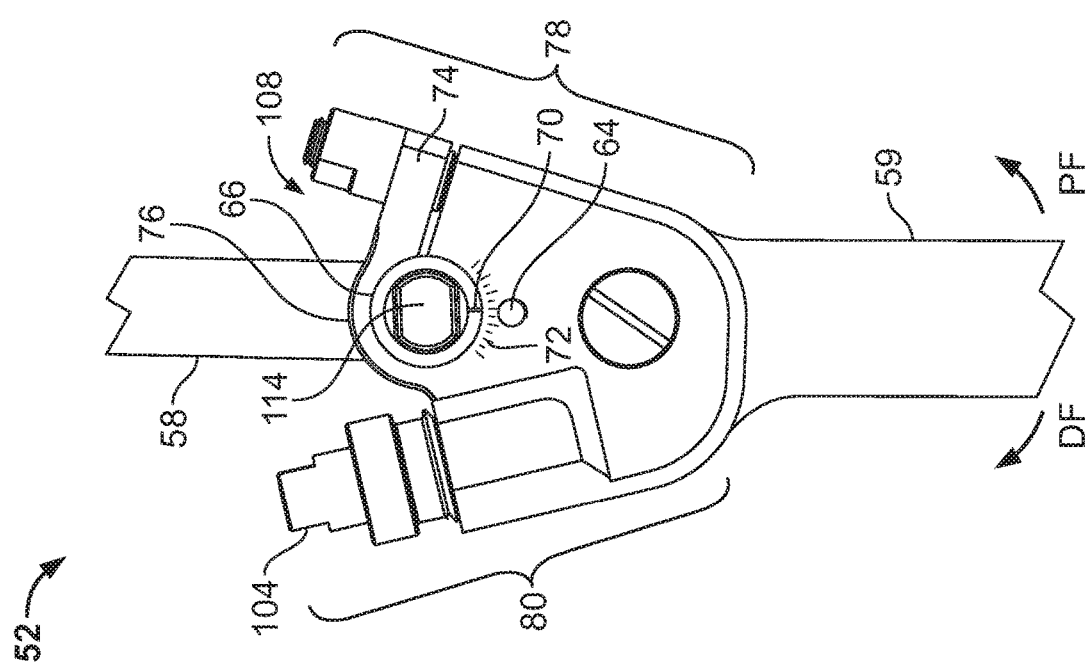
FIG. 7 is a left side elevation view of the device shown in FIG. 6A.
Figure 9:
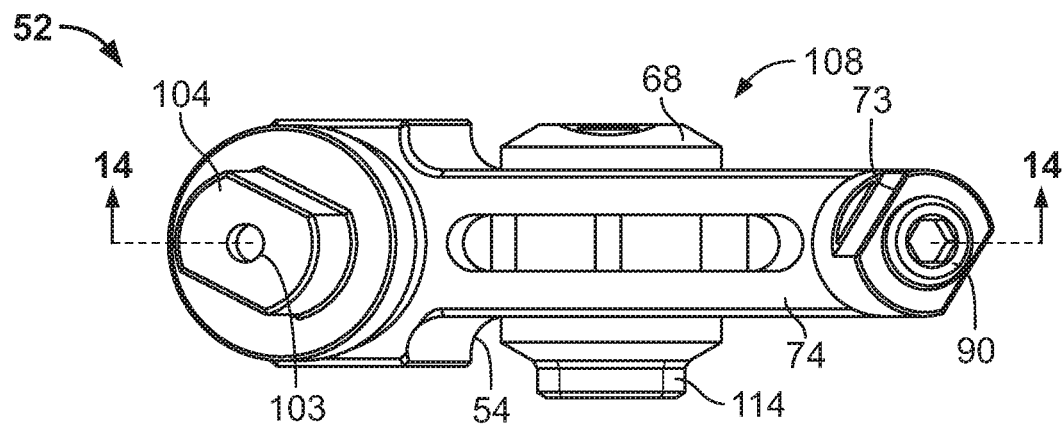
FIG. 9 is a top plan view of the device shown in FIG. 6A.
Figure 10:
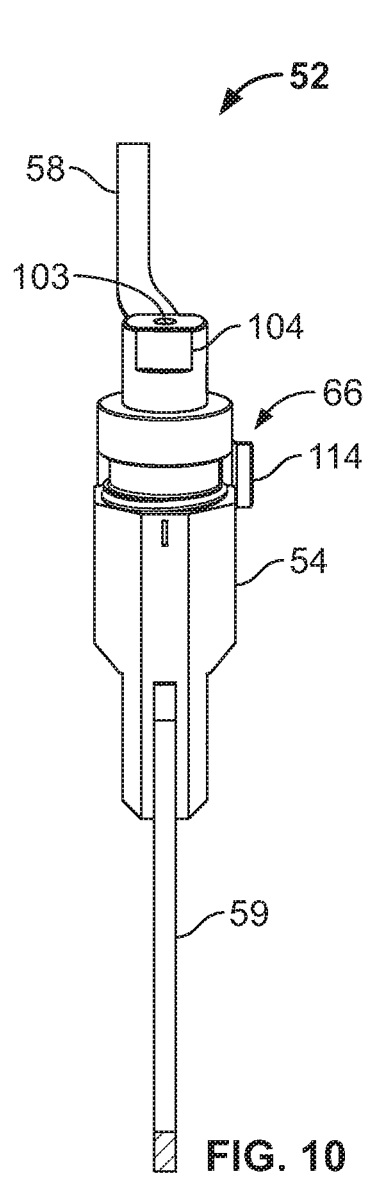
FIG. 10 is a front elevation view of the device shown in FIG. 6A.
Figure 11:
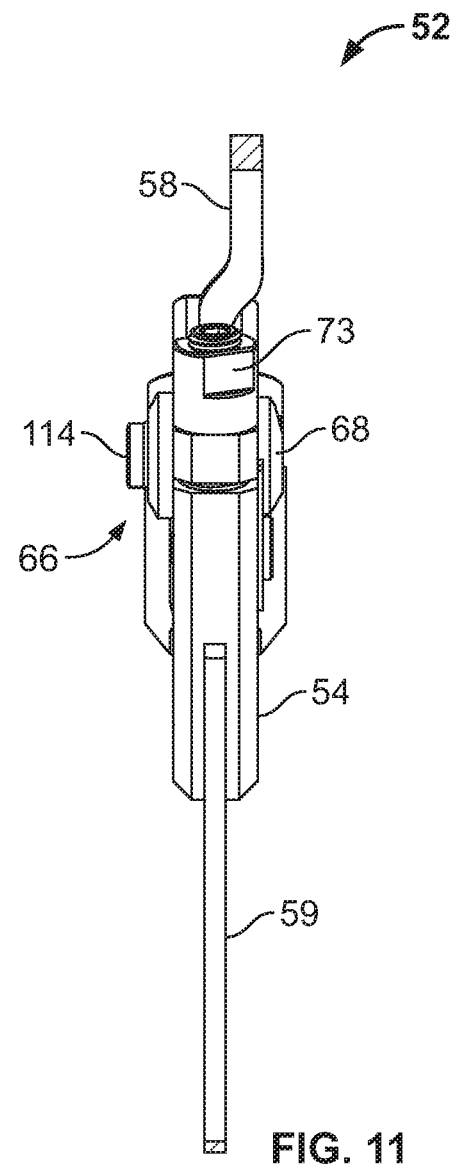
FIG. 11 is a rear elevation view of the device shown in FIG. 6A.

A tibial shank angle adjustment assembly 108 for adjusting the angle of upper bar 58 in the sagittal plane, as best illustrated in FIGS. 7, 8 and 15A, will now be described in detail. As mentioned above, tibial shank angle adjustment assembly 108 includes the aforementioned upper bar 58, upper bar pivot pin 64, tibial shank angle adjustment cam 66, tibial shank angle adjustment cam bushing 68, and tibial shank angle locking collar 76 that frictionally locks tibial shank angle adjustment cam 66 in place when tibial shank angle locking bolt 73 is tightened to apply a clamping force to clamping arm 74. With reference to FIGS. 7, 8 and 15A, tibial shank angle adjustment cam 66 includes an eccentric tibial shank angle adjustment cam pin 110 fixed at an offset radial distance from a central axis of cam 66, so as to rotate about said central axis when cam 66 rotates in place in collar 76. In addition, cam pin 110 extends through an elongate cam slot 112 in upper bar 58.

Upper bar pivot pin 64 is disposed below tibial shank angle adjustment cam 66, and when upper bar 58 is in a twelve o'clock tibial shank angle adjustment position substantially aligned with lower bar 59, cam pin 110 is also disposed at the twelve o'clock position relative to the axis of cam 66, at its highest point in slot 112, and vertically aligned with the axes of cam 66 and upper bar pivot pin 64. From this position, the rotation of tibial shank angle adjustment cam 66 initially moves easily and amplifies the rotation of pivotal upper bar 58 away from the vertical tibial shank angle position, while amplification of rotation decreases and resistance to movement increases the farther upper bar 58 is rotated from the vertical position. To reflect this changing amplification, a step interval between equally spaced apart lines of scale 72 will decrease appropriately toward the extremes of shank angle adjustment. Alternatively, the spacing between neighboring scale lines indicating equal step intervals may increase toward the extremes.

Due to the increasing resistance to rotation of cam 66 as cam pin 110 is farther displaced from the twelve-o'clock position, a wearer or therapist grasping ankle joint body 54 with one hand and upper bar 58 with the other hand may easily be able to pivot upper bar 58 away from vertical alignment without a tool, but a tool (such as a special wrench) may be desired or needed to grip and rotate a bolt head 114 of cam 66 to and from larger angles of plantarflexion and dorsiflexion. On the other hand, the increasing resistance to rotation of cam 66 approaching the extremes of equilibrium angle adjustment advantageously helps to hold upper bar 58 at an inclined sagittal angle. Increased resistance to rotation is particularly beneficial, for example, when an inclined tibial shank angle is desired for the purpose of correcting a tendency of the wearer's ankle to flex in the opposite direction from vertical alignment, and/or for the purpose of exercising or strengthening a wearer's muscles that tend to urge the foot in the opposite direction toward vertical alignment. In either case, the device may be under nearly constant stress from the wearer's foot flexing or attempting to flex in said opposite direction, even when the wearer is at rest, tending to urge upper bar 58 back toward vertical alignment, and increased resistance to rotation of cam 66 will help to prevent upper bar 58 from budging.

In one embodiment, the tibial shank angle adjustment assembly 108 permits adjustment of upper bar 58 to a dorsiflexion angle $\theta_1$, up to about +15°, or to a plantarflexion angle $\theta_2$, up to about −15°, with respect to a vertical position of upper bar 58 relative to lower bar 59, seen in FIG. 14. This range considers not only typical biomechanical variances, which are about 10° dorsiflexion and −20° plantarflexion of functional range, but also the possibility that the clinician may want to asymmetrically offset the adjustment for a clinical purpose, such as correcting a malaligned ankle posture, compensating for a contracture (either in dorsiflexion or plantarflexion), or treating a joint contracture by using joint device 52 (or any other joint device according to the invention) as an active or static progressive component.

Second Illustrated Staged Resistance Joint Device Embodiment

Turning to FIGS. 16-24, another ankle joint device 116 is illustrated. Similarly to joint device 52 described above, joint device 116 includes a joint body 117, a pivotally mounted stirrup head 119 comprising a PF-resist cam surface 121 and a DF-resist cam surface 123, an upper bar 125 generally configured for use as a lower leg splint mount, and a lower bar 127 integrally formed with stirrup head 119 and extending downwardly therefrom, lower bar 127 being configured for attachment to a foot orthosis (not shown) or otherwise constrained to pivot in accordance with a wearer's bidirectional foot flexion. An upper bar pivot pin 64', a lower bar/stirrup bushing screw 60', and a lower bar/stirrup bushing 62' function analogously to the corresponding components of joint device 52.

Plantarflexion Resistance and Range of Motion

Joint device 116 includes substantially the same PF-resist assembly 78 as joint device 52, with like components labeled as in FIGS. 6A-15B.

Dorsiflexion Resistance and Ranges of Motion

On the other hand, a DF-resist assembly 129 of joint device 116 differs somewhat in structure and function from assembly 80 of device 52. Most significantly, DF-resist assembly 129 provides a mechanism for adjusting dorsiflexion range of motion independently of second rocker preload. In particular, a second rocker ROM set screw 118 provides a hard stop to the range of motion of a second rocker ROM limiter pin 120 relative to a TS DF-resist spring hat 122. Set screw 118 and second rocker ROM limiter pin 120 fit without interference in the interior of a second rocker DF-resist spring 124, so that the second rocker range of motion is adjustable in a single step of turning set screw 118, without affecting a preload of second rocker DF-resist spring 124.

Figure 24:
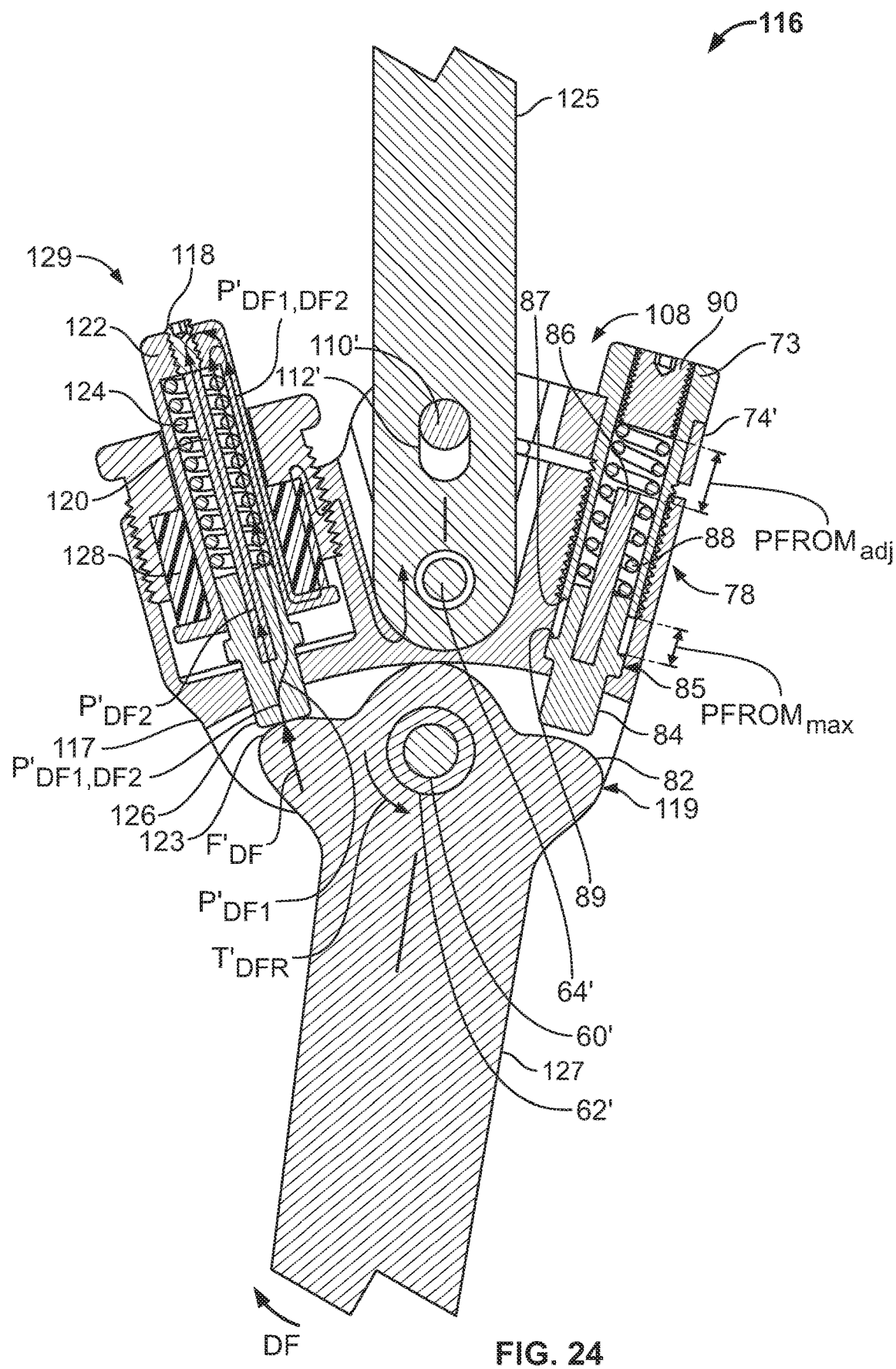
FIG. 24 is a left side sectional elevation view of the device shown in FIG. 17, depicting an orientation of the device at a terminal stance spring recruitment angle, at the end of a second rocker range of motion and within an overall dorsiflexion range of motion.

Respective primary and secondary load paths through the components of DF-resist assembly 129 of device 116 are best illustrated in FIG. 24. With reference to a primary dorsiflexion load path $P'_{DF1}$ shown in the drawing, force PDF is applied by normal contact of DF-resist cam surface 123 on a DF-resist follower pin 126 and transmitted through pin 126 to second rocker DF-resist spring 124, through second rocker DF-resist spring 124 to a TS DF-resist spring hat 122, through TS-spring hat 122 to a TS DF-resist spring 128, through TS DF-resist spring 128 to a TS-resist cap 130 that is threaded into joint body 117, through the threads of TS-resist cap 130 to the threads of ankle joint body 117, and finally through joint body 117 to upper bar 125. When stirrup head 119 begins to rotate in dorsiflexion from its neutral position (a position in which both PF-resist follower pin 84 and DF-resist follower pin 126 are bottomed out in their respective channels, isolating stirrup head 119 from their respective biasing forces, as explained in more detail with respect to the first embodiment, and until stirrup head 119 has rotated in dorsiflexion to the end of its second rocker range of motion, substantially all of force PDF is transmitted via primary load path $P'_{DF1}$.

However, once DF-resist follower pin 126 traverses an adjustable second rocker ROM clearance $2RROM'_{adj}$ so that ROM limiter pin 120 abuts second rocker ROM set screw 118, or pin 126 traverses a maximum stop clearance $2RROM'_{max}$ so that an upper face of a DF-resist follower pin collar 132 abuts an annular lower end face 134 of TS-spring hat 122, any excess force then bypasses second rocker DF-resist spring 124 and is instead transmitted via a secondary load path leading from follower pin 126 through rigid elements into TS-spring hat 122 and then merging with primary load path $P'_{DF1}$. In FIG. 24, a secondary dorsiflexion load path $P'_{DF2}$ is illustrated which passes through DF-resist follower pin 126 to second rocker ROM limiter pin 120, through pin 120 to second rocker ROM set screw 118, and through outer threads of set screw 118 to inner threads of TS-spring hat 122, where it merges with primary load path $P'_{DF1}$ to rejoin a merged load path $P'_{DF1,DF2}$.

Figure 23:
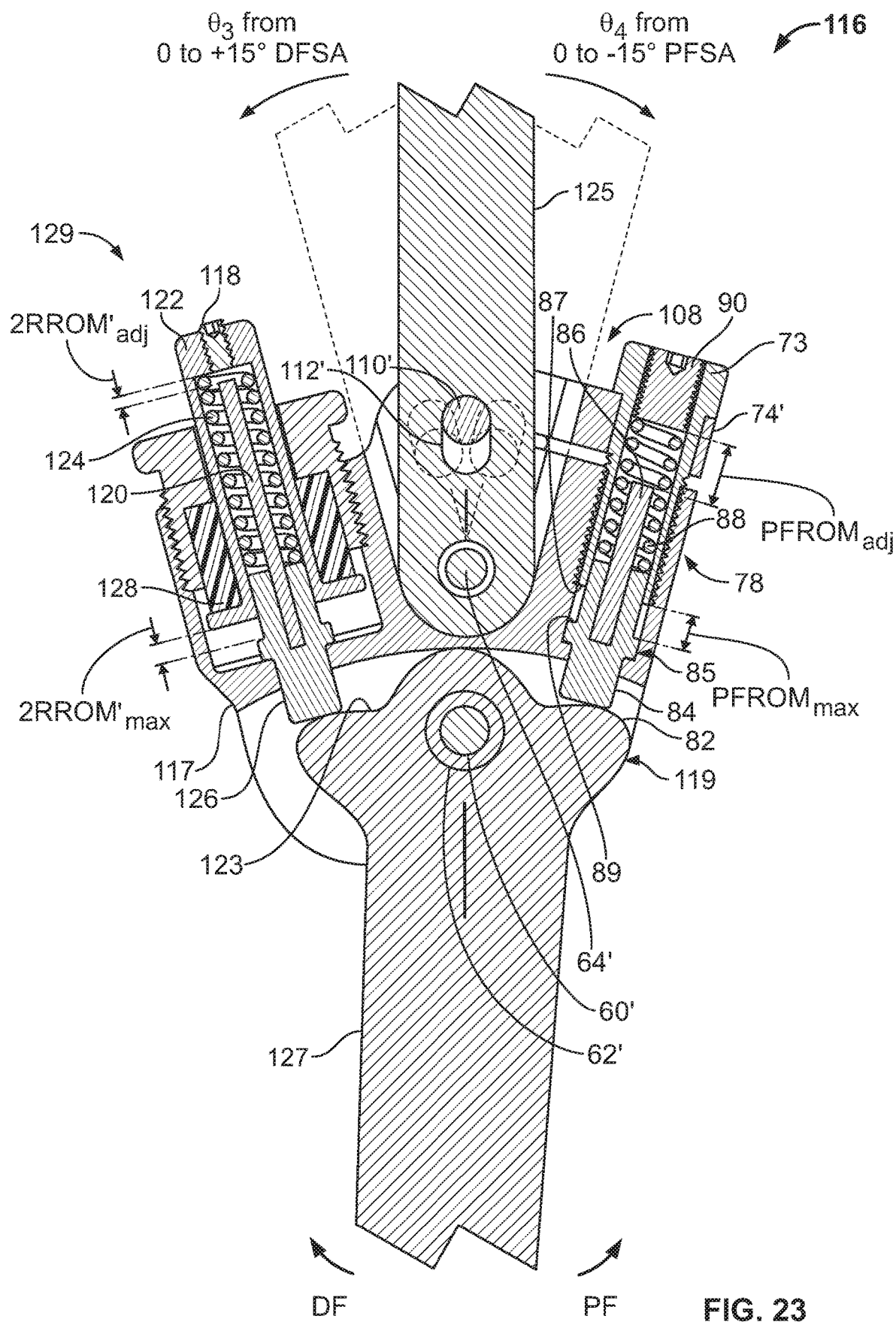
FIG. 23 is a left side sectional elevation view of the device shown in FIG. 16.

With reference to FIG. 23, when set screw 118 is sufficiently retracted so that primary stop clearance $2RROM'_{adj}$ exceeds maximum stop clearance $2RROM'_{max}$, an alternative secondary dorsiflexion load path (not shown) leads directly from follower pin collar 132 to TS-spring hat 122 to rejoin a merged load path. Advantages of imposing a fallback maximum limit on a range of motion in such a manner, whether in plantarflexion or dorsiflexion, may include redundancy to address potential failure or inadvertent removal of set screw 118, protecting helical springs from overloading, protecting a wearer's joints from hyperflexion or a wearer from falling due to instability, and protecting other device components from impact damage, such as by one of the normal contact surfaces of the lower bar/stirrup impacting a sharp corner of the joint body clevis.

Neutral Sagittal Tibial Shank Angle Adjustment

Neutral sagittal tibial shank angle adjustment is provided for substantially as in the first illustrated embodiment. Thus, upper bar 125 is pivotally mounted to joint body 117 to pivot about an upper bar pivot pin 64', and a similar tibial shank angle adjustment cam 66' is provided, with an alternative bolt head 114', cam pin 110', and cam bushing 68'; upper bar 125 including a cam slot 112' for slidingly receiving cam pin 110'. Shank angle adjustment cam 66' is locked by tightening locking bolt 73 to deflect a clamping arm 74' of a tibial shank angle locking collar 76'. In one embodiment, the maximum range of adjustment of tibial shank angle adjustment assembly 108 is from a dorsiflexion angle $\theta_3$ up to about +15° to a plantarflexion angle $\theta_4$ up to about −15°, with respect to a vertical position of upper bar 125 relative to lower bar 127, seen in FIG. 23.

Third Illustrated Staged Resistance Joint Device Embodiment

Figure 25:
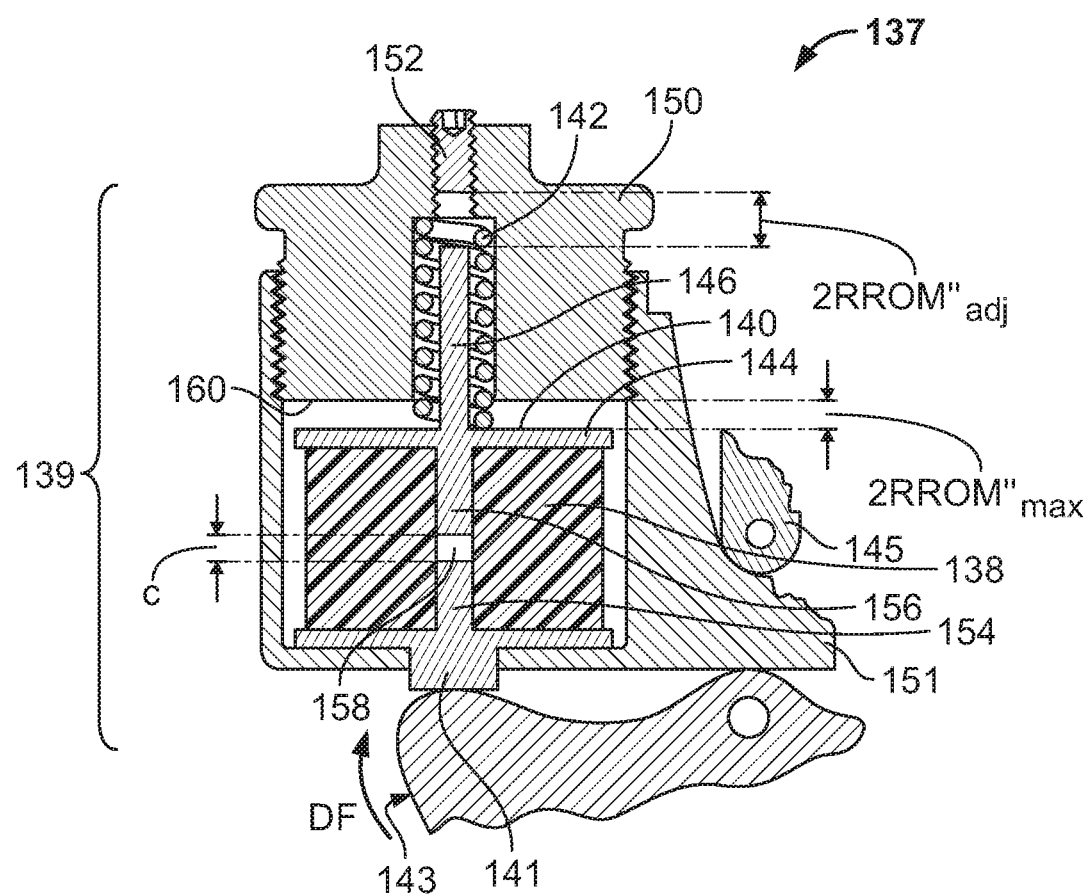
FIG. 25 is a left side fragmentary sectional elevation view of an ankle joint according to another embodiment of the invention.
Figure 26:
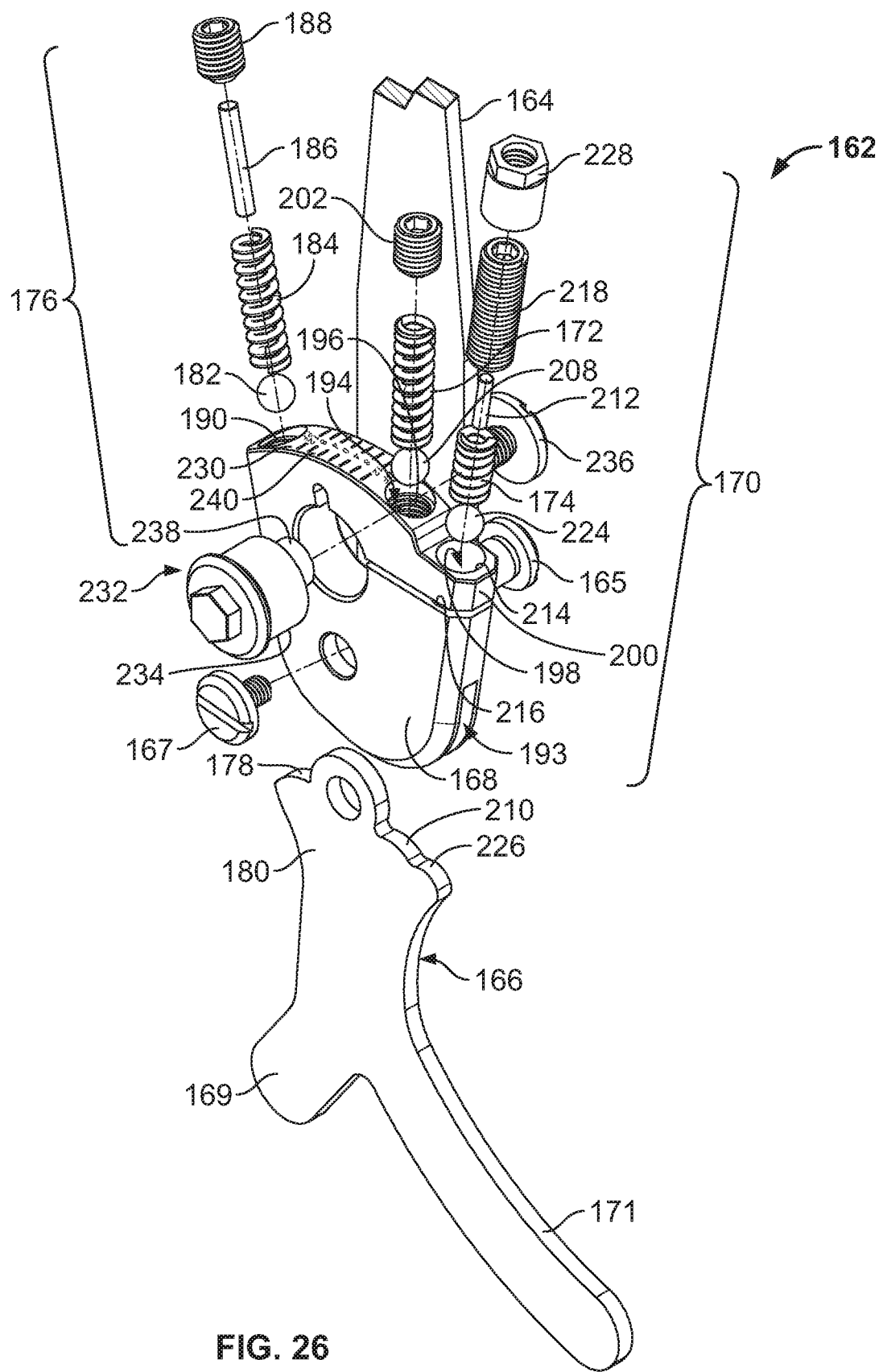
FIG. 26 is an exploded perspective view of an ankle joint according to another embodiment of the invention.
Figure 27:
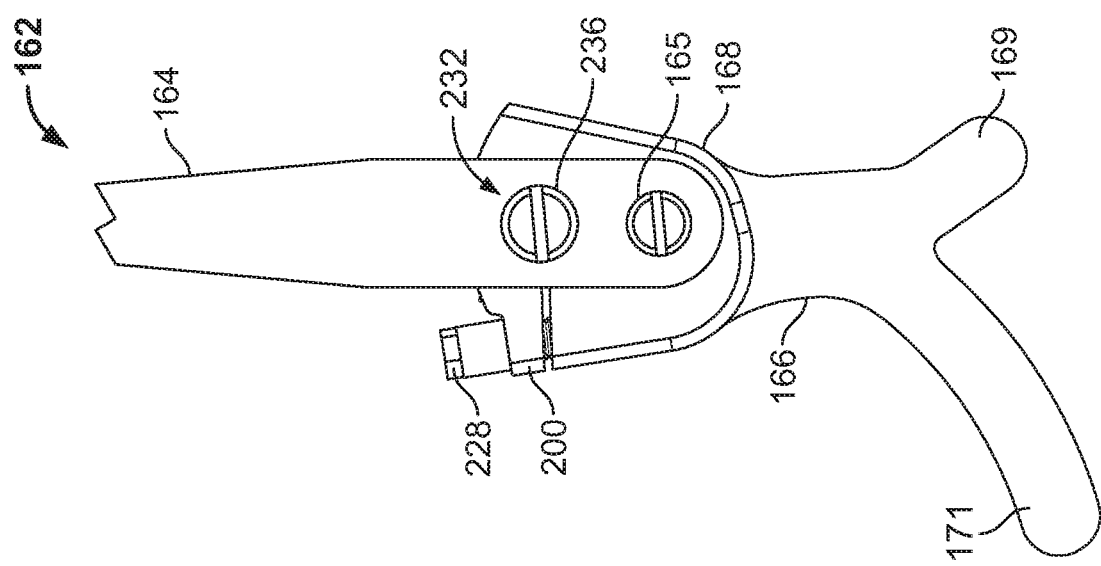
FIG. 27 is a right side elevation view of the assembled ankle joint of FIG. 26.
Figure 28:
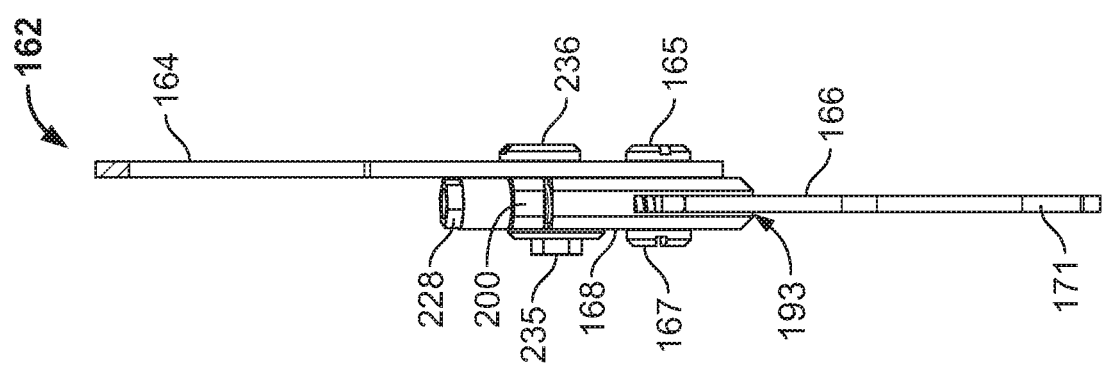
FIG. 28 is a front elevation view of the assembled ankle joint of FIG. 26.
Figure 29:
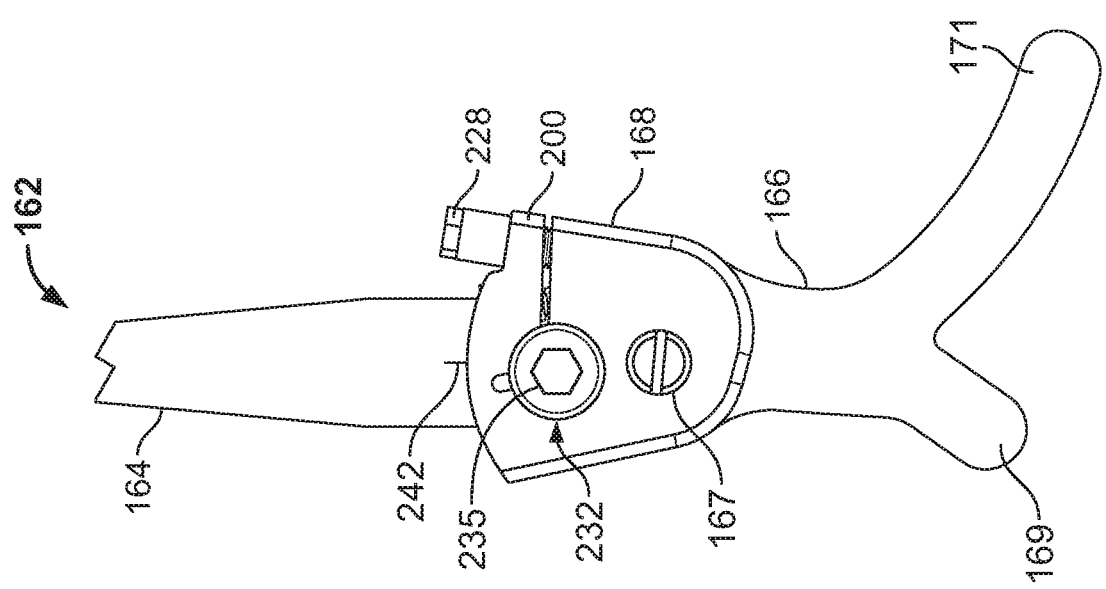
FIG. 29 is a left side elevation view of the assembled ankle joint of FIG. 26.
Figure 30:
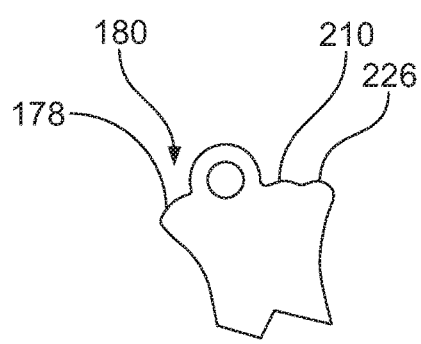
FIG. 30 is a right side fragmentary elevation view of a head component of a lower bar of the ankle joint of FIG. 26.

Another ankle joint device 137 is partially shown in FIG. 25, to illustrate an alternative DF-resist assembly 139 for resisting a dorsiflexion load between a stirrup head 143 and an upper bar 145. DF-resist assembly 139 includes a DF-resist follower pin 141 coupled to a bottom side of a TS DF-resist spring 138, a second rocker ROM-limiter member 140 coupled to a top side of TS DF-resist spring 138, a second rocker DF-resist spring 142 seated at its bottom end on a flange 144 of second rocker ROM-limiter member 140, guided by an inserted ROM-limiter pin 146 of ROM-limiter member 140, and seated at its top end on an annular bottom surface 160 of a DF-resist cap 150 threaded into an ankle joint body 151. Surface 160 surrounds a tapped hole receiving a second rocker ROM set screw 152 and accommodating the insertion of an upper end of ROM-limiter pin 146. The coupling of DF-resist follower pin 141 and ROM-limiter member 140 to TS DF-resist spring 138 maintains a clearance C between respective male coupling features 154, 156 of pin 141 and ROM limiter member 140, permitting TS DF-resist spring 138 to compress when further dorsiflexion load is applied at the end of the second rocker phase. Follower pin 141 and ROM limiter member 140 may either be permanently bonded (for example, by molding or adhesive applied to their respective annular flange surfaces) to TS DF-resist spring 138, or simply inserted into a hollow bore 158 thereof, preferably with a slight interference fit to hold the parts together. Thus, it will be understood that DF-resist assembly 139 provides for setting an adjustable second rocker range of motion $2RROM''_{adj}$ by turning second rocker ROM set screw 152, without affecting a second rocker preload, which may be adjusted by turning DF-resist cap 150, subject to a maximum second rocker range of motion $2RROM''_{max}$ between an annular bottom surface 160 of DF-resist cap 150, which is decreased as a second rocker preload is increased by turning DF-resist cap 150.

Fourth Illustrated Staged Resistance Joint Device Embodiment

Another ankle joint device 162 is illustrated in FIGS. 26-33. Ankle joint device 162 includes an upper bar 164 and a lower bar 166 pivotally connected to a joint body 168 by a shared pivot bushing 165 mounted by a pivot bolt 167. As illustrated in the drawings, lower bar 166 has a general "Y" shape with a heel arm 169 and an arch arm 171 being splayed so as to minimize or avoid impingement with a wearer's ankle and foot bones.

Figure 31:
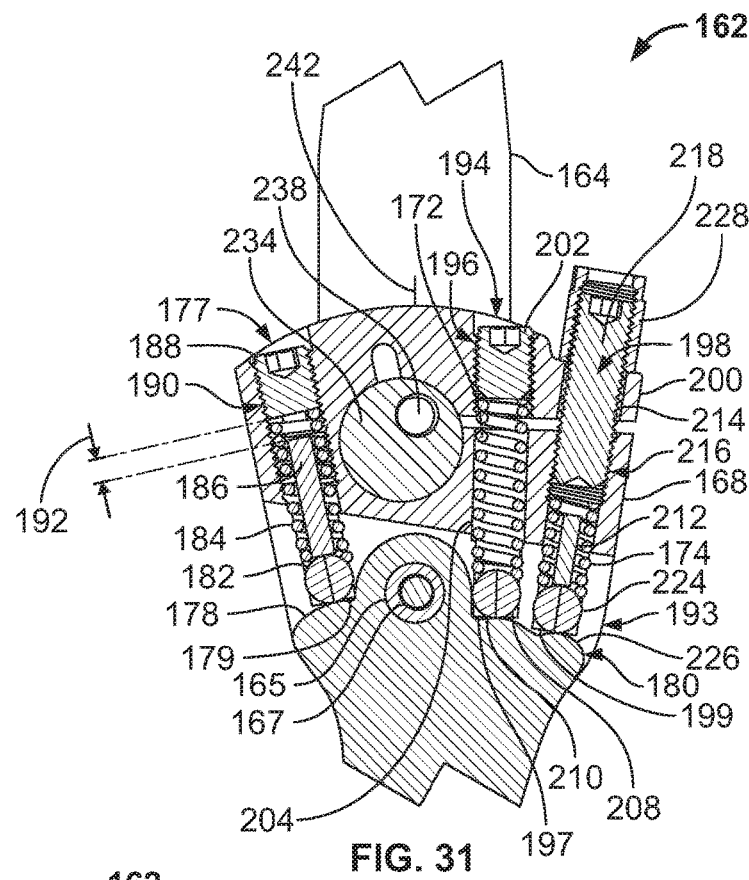
FIG. 31 is a right side fragmentary cross-sectional elevation view of the assembled ankle joint of FIG. 26.
Figure 32:
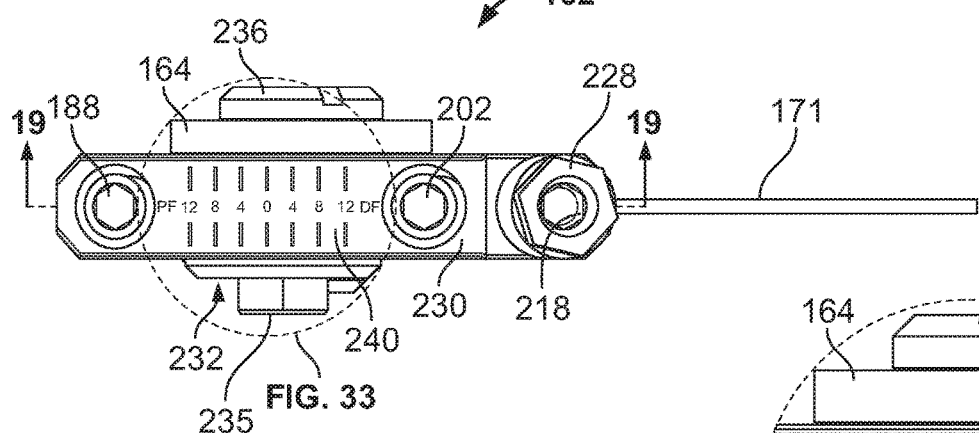
FIG. 32 is a top plan view of the assembled ankle joint of FIG. 26.
Figure 33:
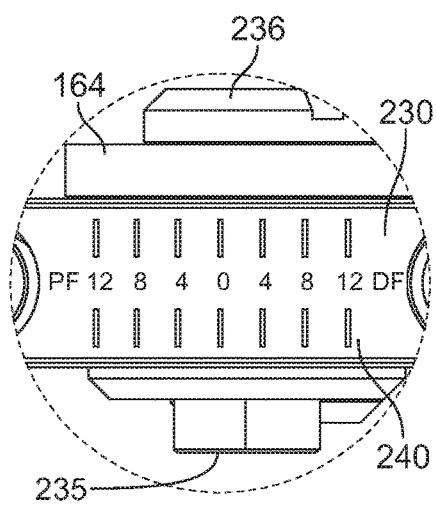
FIG. 33 is an enlarged view of a neutral sagittal tibial shank angle scale shown in the top plan view of FIG. 32.

Joint device 162 differs from the previously described embodiments in that its DF-resist assembly 170 includes a second rocker spring 172 and a TS DF-resist spring 174 that operate in parallel and are mounted side-by-side, as opposed to the nested, series second rocker and TS DF-resist spring assemblies described above; and upper bar 164 is mounted externally to joint body 168. Another difference is the substitution of cam follower ball bearings for cam follower pins in the respective DF-resist and PF-resist assemblies 170, 176. Ball bearings 182, 208, 224 are simply a preferred alternative to a follower pin as in the previously described embodiments, and these or any other suitable types of cam follower members may be employed interchangeably according to the invention in any of its embodiments for converting pivotal movement of a stirrup head to deflection of a suitable spring. Like the follower pins described above, ball bearings according to the invention are preferably made to bottom out in their respective channels by forming an appropriately sized and positioned opening at the bottom of the channel, to limit their travel so that the lower bar is isolated from PF-resist and DF-resist preload forces in its equilibrium position, as well as being isolated from any PF-resist forces in its DF-resist active angular range, and from any DF-resist forces in its PF-resist active angular range. With reference to FIG. 31, to facilitate the use of ball bearings as cam followers, a slot 193 is formed in joint body 168 for receiving stirrup head 180 overlaps a portion of each guide channel 177, 194, 198 in which the respective ball bearing 182, 208, 224 is housed, slot 193 having a smaller width than the ball diameters, and channels 177, 194, 198 having respective blind lower ends 179, 197, 199 except where the slot overlaps the channels, so that the ball bearings are retained in the channels and stirrup head 180 is permitted to invade the channels to displace the ball bearings and deflect their respective springs.

Plantarflexion Resistance and Range of Motion

A PF-resist assembly 176 of joint device 162, residing in a PF-resist spring guide channel 177 formed in joint body 168, includes a PF-resist lobe 178 of a lower bar/stirrup head 180; a PF-resist ball bearing 182; a PF-resist spring 184; a PF ROM limiter pin 186 nested in parallel with PF-resist spring 184, each in load bearing communication with PF-resist ball bearing 182; and a PF-ROM set screw 188 threaded into a tapped upper portion 190 of PF-resist spring guide channel 177, set screw 188 bracing an upper end of PF-resist spring 184 and spaced from an upper end of PF-ROM set screw 188 by a clearance 192 to define a first rocker/plantarflexion range of motion. Aside from the use of PF-resist ball bearing 182 as a cam follower member, PF-resist assembly 176 is otherwise very similar to those described above, in that PF-ROM set screw 188 may be advanced to increase the preload of PF-resist spring 184 and reduce plantarflexion/first rocker range of motion and withdrawn to decrease preload and increase range of motion.

Dorsiflexion Resistance and Range of Motion

DF-resist assembly 170 of joint device 162 is more notably different from those previously described, in that it resides in two separate channels in joint body 168, namely, a second rocker spring guide channel 194 and a TS DF-resist spring guide channel 198 spaced forwardly of channel 194.

Second rocker spring guide channel 194 includes a tapped upper hole 196 formed in a tibial shank angle clamp arm 200 of joint body 168, for receiving a second rocker preload screw 202, and an untapped lower hole 204 formed in a portion of joint body 168 below clamp arm 200, for receiving and guiding the always active second rocker spring 172, operating in compression between preload screw 202 and a second rocker ball bearing 208 riding on a second rocker lobe 210 of stirrup head 180. In the depicted example, an ROM-limiter pin is omitted from channel 194. Although a pin could be used in channel 194 to limit dorsiflexion range of motion, this would have the drawback of potentially transmitting a large parasitic unlocking force to clamp arm 200 at the end of dorsiflexion range of motion, in a worst case potentially freeing upper bar 164 and permitting sudden hyperdorsiflexion that could injure the wearer. Thus, a DF ROM limiter pin 212 is preferably instead housed in TS DF-resist spring guide channel 198 in a load path that bypasses clamp arm 200, as described in the following paragraph.

TS DF-resist spring guide channel 198 includes an untapped upper hole 214 through tibial shank angle clamp arm 200 and a tapped lower hole 216 formed in a portion of joint body 168 below clamp arm 200, for receiving a second rocker/TS ROM set screw 218. Set screw 218 sets the recruitment angle of a TS DF-resist spring 174 housed in tapped lower hole 216 (thus defining a second rocker range of motion) and at the same time imposes a maximum limit on dorsiflexion range of motion by abutting a TS ROM limiter pin 212 nested within and in parallel relation to TS DF-resist spring 174. TS DF-resist spring 174 and TS ROM limiter pin 212 are both supported on a TS ball bearing 224 riding on a TS lobe 226 of stirrup head 180. Finally, a tibial shank angle lock nut 228 is tightened onto an upper end of second rocker/TS ROM set screw 218 to engage clamp arm 200, thus locking upper bar 164 at a desired tibial shank angle. Because lower hole 216 of TS DF-resist spring guide channel 198 is tapped and upper hole 214 is not, any force transmitted by TS DF-resist spring 174, as well as any excess force transmitted by TS ROM limiter pin 212 to set screw 218 bypasses clamp arm 200, is instead borne as a generally upward load by the portion of joint body 168 disposed below clamp arm 200. Accordingly, this load cannot have a parasitic unlocking effect. Preferably, TS DF-resist spring guide channel 198 is packed with damping grease to reduce acoustic noise associated with deflection of TS DF-resist spring 174 or initial contact of TS DF-resist spring 174 or TS ROM limiter pin 212 on second rocker/TS ROM set screw 218.

The springs of PF-resist assembly 176 and DF-resist assembly 170 as described above may be, for example, helical wire springs as depicted in the drawings, which are readily interchangeable with other stiffer or softer springs of like diameter, as desired for a broad range of clinical applications, by simply removing the appropriate set/adjustment screw 188, 202, 218 to remove and replace the respective spring 184, 172, 174. Similarly, PF ROM limiter pin 186 and TS ROM limiter pin 212 may be removed and replaced with longer or shorter pins as desired to make different respective ranges of motion possible.

Neutral Sagittal Tibial Shank Angle Adjustment

Upper bar 164 is mounted to joint body 168 in a similar fashion to the upper bars of the embodiments previously described. Upper bar 164 is mounted to a pivot bushing 165 shared with lower bar 166, as noted above, and is connected to a tibial shank angle adjustment cam 232 that is substantially similar to cam 66 described previously, including a cam bushing 234 (shown in FIG. 31) having an integral adjustment bolt head 235, a cam bolt 236, and an eccentric cam pin 238 (shown in FIG. 31). Cam pin 238 receives bolt 236, revolves around an axis of cam 232, and slides in an elongate cam slot (not shown) in upper bar 164 similar to cam slot 112 of upper bar 58, while cam 232 is locked by tightening lock nut 228 onto clamp arm 200 as noted above. However, unlike in the previously described embodiments, upper bar 164 is mounted to one side of joint body 168 instead of in a slot within a joint body.

Advantageously, this arrangement makes room in joint body 168 for second rocker spring channel 194, as well as affording a wearer or clinician full view of a top surface 230 of joint body 168 providing additional space for tibial shank angle indicia 240 to be printed, engraved, or otherwise applied thereon. Indicia 240 may cooperate with pointer indicia 242 on a side of upper bar 164 facing joint body 168 to indicate a tibial shank angle of upper bar 164 in the sagittal plane relative to lower bar 166.

Fifth Illustrated Staged Resistance Joint Device Embodiment

In the foregoing staged resistance joint device embodiments, staged resistance is provided in an active dorsiflexion range of motion of the illustrated devices, corresponding to dorsiflexion of a wearer's foot. For some applications, however, it may be desirable to provide staged resistance in an active plantarflexion range of motion, corresponding to plantarflexion of a wearer's foot. Following is a discussion of biomechanical considerations for plantarflexion resistance followed by a detailed description of a fifth illustrated staged resistance joint device embodiment, with reference to FIGS. 36-39.

Biomechanical Considerations for Plantarflexion Resistance

When a person walks with weak dorsiflexors, there may be insufficient clearance for the toes in swing. If the weakness is more profound, the position of the ankle may not be maintained in swing, and there may be poor positioning of the foot for heel-first contact when the foot contacts the floor.

When the heel contacts the floor, there is high demand on the ankle dorsiflexors to control the progression of the foot to the floor in the first rocker phase. Even if the dorsiflexors are strong enough to elicit a heel first contact, the higher torque demand through the first rocker phase may nonetheless result in the foot progressing too rapidly to the floor.

If an orthosis is used to resist plantarflexion in the first rocker phase, a knee flexion moment will be elicited. If there is quadriceps weakness, the appropriate plantarflexion resistance through the first rocker phase depends not only on the demand on the ankle dorsiflexors, but also the quadriceps. Setting plantarflexion resistance torque through the first rocker phase, therefore, is a compromise between controlling the ankle in the first rocker phase while avoiding significantly destabilizing the knee in flexion through the first rocker phase.

At the end of the first rocker phase, the foot is flat on the floor. In cases where there is plantarflexion contracture or significant quadriceps insufficiency, there may be hyperextension of the knee following the end of the first rocker phase and through early stance phase of the gait cycle. When this occurs, it may be advantageous to resist plantarflexion more assertively for high plantarflexion angles to indirectly resist knee hyperextension. One application of a staged plantarflexion resistance function is to accommodate these varying torque demands through swing, the first rocker phase and early stance to help improve the stability of both the ankle and knee through these phases of the gait cycle. For example, a smaller plantarflexion resistance torque may be provided through swing and the first rocker phase, while recruiting a higher plantarflexion resistance torque for the high plantarflexion angles that could occur with knee hyperextension following the first rocker phase.

Turning to FIGS. 36-39, a joint device 243 that may be used to provide staged plantarflexion resistance will now be described. Joint device 243 comprises the same components as joint device 162 depicted in FIGS. 26-33, but with an upper bar 245 substituted for upper bar 164 of joint device 162 and a lower bar 247 substituted for lower bar 166 of joint device 162. Upper bar 245 includes an upper bar tibial shank section 249, an angled upper bar section 251, and an upper bar to joint body connecting section 255; likewise, lower bar 247 includes lower bar to foot orthotic attachment arms 261, 263, an angled lower bar section 257, and a lower bar to joint body connecting section 259. Angled upper bar section 251 and angled lower bar section 257 provide differing lateral offsets as needed to provide a desired lateral offset distance L between upper bar tibial shank section 249 and lower bar to foot orthotic attachment arms 261,263, while at the same time sufficiently offsetting joint body 168 appropriately to the right or left of foot orthotic connecting section 255 to provide a suitable clearance between joint body 168 and a wearer's ankle. Lower bar 247 further differs from lower bar 166 in that lower bar to foot orthotic attachment arms 261 and 263 are symmetrical, so that joint device 243 may be interchangeably connected to a foot orthotic (not shown) on either side of a wearer's ankle, inverting the front and back sides of device 243 as needed so that joint body 168 is offset away from the wearer's ankle. Being symmetrical from front to back in the sagittal plane, lower bar 247 connects to a foot orthotic in the same manner in forward and reverse orientations.

Advantageously, the structure of upper bar 245 and lower bar 247 thus permits the same joint device 243 to be alternatively worn on one side of a wearer's ankle, for multistage dorsiflexion resistance and single stage plantarflexion resistance, or on the other side of the wearer's ankle, for multistage plantarflexion resistance and single stage dorsiflexion resistance. Specifically, when joint device 243 is worn at the right side of a wearer's ankle with shank angle lock nut 228 facing forward, joint device 243 provides multistage dorsiflexion resistance, whereas when joint device 243 is worn at the left side of a wearer's ankle with shank angle lock nut 228 facing backward, joint device 243 provides multistage plantarflexion resistance.

In other embodiments of staged resistance joint devices according to an aspect of the invention, two or more springs may be arranged in parallel or series configurations to stage a plantarflexion resistance function, dorsiflexion resistance function, or both plantarflexion and dorsiflexion resistance functions.

Sixth Illustrated Staged Resistance Joint Device Embodiment

In some embodiments of staged resistance joint devices according to the invention, shown in FIGS. 40-45, an adapter is provided to convert an existing joint device into a staged resistance joint device. For example, a single action joint device, such as a dorsiflexion assisting ankle joint, can be converted into a unidirectional staged resistance joint device by threading a staged resistance adapter into a spring channel of the existing device. The staged resistance adapter can be used in a similar manner to convert a dual action joint device into a triple action joint device. Following is a description of a unidirectional resistance joint device 265 (shown in FIGS. 40-44A), a bidirectional resistance triple action joint device 265' (shown in FIG. 44B), and another bidirectional resistance triple action joint device 265" with a different alignment locking mechanism (shown in FIG. 45), each joint device 265, 265', 265" incorporating an adapter 267 in accordance with a sixth illustrated staged resistance joint device embodiment.

Joint device 265 is shown to include a joint body 269, to which an upper bar 271 is fixedly connected by a pair of vertically spaced upper bar mounting bolts 273a, 273b (though not shown, adapter 267 can also be advantageously employed in joint devices including an upper bar that is adjustably connected, by an eccentric cam style alignment mechanism or otherwise, to a joint body) and to which a stirrup 275 is pivotally connected by a pivot bushing 279. As in embodiments previously described herein, stirrup 275 (referred to as a "lower bar" in other embodiments) includes a normal contact stirrup head 277 configured to transmit torques and pivotal movements of stirrup head 277 to a plantarflexion resistance bearing 281 and a dorsiflexion resistance bearing 283 as normal contact forces tending to produce linear translation of respective bearings 281, 283. Plantarflexion resistance bearing 281 and dorsiflexion resistance bearing 283 are so designated for ease of reference, but their roles could be reversed by reversing the front to rear orientation of joint device 265, if stirrup 275 is symmetrical like lower bar (stirrup) 247 of joint device 243, as described above with reference to FIGS. 36-39.

In this illustrated example, joint device 265 is configured as a dorsiflexion assist (plantarflexion resist) ankle device. Thus, dorsiflexion resistance bearing 283 is shown to be arranged in line with a dorsiflexion limiting stop bolt 285, which serves only an alignment/range of motion limiting function by setting a dorsiflexion angle beyond which stirrup head 277 is prevented from pivoting in a dorsiflexion direction. Again, it will be noted that reversing joint device 265 could provide a plantarflexion assist (dorsiflexion resist) device; alternatively, swapping the positions of stop bolt 285 and adapter 267 could likewise reverse the function of the device.

Plantarflexion resistance bearing 281, on the other hand, operatively engages adapter 267, which includes a first stage spring 287 and a second stage spring 289 installed in an in-line parallel arrangement to provide staged plantarflexion resistance. A first stage range of motion (i.e., the active range of motion of first stage spring 287 before recruitment of second stage spring 289) and a pre-load torque of first stage spring 287 is adjusted for swing and the first rocker phase by threading an adapter housing 291 of adapter 267 into (advancing) or out of (withdrawing) a plantarflexion resistance channel 299 of joint body 269. This action compresses or relaxes first stage spring 287 just as would be done for a spring of a traditional clevis style ankle joint. At the same time, withdrawing adapter housing 291 forces the withdrawal of a second stage spring force transmission pin 292, which is slidingly retained in adapter housing 291 and urged to a bottomed out position therein by second stage spring 289. This withdrawal of force transmission pin 292 increases the plantarflexion angle required to bring plantarflexion resistance bearing 281 into contact with a protruding lower end 293 of force transmission pin 292, which is defined as the recruitment angle of second stage spring 289, and also determines the active range of motion 1SROM of first stage spring 287. When a wearer of joint device 265 plantarflexes past the second stage spring recruitment angle, second stage spring 289 begins to compress past its preload compression state. During this second stage of resistance, second stage spring 289 dominates the torque-angle response of joint device 265.

Following adjustment of first stage spring 287, second stage spring 289 is adjusted for resistance to knee hyperextension (i.e. high plantarflexion angles) in early stance. A preload and active range of motion of second stage spring 289 may be adjusted by threading an adjustment screw 294 into (advancing) or out of (withdrawing) adapter housing 291. Advancing adjustment screw 294 increases a preload of second stage spring 289 while at the same time reducing an active second stage range of motion by advancing a second stage motion limiting stop pin 296 integral with adjustment screw 294 closer to a top face 298 of force transmission pin 292. Conversely, withdrawing adjustment screw 294 decreases a preload of second stage spring while at the same time increasing an active second stage range of motion by withdrawing stop pin 296 farther from top face 298 of force transmission pin 292. To eliminate a second stage range of motion altogether, adjustment screw 294 is turned fully clockwise into adapter housing 291 to bring stop pin 296 into contact with top face 298 of force transmission pin 292 while force transmission pin 292 is bottomed out in adapter housing 291, thus preventing any translational movement from being imparted by plantarflexion resistance bearing 281 to second stage spring 289 through force transmission pin 292.

In addition to providing the benefits just described, adapter 267 is advantageously a self-contained component. That is, when adapter 267 is unthreaded completely from a plantarflexion resistance channel 299 formed in joint body 269, adapter housing 291 retains force transmission pin 292, second stage spring 289, and stop pin 296 enclosed between second stage preload and range of motion adjustment screw 294 and an annular interior lower end face 301 of housing 291, which defines an opening 303 of housing 291 having a smaller diameter than a T-head 305 of force transmission pin 292, thereby defining the above described bottomed out position of the latter and preventing its escape from housing 291. In joint device 265, this facilitates easy removal of adapter 267 and first stage spring 287 and swapping of both with stop bolt 285 to reverse the action of joint device 265, without the possibility of components falling out of housing 291 during transfer between plantarflexion resistance channel 299 and a dorsiflexion resistance channel 306 formed in joint body 269.

Figure 44A:
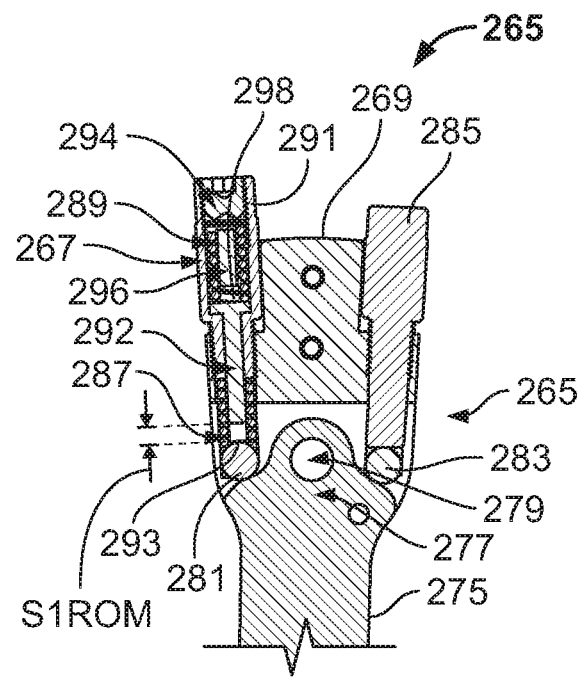
FIG. 44A is a partial right side cross-sectional elevation view of the device shown in FIG. 40.
Figure 44B:
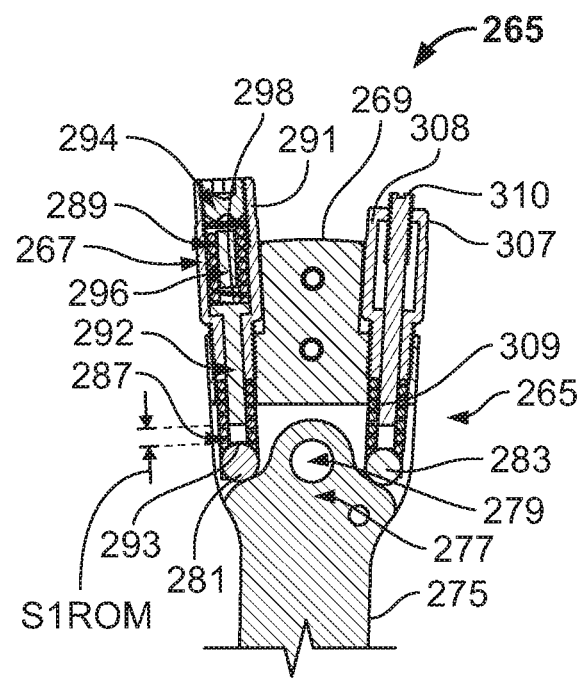
FIG. 44B is a partial right side cross-sectional elevation view of a variation of the device shown in FIG. 40 according to another embodiment of the invention.

In another joint device 265' illustrated in FIG. 44B, shown as a triple action joint device retrofitted from a double action joint device, it will be understood that swapping adapter 267 for a single stage preload and range of motion adjustment component 307 (comprising a single stage preload adjustment housing 308 and a range of motion adjustment screw 310, the gap distance ROM between adjustment screw 310 and dorsiflexion resistance bearing 283 defining an active range of motion of a dorsiflexion resistance spring 309) is even simpler, as dorsiflexion resistance spring 309 is already present in dorsiflexion resistance channel 306. Thus, only adapter 267 need be swapped with single stage adjustment component 307, as first stage spring 287 will remain in place and serve as a single-stage plantarflexion resistance spring in conjunction with single stage adjustment component 307, while dorsiflexion resistance spring 309 will remain in place and serve as a first stage dorsiflexion resistance spring in conjunction with adapter 267.

Though illustrated in the drawings as providing staged plantarflexion resistance, adapter 267 according to this embodiment can be installed in either the plantarflexion resistance or dorsiflexion resistance channel, or both, of a double action or dorsiflexion resist style clevis ankle joint. Adapter 267 can be retrofitted to pre-existing components to implement a staged resistance feature in those components. Further, in addition to ankle joint devices, staged resistance may find advantageous application in other orthotic components as well, including, for example, knee, hip and upper extremity components, in which staged resistance may be provided by a single spring with staged spring rate characteristics or by multiple springs recruited at different stages, arranged in-line or side-by-side, in series or parallel load paths.

Figure 45:
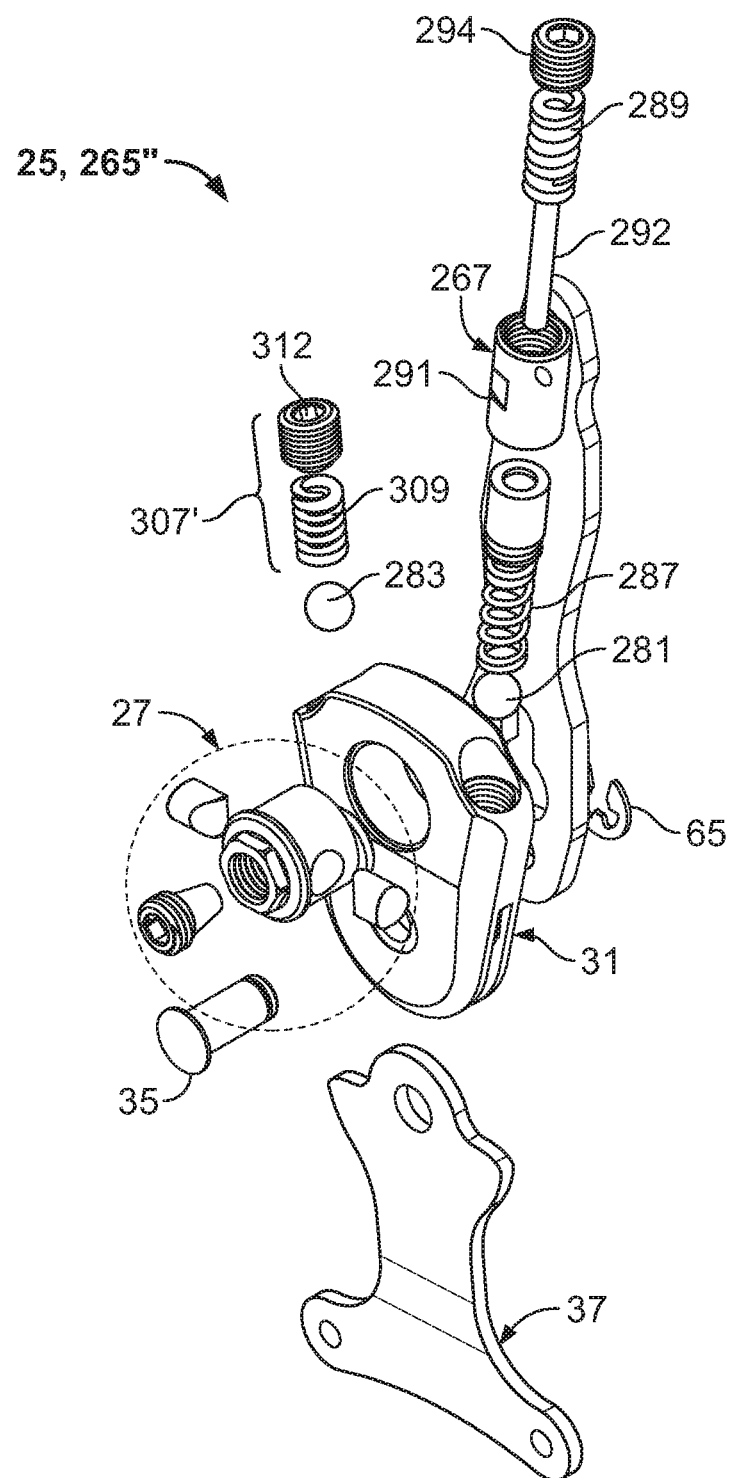
FIG. 45 is an exploded perspective view of a variation of the device shown in FIG. 40 according to another embodiment of the invention.

Another bidirectional resistance joint device 265" is shown in FIG. 45. Joint device 265" differs from device 265' primarily in that it incorporates staged-resistance adapter 267 into a joint device 25, including a locking cam alignment device 27, as described above in the context of an orthotic joint alignment device aspect of the invention. Second-stage spring 289 of adapter 267 is also graphically depicted in FIG. 45 as having a heavier gauge than first-stage spring 287, consistent with the foregoing description of second-stage spring 289 dominating the torque-angle response once it is recruited, and throughout its active range of motion. In addition, a simpler single-stage resistance preload and range of motion adjustment assembly 307' is shown, in which a single adjustment screw 312 controls both range-of-motion and preload adjustments of spring 309. Range-of-motion adjustments of assembly 307' may be made independently of preload adjustments by selecting a limiter pin (not shown) of a desired length to be disposed between bearing 283 and adjustment screw 312, extending through the center of spring 309.

Seventh Illustrated Staged Resistance Joint Device Embodiment

In each of the above described embodiments of staged resistance joint devices, a cam follower (e.g., ball bearings 182, 208, 224 shown in FIG. 31 or follower pins 84, 126 shown in FIG. 24) makes and breaks contact with a cam surface 123 of the stirrup head (56, 180) during articulation through its range of motion. As previously described, making and breaking contact facilitates independent adjustment between dorsiflexion resist, plantarflexion resistance and alignment. This minimal 'crosstalk' between adjustments simplifies clinical application of the device.

However, when the cam follower makes initial contact with the stirrup head, acoustic noise is generated and an audible "click" is heard. This clicking sound may be "amplified" by the structure of the orthosis and may be audible to the user. Like a squeaky shoe, acoustic noise during walking is highly undesirable in orthotic applications, and so it is advantageous to minimize the acoustic noise generated by the component.

Figure 46A:
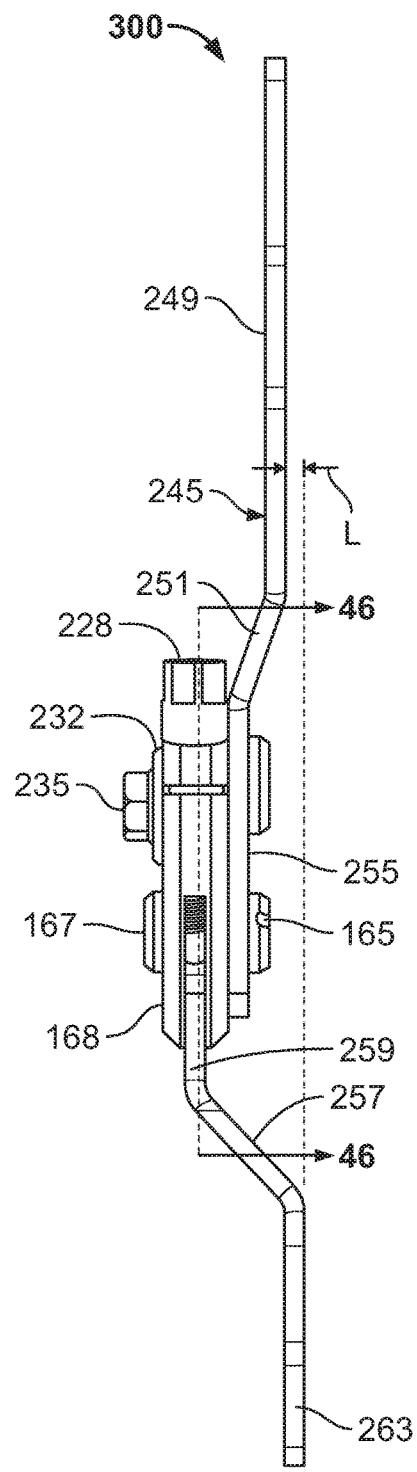
FIG. 46A is a front elevation view of a joint device according to another embodiment of the invention.
Figure 46B:
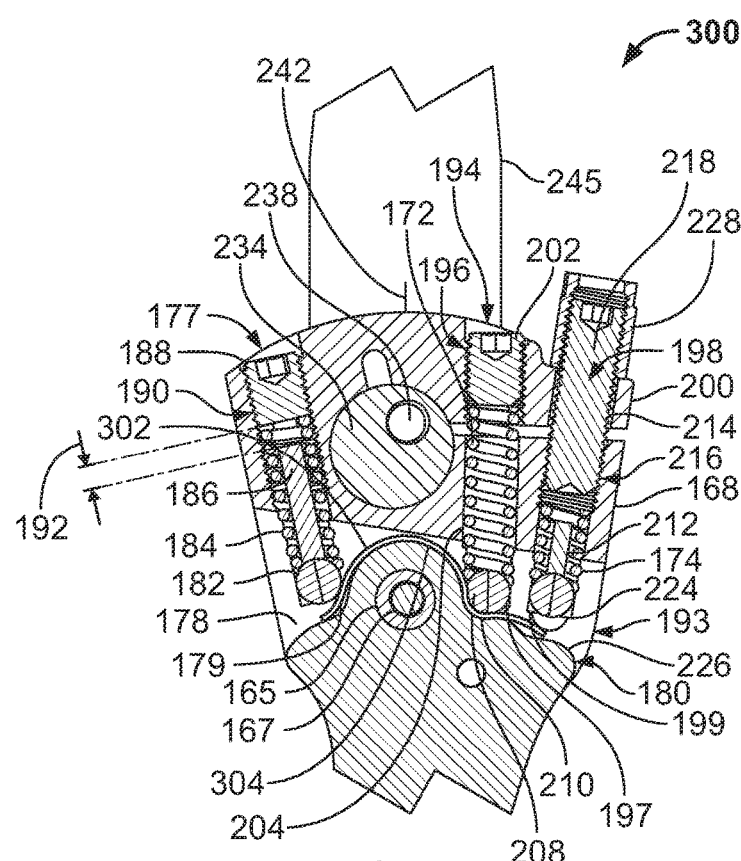
FIG. 46B is a partial right side cross-sectional elevation view of the device shown in FIG. 46A.

In view of the foregoing challenges, a seventh illustrated staged resistance joint device embodiment that significantly decreases this acoustic noise will now be described, with reference to a joint device 300 shown in FIGS. 46A and 46B. Joint device 300 includes substantially the same joint body components as joint devices 162 (FIGS. 26-33) and 243 (FIGS. 36-39), and the same upper and lower bar components as joint device 243, like components being labeled with the same reference numerals. Additionally, joint device 300 includes an acoustic damper 302 in the form of a small flat wire clip spring that fits over a dome 304 of stirrup head 180. Acoustic damper 302 functions by slowing initial contact between ball bearings 182, 208, 224 and respective lobes 178, 210, 226 of stirrup head 180.

In general, a material interposed between a ball bearing cam follower and a stirrup head, so that the ball bearing only directly contacts the interposed material, will attenuate the acoustic noise of initial contact. However, the Hertzian contact stress between the ball and stirrup head is extremely high, and materials interposed in this manner tend to fatigue fail in only a few tens of thousands of cycles. An ankle joint is typically subjected to hundreds of thousands or millions of flexion cycles through its service life, and so a means to attenuate acoustic noise while decreasing the rate of fatigue failure is desirable.

Figure 47:
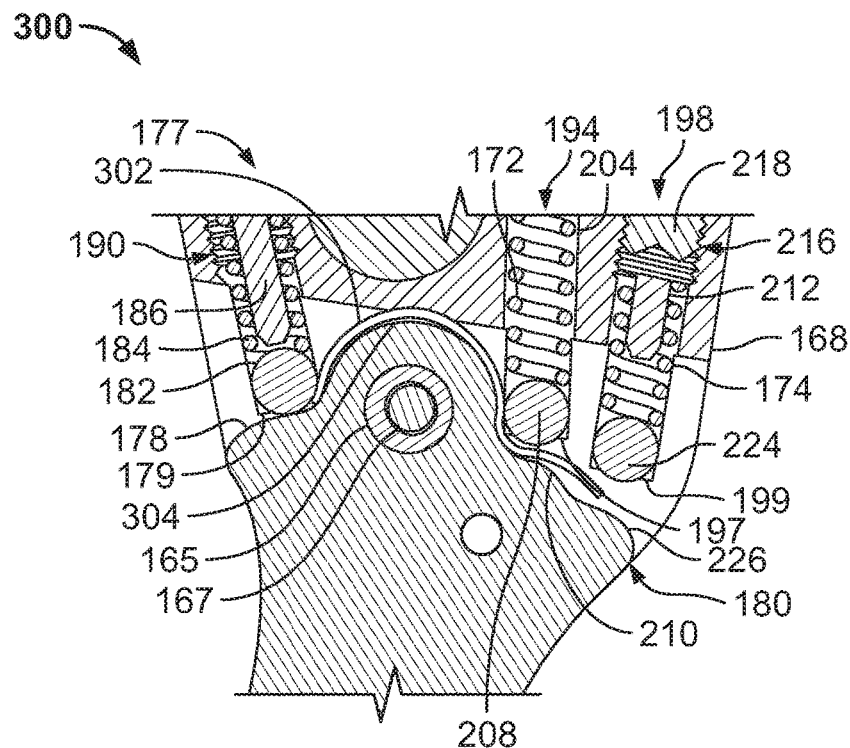
FIG. 47 is a partial right side cross-sectional elevation view as in FIG. 46B showing a pivoted orientation of the joint device.
Figure 48:
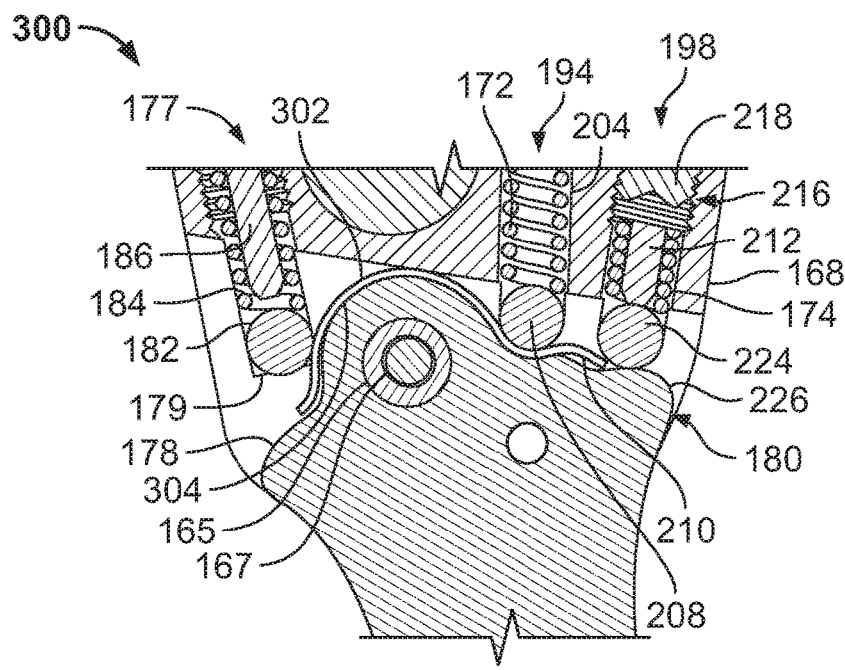
FIG. 48 is a partial right side cross-sectional elevation view as in FIG. 46B showing another pivoted orientation of the joint device.

Advantageously, acoustic damper 302 of joint device 300 slows the impulse of ball bearings 182, 208, 224 against stirrup head 180 at initial contact. In the case of ball bearing 208, this is achieved by the material acoustic damper 302 being pressed against stirrup head 180 by ball bearing 208. This is acceptable and will not result in early fatigue of acoustic damper 302, as the magnitude of Hertzian stresses is limited to the force produced by always active second rocker spring 172, no rigid pin being disposed in second rocker channel 194. In the case of ball bearings 182, 224, on the other hand, attenuating the initial contact impulse is achieved without obstructing the direct contact between ball bearings 182, 224 and stirrup head 180. The respective ends of acoustic damper 302 will deflect transversely out of the way of the bottom center point of respective ball bearings 182, 224 as they settle onto stirrup head 180, as illustrated in FIGS. 47-48 respectively. In particular, as stirrup head 180 rotates, acoustic damper 302 follows stirrup head 180 and its respective ends contact each ball bearing 182, 224 just before ball bearing 182, 224 contacts stirrup head 180. By obliquely contacting ball bearing 182, 224, acoustic damper 302 pushes ball bearing 182, 224 slightly radially in its respective ball channel 177, 198 (i.e., normal to its axis), while at the same time slightly opposing the force of respective springs 184, 174, to ease each ball bearing 182, 224 directly down onto stirrup head 180, reducing the impulse at initial contact. It is believed to be due at least in part to this reduced impulse at initial contact that acoustic damper 302 has been found to decrease the acoustic noise of initial contact by 20 db to 30 db as compared to joint devices 162, 243 without acoustic damper 302. The 'brush' style acoustic noise reduction method exemplified by the operation of acoustic damper 302 in joint device 300 may also be advantageously applied to other orthotic component types or to other mechanisms with intermittent contact.

Graphically Illustrated Gait Cycle

Figure 34:
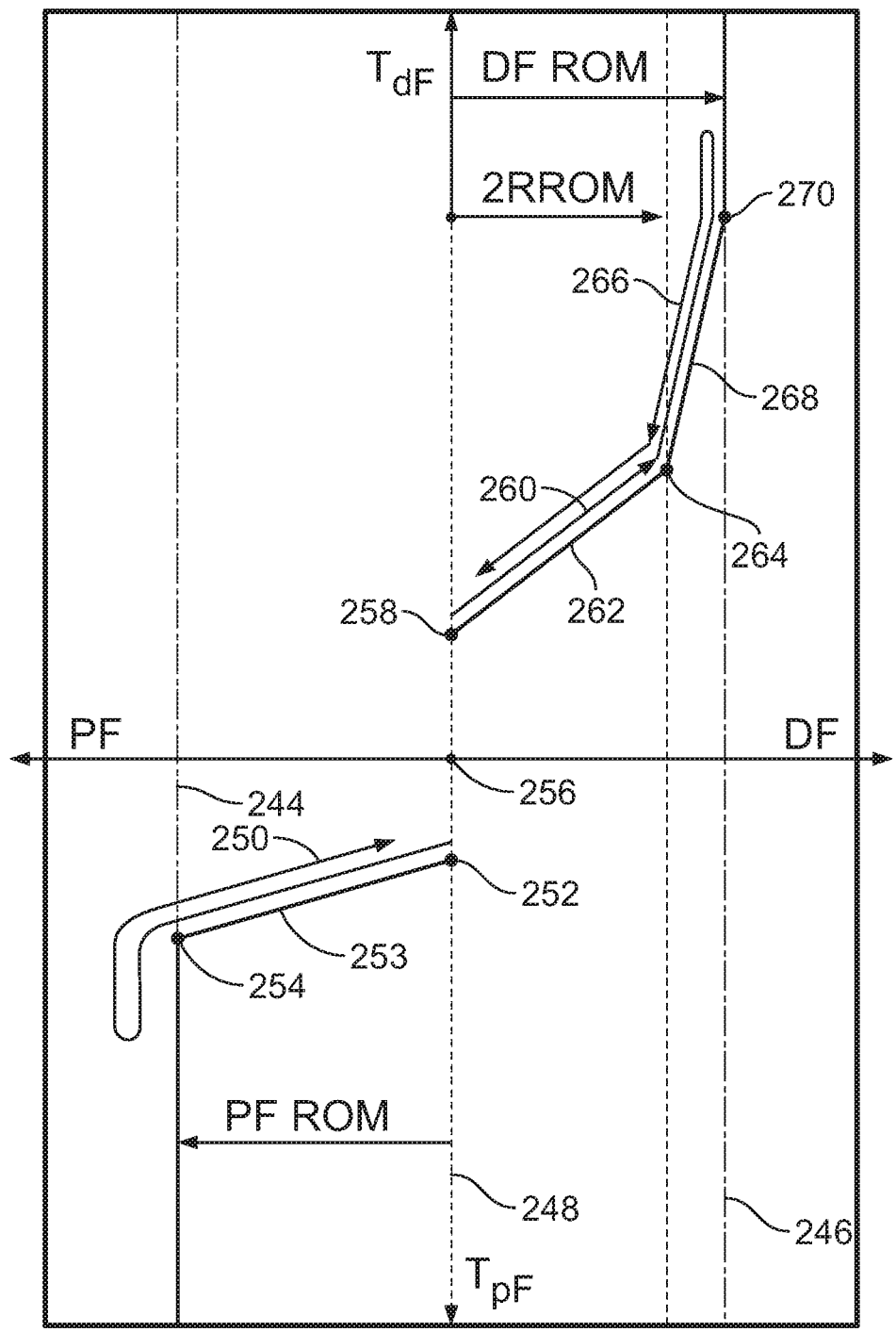
FIG. 34 is a graph depicting a particular representative plantarflexion torque response curve and a particular representative dorsiflexion torque response curve of a device according to the invention.

With reference to FIG. 34, an illustrative example of a gait cycle, proceeding along a particular representative plantarflexion torque response curve and a particular representative dorsiflexion torque response curve, is illustrated graphically with arrows for the first rocker (including any plantarflexion overload at a point of maximum plantarflexion permitted by the device), second rocker, and third rocker/terminal stance (including any dorsiflexion overload at a point of maximum dorsiflexion permitted by the device) phases of a wearer's gait in devices according to the invention. For purposes of this illustrative gait cycle and the various adjusted torque response curves illustrated in FIG. 35 discussed below, a linear torque-angle response is assumed for each spring; however, depending on the type of spring used, any modifications to the spring structure, such as staging or beveling the inner diameter of a polyurethane bushing spring, the shape of the stirrup cam surface, and other parameters, the torque-angle response could be made to be other than linear as desired.

Read clockwise from the bottom axis, the respective axes of the graph indicate plantarflexion torque $T_{pF}$, plantarflexion angle PF, dorsiflexion torque $T_{dF}$, and dorsiflexion angle DF. A maximum plantarflexion angle 244 is indicated by the dashed line toward the left of the figure, and a maximum dorsiflexion angle 246 is indicated by the dashed line toward the right of the figure, with respect to a tibial shank angle 248.

A first rocker phase 250 of a wearer's gait begins with a PF preload torque 252 (which may be zero) at tibial shank angle 248 at heel strike, proceeds along a first rocker torque response curve 241 to a maximum PF torque 254 at maximum PF angle 244 corresponding to ball strike, which may be less than or equal to the PF range of motion permitted by the device. If the wearer plantarflexes to the maximum plantarflexion range of motion PF ROM permitted by the device and continues to bear against the device in plantarflexion, any additional load will be borne by substantially rigid device components so that the torque response curve becomes essentially vertical. The gait cycle then returns along the same torque response curve to PF preload torque 252, if any. If there is a PF preload torque, the response torque then drops to zero at midstance 256, followed by jumping to DF second rocker preload torque 258, if any. It will be noted that if either preload torque 252, 258 is zero, the corresponding torque response curve will simply begin at the origin of the graph shown.

In a second rocker dorsiflexion phase 260, the device torque response then proceeds along a second rocker torque response curve 262 to a second rocker/terminal stance transition torque 264. At this point, corresponding to the limit of second rocker range of dorsiflexion motion 2RROM permitted by the device as adjusted, the terminal stance spring is recruited.

As the dorsiflexion angle continues to increase in a terminal stance phase 266, the resulting TS response curve 268 is steeper than second rocker response curve 262, continuing to a maximum TS (or combined DF-resist, in the case of parallel DF-resist springs) spring torque 270. In terminal stance phase 266, dorsiflexion of the wearer's foot to the maximum dorsiflexion range of motion DF ROM may or may not occur, but with reference to FIG. 35, assuming that the wearer does reach maximum dorsiflexion and continues to bear against the device, the torque response curve will become substantially vertical until the dorsiflexion forces begin to relax, and the gait cycle returns along the same path toward the graph origin to begin again.

Illustrative Adjusted Plantarflexion and Dorsiflexion Torque Response Curves

Figure 35:
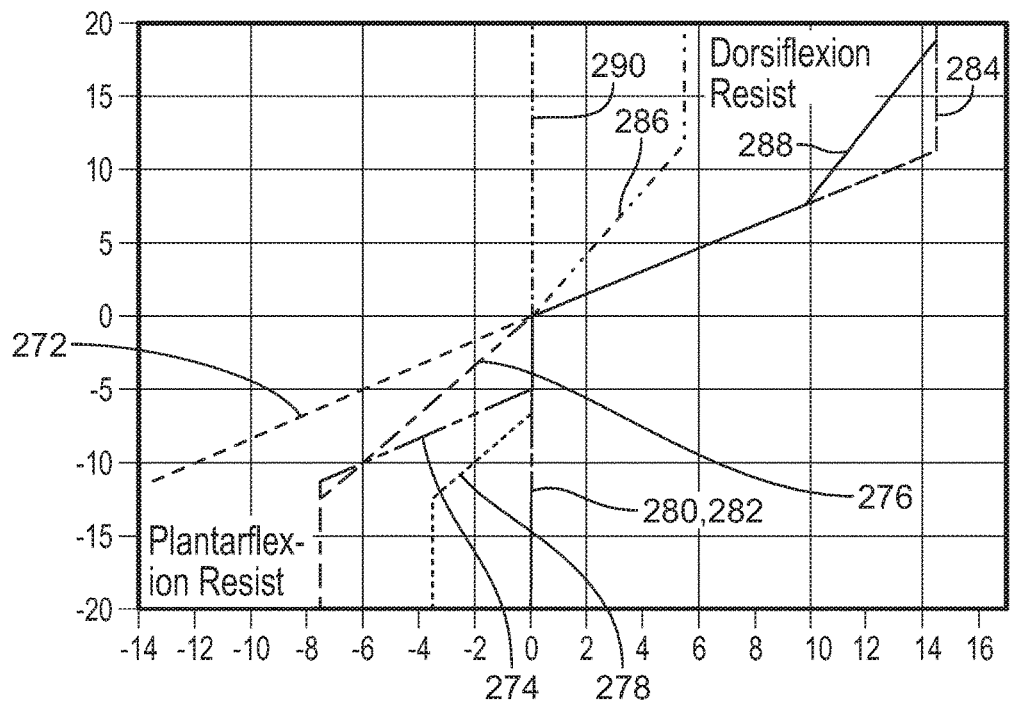
FIG. 35 is a graph depicting the effects of certain adjustments and component substitutions on representative plantarflexion and dorsiflexion torque response curves of a device according to the invention.
Figure 41:
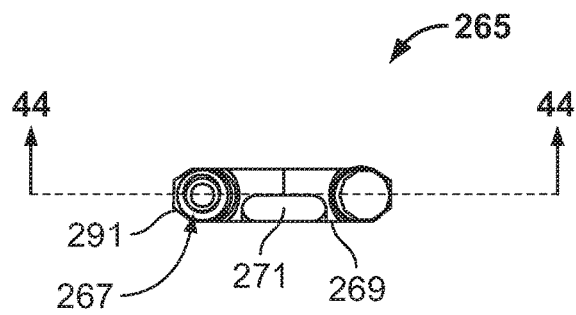
FIG. 41 is a top plan view of the device shown in FIG. 40.
Figure 40:
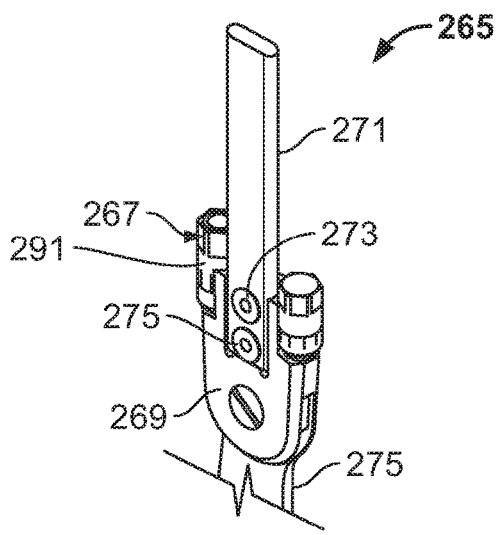
FIG. 40 is a truncated perspective view of a joint device according to another embodiment of the invention.
Figure 42:
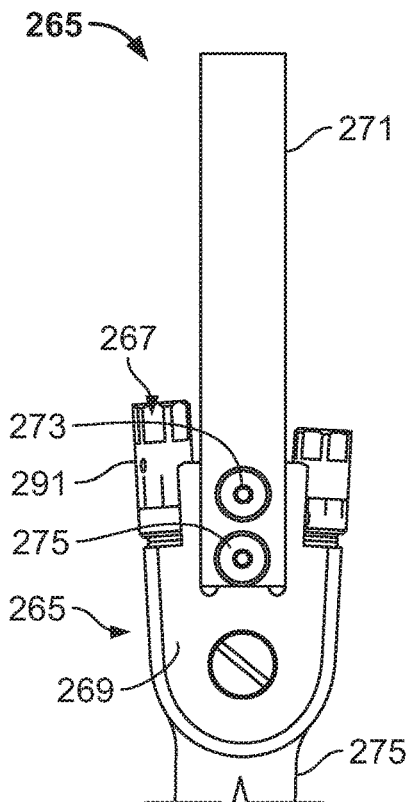
FIG. 42 is a right side elevation view of the device shown in FIG. 40.
Figure 43:
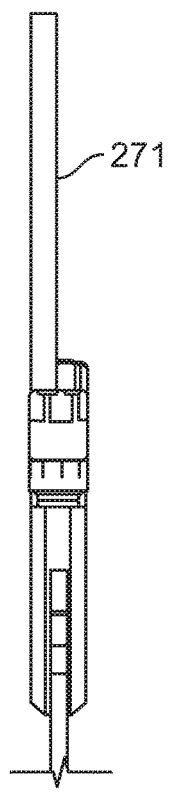
FIG. 43 is a front elevation view of the device shown in FIG. 40.

Turning to FIG. 35, several illustrative plantarflexion-resist and dorsiflexion-resist torque response curves are shown to illustrate the torque response effect of adjustments to ranges of motion, TS DF-resist spring preloading, and spring selection. The curves depicted represent the behavior of the fourth illustrated embodiment of joint device 162, though it will be readily understood that certain features of the curves apply to all four illustrated embodiments. For purposes of this illustration, the second rocker preloads are assumed to be zero; they could be represented as nonzero by simply shifting the curve in question upward by the value of the desired second rocker preload. The origin of the graph represents the device at the tibial shank angle with no active resistance torque applied, the positive angles and positive torques (in N-m) in the upper right quadrant represent angles of dorsiflexion relative to the tibial shank angle and dorsiflexion-resist torques, and the negative angles and negative torques in the lower left quadrant represent angles of plantarflexion relative to the tibial shank angle and plantarflexion-resist torques.

Referring to the lower left quadrant and comparing respective full and 50% range of motion first rocker low torque spring curves 272, 274, and first rocker high torque spring curves 276, 278, one sees that the curves generally shift down and to the right as range of motion is cut in half, which in the illustrated embodiments also entails increasing a first rocker preload (the y-intercepts of 50% ROM curves 274, 278) to half of the peak first rocker spring torque. The respective first rocker low and high torque 0% ROM curves 280, 282 are simply vertical lines extending downwardly from the origin, as 0% range of motion means that plantarflexion is essentially prevented for any plantarflexion torque that could be expected to come from a human wearing the device.

Referring to the upper right quadrant, a second rocker resistance curve 284 reflects the behavior of always active second rocker spring 172 of device 162, to which a second rocker preload could be applied by shifting any dF-resist curve upward by the magnitude of the preload, as noted above. A dF-resist curve of device 162 will follow curve 284 up to the angle of recruitment of TS DF-resist spring 174 and then continue along a steeper slope equal to the sum of the respective spring rates of second rocker spring 172 and TS DF-resist spring 174, now engaged in parallel. Thus, a dF-resist curve 286 with a 0% pre-compressed TS DF-resist spring 174 recruited at 0° departs from the origin with a uniform steep slope until TS ROM limiter pin 212 bottoms out and the slope becomes vertical, whereas a dF-resist curve 288 with a 0% pre-compressed TS DF-resist spring 174 recruited at 9° follows second rocker resistance curve 284 up to 9° dorsiflexion, followed by departing from curve 284 at 9° with the same slope as curve 286. Finally, similarly to the 0% plantarflexion ROM curves 280, 282, a 100% pre-compressed TS DF-resist spring recruited at 0° dorsiflexion (i.e., TS ROM set screw 218 is tightened until it meets TS ROM limiter pin 212 with TS ball bearing 224 bottomed out in its channel 198) results in preventing essentially any dorsiflexion from the tibial shank angle, corresponding to a dF-resist curve 290 that is simply a vertical line extending upwardly from the origin.

Summary of Illustrative Performance Specifications

Typical performance specifications of devices according to the invention, also mentioned above in discussing each separate function/assembly of device 52, are as follows: A representative tibial shank angle/equilibrium ankle angle adjustment range is about +/−15° from a vertical angle of an upper bar or other lower leg attachment member. A typical active plantarflexion resistance range of motion is up to about (−14°) of plantarflexion. A typical active second rocker range of motion is up to about (+10°) of dorsiflexion, and a typical active terminal stance range of motion is up to about (+7°) of additional dorsiflexion, for up to about 17° of total dorsiflexion. Plantarflexion and dorsiflexion resisting torques are typically functionally isolated, as is the case in all of the illustrated embodiments, such that torque adjustments and adjustments to preload torques for dorsiflexion resist are completely isolated and functionally independent from torque adjustments and adjustments to preload torques for plantarflexion resist.

Materials and Construction

Components of devices according to the invention may be formed of steel, aluminum, titanium, polymer composite or other material suitable for orthotic devices. With the exception of the polyurethane bushing TS DF-resist springs illustrated in the first through third embodiments, springs employed in the illustrated embodiments may typically be composed of spring steel wire or other metallic or non-metallic alloys as are suitable to generate torques consistent with performance requirements of the joint component for orthotic service. Machined springs according to the invention may typically be made from a metal bar starting material, but they may be formed of any suitable machinable material, including some plastics. Additionally, springs comprised of gas cylinders, such as nitrogen gas springs, for example, may be substituted for the springs used in the illustrated embodiment or employed in other embodiments not shown.

Variations of the Invention

While the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An orthosis including a joint device, the joint device comprising:
   a joint body;
   a first attachment member pivotally connected to the joint body, for pivotal movement about a first axis in a flexion direction and an extension direction opposite to the flexion direction;
   a flexion resistance spring configured to bias the first attachment member in an extension direction relative to the joint body when the first attachment member is within a flexion resistance spring active angular range, the flexion resistance spring active angular range beginning at a flexion resistance spring recruitment angle and increasing in flexion therefrom;
   an extension resistance spring configured to bias the first attachment member in a flexion direction relative to the joint body when the first attachment member is within an extension resistance spring active angular range, the extension resistance spring active angular range beginning at an extension resistance spring recruitment angle and increasing in extension therefrom;
   a second attachment member pivotally connected to the ankle joint body about a second axis; and
   a second attachment member locking mechanism operable to lock the second attachment member at a selected angle relative to the joint body, one of the first attachment member and the second attachment member being configured for attachment to a first limb segment of a human wearer of the device, and the other being configured for attachment to a second limb segment of the human wearer.

2. The orthosis of claim 1, the first attachment member being positionable in at least one neutral angle relative to the joint body in which the net biasing torque transmitted to the first attachment member from the joint body is zero, the neutral angle being between the angle of greatest flexion in the flexion resistance spring active angular range and the angle of greatest extension in the extension resistance spring active angular range.

3. The orthosis of claim 1 further comprising
   a cam bushing rotatably retained relative to the first attachment member to permit rotation of the cam bushing about a cam bushing axis, the cam bushing including an eccentric cam pin displaced at a fixed distance from the cam bushing axis in a radial direction perpendicular to the cam bushing axis to permit revolution of the eccentric cam pin around the cam bushing axis when the cam bushing rotates about the cam bushing axis; and
   a cam slot in fixed relation to the second attachment member, the cam slot retaining the eccentric cam pin, the cam slot configured to guide translational movement of the eccentric cam pin along a length of the cam slot, and the second attachment member being configured to impel said translational movement of the eccentric cam pin along the length of the cam slot and to impel revolution of the eccentric cam pin about the cam bushing axis when the second attachment member is pivoted relative to the first attachment member;
   wherein engagement of said locking mechanism is configured to frictionally restrain the cam bushing from rotating relative to the first attachment member so that contact between the eccentric cam pin and cam slot restrains the second attachment member from pivoting relative to the first attachment member.

4. The orthosis of claim 3, further comprising a cam bushing retention surface, the cam bushing retention surface disposed proximate to and facing a retained surface of the cam bushing to restrain radial movement of the cam bushing relative to the first attachment member in said radial direction.

5. The orthosis of claim 4, the retained surface of the cam bushing being a surface disposed radially inwardly of the cam bushing retention surface, and the locking mechanism configured to apply a radially inward clamping force from the cam bushing retention surface to the retained surface of the cam bushing to produce said engagement of the locking mechanism.

6. The orthosis of claim 3 wherein the cam slot is elongate.

7. The orthosis of claim 3 wherein the bushing retention surface is integral to the first attachment member.

8. The orthosis of claim 3 wherein the orthosis is an ankle foot orthosis comprising the flexion resistance spring and the extension resistance spring and the extension resistance spring is an initial dorsiflexion resistance spring, the orthosis further comprising a terminal stance dorsiflexion resistance spring configured to bias the first attachment member in a plantarflexion direction relative to the joint body when the first attachment member is within a terminal stance dorsiflexion resistance spring active angular range; the terminal stance dorsiflexion resistance spring active angular range having at least a terminal stance dorsiflexion resistance spring recruitment angle and an angular range increasing in dorsiflexion therefrom, the terminal stance dorsiflexion resistance spring recruitment angle being greater in dorsiflexion than the initial dorsiflexion resistance spring recruitment angle.

9. The orthosis of claim 8, the first attachment member comprising a first attachment arm extending in a generally forward direction and a second attachment arm extending in a generally rearward direction, the first and second attachment arms being generally symmetrical about a frontal plane perpendicular to the forward and rearward directions, so that reversing an orientation of the device from a forward facing orientation to a rearward facing orientation does not change a combined shape of the first attachment arm and the second attachment arm in a sagittal plane perpendicular to the frontal plane; and/or the initial dorsiflexion resistance spring and the terminal stance dorsiflexion resistance spring being comprised in a single spring having a higher effective spring rate in the terminal stance dorsiflexion resistance spring active angular range than in a range of angles between the initial dorsiflexion resistance spring recruitment angle and the terminal stance dorsiflexion resistance spring recruitment angle.

10. The orthosis of claim 8, further comprising
a dorsiflexion resistance transmission member operatively connected between the joint body and the first attachment member and biased to move toward the first attachment member in a direction that opposes dorsiflexion movement of a dorsiflexion-resist contact surface of the first attachment member, a fixed dorsiflexion-resist stop restricting said dorsiflexion opposing movement toward the first attachment member beyond a neutral position of the dorsiflexion-resist transmission member where the dorsiflexion-resist transmission member abuts the dorsiflexion-resist contact surface of the first attachment member disposed at said neutral angle; and
a plantarflexion-resist transmission member operatively connected between the joint body and the first attachment member and biased to move toward the first attachment member in a direction that opposes plantarflexion movement of a plantarflexion-resist contact surface of the first attachment member, a fixed plantarflexion-resist stop restricting said dorsiflexion opposing movement toward the first attachment member beyond a neutral position of the plantarflexion-resist transmission member where the plantarflexion-resist transmission member abuts the plantarflexion-resist contact surface of the first attachment member disposed at said neutral angle.

11. The orthosis of claim 8, the initial dorsiflexion resistance and terminal stance dorsiflexion resistance springs being operatively connected in series between the first attachment member and the joint body when the first attachment member is positioned between the initial dorsiflexion resistance spring recruitment angle and the terminal stance dorsiflexion resistance spring recruitment angle.

12. The orthosis of claim 8, further comprising
a first initial range of dorsiflexion limiting member spaced by a first clearance from a first terminal stance dorsiflexion resistance spring engagement surface when the first attachment member is at the initial dorsiflexion resistance spring recruitment angle, the terminal stance dorsiflexion resistance spring being deflectable to produce said terminal dorsiflexion resisting force by movement of said first terminal stance dorsiflexion resistance spring engagement surface,
a first terminal stance dorsiflexion resistance spring engagement surface being fixed relative to a first attachment member engaging end of the terminal stance dorsiflexion resistance spring;
a second initial range of dorsiflexion limiting member spaced by a second clearance from a second terminal stance dorsiflexion resistance spring engagement surface when the first attachment member is at the initial dorsiflexion resistance spring recruitment angle, the terminal stance dorsiflexion resistance spring being deflectable to produce said terminal dorsiflexion resisting force by movement of said second terminal stance dorsiflexion resistance spring engagement surface, and
a second terminal stance dorsiflexion resistance spring engagement surface being configured to maintain a fixed position relative to a first attachment member engaging end of the terminal stance dorsiflexion resistance spring when subjected to a force in a direction of movement impelled by dorsiflexion movement of the first attachment member, said fixed position of the second terminal stance dorsiflexion resistance spring engagement surface being adjustable relative to a position of a joint body engaging end of the terminal stance dorsiflexion resistance spring;
the first attachment member configured to move the first initial range of dorsiflexion limiting member toward the first terminal stance dorsiflexion resistance spring engagement surface and the second initial range of dorsiflexion limiting member toward the second terminal stance dorsiflexion resistance spring engagement surface upon further dorsiflexion movement of the first attachment member from the initial dorsiflexion resistance spring recruitment angle; and
the terminal stance dorsiflexion resistance spring recruitment angle being an angle of the first attachment member at which one of the first initial range of dorsiflexion limiting member and the second initial range of dorsiflexion limiting member contacts the respective first or second terminal stance dorsiflexion resistance spring engagement surface.

13. The orthosis of claim 8, the initial dorsiflexion resistance spring and the terminal stance dorsiflexion resistance spring being linear compression springs mounted side-by-side in parallel operative engagement between the first attachment member and the joint body.

14. The orthosis of claim 1, wherein the second axis is through the joint body.

15. The orthosis of claim 14, wherein the first axis is through the joint body.

16. The orthosis of claim 15, wherein the first axis and the second axis are the same.

17. The orthosis of claim 1, wherein the first axis and the second axis are the same.

18. The orthosis of claim 1 wherein the orthosis is an ankle foot orthosis.

\* \* \* \* \*

UNITED STATES PATENT AND TRADEMARK OFFICE
CERTIFICATE OF CORRECTION

PATENT NO. : 11,850,176 B2
APPLICATION NO. : 17/861053
DATED : December 26, 2023
INVENTOR(S) : Nicholas LeCursi et al.

Page 1 of 1

It is certified that error appears in the above-identified patent and that said Letters Patent is hereby corrected as shown below:

In the Specification

Column 6, Line 22, delete "effected" and insert -- affected --.
Column 10, Line 13, delete "effected" and insert -- affected --.
Column 10, Line 49, delete "effected" and insert -- affected --.
Column 31, Line 31, delete "PDF" and insert -- F'DF --.
Column 31, Line 47, delete "PDF" and insert -- F'DF --.
Column 42, Line 54, delete "(-14°)" and insert -- (-)14° --.
Column 42, Line 55, delete "(+10°)" and insert -- (+)10° --.
Column 42, Line 57, delete "(+7°)" and insert -- (+)7° --.

In the Claims

Column 43, Line 46, delete "ankle".

Signed and Sealed this
Eighteenth Day of March, 2025

Coke Morgan Stewart
*Acting Director of the United States Patent and Trademark Office*